US011542335B2

(12) United States Patent
Hoves et al.

(10) Patent No.: US 11,542,335 B2
(45) Date of Patent: Jan. 3, 2023

(54) METHOD OF TREATING CANCER IN A PATIENT BY ADMINISTERING AN ANTIBODY WHICH BINDS COLONY STIMULATING FACTOR-1 RECEPTOR (CSF-1R)

(71) Applicant: Hoffmann-La Roche Inc., Little Falls, NJ (US)

(72) Inventors: Sabine Hoves, Habach (DE); Chia-Huey Ooi, Grenzach-Wyhlen (DE); Carola Ries, Penzberg (DE); Solange Romagnoli, Basel (CH); Dominik Ruettinger, Seehausen (DE); Hadassah Sumum Sade, Penzberg (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 16/285,064

(22) Filed: Feb. 25, 2019

(65) Prior Publication Data

US 2019/0284284 A1 Sep. 19, 2019

Related U.S. Application Data

(63) Continuation of application No. PCT/EP2017/070570, filed on Aug. 14, 2017.

(30) Foreign Application Priority Data

Aug. 25, 2016 (EP) .................................. 16185704

(51) Int. Cl.
*A61P 35/00* (2006.01)
*A61K 39/00* (2006.01)
*C07K 16/28* (2006.01)

(52) U.S. Cl.
CPC .......... *C07K 16/2866* (2013.01); *A61P 35/00* (2018.01); *C07K 16/2827* (2013.01); *C07K 16/2878* (2013.01); *A61K 2039/507* (2013.01); *A61K 2039/545* (2013.01); *C07K 2317/75* (2013.01); *C07K 2317/76* (2013.01)

(58) Field of Classification Search
CPC ............ C07K 16/2827; C07K 16/2866; C07K 16/2878; C07K 2317/75; C07K 2317/76; A61P 35/00; A61P 43/00; A61P 37/02; A61P 37/04; A61P 35/02; A61K 2039/507; A61K 2039/545
See application file for complete search history.

(56) References Cited

U.S. PATENT DOCUMENTS

| | | |
|---|---|---|
| 5,202,238 A | 4/1993 | Fell, Jr. et al. |
| 5,204,244 A | 4/1993 | Fell, Jr. et al. |
| 5,208,020 A | 5/1993 | Chari et al. |
| 5,416,064 A | 5/1995 | Chari et al. |
| 5,635,483 A | 6/1997 | Pettit et al. |
| 5,712,374 A | 1/1998 | Kuntsmann et al. |
| 5,714,586 A | 2/1998 | Kunstmann et al. |
| 5,739,116 A | 4/1998 | Hamann et al. |
| 5,767,285 A | 6/1998 | Hamann et al. |
| 5,770,701 A | 6/1998 | McGahren et al. |
| 5,770,710 A | 6/1998 | McGahren et al. |
| 5,773,001 A | 6/1998 | Hamann et al. |
| 5,780,588 A | 7/1998 | Pettit et al. |
| 5,798,229 A | 8/1998 | Strittmatter et al. |
| 5,866,114 A | 2/1999 | Pandit et al. |
| 5,877,296 A | 3/1999 | Hamann et al. |
| 5,961,974 A | 10/1999 | Armitage |
| 5,981,724 A | 11/1999 | Armitage |
| 6,184,354 B1 | 2/2001 | Koths et al. |
| 6,391,637 B1 | 5/2002 | Armitage |
| 6,410,711 B1 | 6/2002 | Armitage |
| 6,630,579 B2 | 10/2003 | Chari et al. |
| 6,946,129 B1 | 9/2005 | Siegall |
| 7,108,852 B2 | 9/2006 | Devalaraja et al. |
| 7,223,741 B2 | 5/2007 | Krieg |
| 7,288,251 B2 | 10/2007 | Bedian et al. |
| 7,338,660 B2 | 3/2008 | Bedian |
| 7,498,298 B2 | 3/2009 | Doronina et al. |
| 8,182,813 B2 | 5/2012 | Brasel et al. |
| 8,217,149 B2 | 7/2012 | Irving et al. |
| 8,263,079 B2 | 9/2012 | Doody et al. |
| 8,303,955 B2 | 11/2012 | Presta |
| 8,470,977 B2 | 6/2013 | Haegel et al. |
| 8,604,170 B2 | 12/2013 | Haegel et al. |
| 8,993,614 B2 | 3/2015 | Bartkovitz et al. |
| 8,999,327 B2 | 4/2015 | Dimoudis et al. |
| 9,169,323 B2 | 10/2015 | Fertig et al. |
| 9,192,667 B2 | 11/2015 | Hoves et al. |
| 9,221,910 B2 | 12/2015 | Fertig et al. |
| 9,499,624 B2 | 11/2016 | Dimoudis et al. |
| 9,499,625 B2 | 11/2016 | Dimoudis et al. |
| 9,499,626 B2 | 11/2016 | Dimoudis et al. |
| 9,617,342 B2 | 4/2017 | Fertig et al. |
| 9,624,302 B2 | 4/2017 | Fertig et al. |
| 9,663,580 B2 | 5/2017 | Dimoudis et al. |
| 9,879,085 B2 | 1/2018 | Dimoudis et al. |
| 9,988,458 B2 | 6/2018 | Fertig et al. |
| 10,023,643 B2 | 7/2018 | Fertig et al. |
| 10,030,073 B2 | 7/2018 | Fertig et al. |
| 10,072,087 B2 | 9/2018 | Dimoudis et al. |
| 10,077,314 B1 | 9/2018 | Dimoudis et al. |
| 10,287,358 B2 | 5/2019 | Dimoudis et al. |
| 10,336,830 B2 | 7/2019 | Fertig et al. |

(Continued)

FOREIGN PATENT DOCUMENTS

| | | |
|---|---|---|
| CN | 101636412 A | 1/2010 |
| CN | 102791738 A | 11/2012 |

(Continued)

OTHER PUBLICATIONS

US 9,951,139 B2, 04/2018, Fertig et al. (withdrawn)

(Continued)

*Primary Examiner* — Robert S Landsman
(74) *Attorney, Agent, or Firm* — Morrison & Foerster LLP

(57) ABSTRACT

The current invention relates to the intermittent dosing of an anti-CSF-1R antibody in combination with macrophage activating agent, corresponding pharmaceutical compositions or medicaments using such combination therapy.

12 Claims, 9 Drawing Sheets

Specification includes a Sequence Listing.

(56) References Cited

U.S. PATENT DOCUMENTS

| | | |
|---|---|---|
| 2002/0141994 A1 | 10/2002 | Devalaraja |
| 2003/0211100 A1 | 11/2003 | Bedian et al. |
| 2004/0006006 A9 | 1/2004 | Armitage |
| 2007/0122378 A1 | 5/2007 | Freeman et al. |
| 2007/0280935 A1 | 12/2007 | Bohrmann et al. |
| 2009/0155164 A1 | 6/2009 | Brasel et al. |
| 2009/0304687 A1 | 12/2009 | Drachman et al. |
| 2009/0317403 A1 | 12/2009 | Aharinejad et al. |
| 2010/0040614 A1 | 2/2010 | Ahmed et al. |
| 2010/0203056 A1 | 8/2010 | Irving et al. |
| 2011/0081353 A1 | 4/2011 | Haegel et al. |
| 2011/0165156 A1 | 7/2011 | Dimoudis et al. |
| 2011/0178278 A1 | 7/2011 | Haegel et al. |
| 2011/0274683 A1 | 11/2011 | Wong et al. |
| 2012/0251531 A1 | 10/2012 | Baehner |
| 2012/0329997 A1 | 12/2012 | Fertig et al. |
| 2013/0005949 A1 | 1/2013 | Fertig et al. |
| 2013/0045200 A1 | 2/2013 | Irving et al. |
| 2013/0045201 A1 | 2/2013 | Irving et al. |
| 2013/0045202 A1 | 2/2013 | Irving et al. |
| 2013/0289250 A1 | 10/2013 | Haegel et al. |
| 2013/0302322 A1 | 11/2013 | Wong et al. |
| 2014/0057972 A1 | 2/2014 | Haegel et al. |
| 2014/0065135 A1 | 3/2014 | Irving et al. |
| 2014/0079699 A1 | 3/2014 | Wong et al. |
| 2014/0079706 A1 | 3/2014 | Cannarile et al. |
| 2014/0120088 A1 | 5/2014 | Carpentier et al. |
| 2014/0205608 A1 | 7/2014 | Steidl et al. |
| 2014/0255417 A1 | 9/2014 | Haegel et al. |
| 2014/0314771 A1 | 10/2014 | Hoves et al. |
| 2014/0336363 A1 | 11/2014 | Fertig et al. |
| 2014/0341902 A1 | 11/2014 | Maecker et al. |
| 2015/0073129 A1 | 3/2015 | Herting et al. |
| 2015/0080556 A1 | 3/2015 | Fertig et al. |
| 2015/0158950 A1 | 6/2015 | Dimoudis et al. |
| 2015/0175696 A1 | 6/2015 | Fertig et al. |
| 2015/0274830 A1 | 10/2015 | Dimoudis et al. |
| 2015/0274831 A1 | 10/2015 | Dimoudis et al. |
| 2015/0322153 A1 | 11/2015 | Irving et al. |
| 2016/0053015 A1 | 2/2016 | Fertig et al. |
| 2016/0220669 A1 | 8/2016 | Hoves et al. |
| 2017/0015752 A1 | 1/2017 | Fertig et al. |
| 2017/0029517 A1 | 2/2017 | Dimoudis et al. |
| 2017/0051065 A1 | 2/2017 | Herting et al. |
| 2017/0114139 A1 | 4/2017 | Fertig et al. |
| 2017/0247459 A1 | 8/2017 | Cannarile et al. |
| 2017/0275368 A1 | 9/2017 | Fertig et al. |
| 2017/0320953 A1 | 11/2017 | Dimoudis et al. |
| 2018/0186883 A1 | 7/2018 | Papadopoulos et al. |
| 2018/0208662 A1 | 7/2018 | Dimoudis et al. |
| 2018/0244788 A1 | 8/2018 | Dimoudis et al. |
| 2018/0346581 A1 | 12/2018 | Herting et al. |
| 2018/0346582 A1 | 12/2018 | Fertig et al. |
| 2019/0071507 A1 | 3/2019 | Dimoudis et al. |
| 2019/0185572 A1 | 6/2019 | Cannarile et al. |
| 2019/0218296 A1 | 7/2019 | Björck et al. |
| 2019/0300614 A1 | 10/2019 | Dimoudis et al. |
| 2019/0309078 A1 | 10/2019 | Cannarile et al. |
| 2020/0392234 A1 | 12/2020 | Herting et al. |
| 2021/0205453 A1 | 7/2021 | Ravuri et al. |

FOREIGN PATENT DOCUMENTS

| | | |
|---|---|---|
| CN | 110636861 A | 12/2019 |
| EP | 0307434 A1 | 3/1989 |
| EP | 0425235 B1 | 9/1996 |
| EP | 0668914 B1 | 8/2000 |
| EP | 1476185 A2 | 11/2004 |
| EP | 2423228 A1 | 2/2012 |
| EP | 2510010 A1 | 10/2012 |
| JP | H0967400 A | 3/1997 |
| JP | 2001523956 A | 11/2001 |
| JP | 2006519163 A | 8/2006 |
| JP | 2008013566 A | 1/2008 |
| JP | 2010512421 A | 4/2010 |
| JP | 2010536378 A | 12/2010 |
| JP | 2011512851 A | 4/2011 |
| JP | 2013513367 A | 4/2013 |
| JP | 2015516369 A | 6/2015 |
| JP | 2016516798 A | 6/2016 |
| JP | 2016531150 A | 10/2016 |
| KR | 20080079301 | 8/2008 |
| RU | 94028282 | 7/1996 |
| RU | 2008132150 A | 2/2010 |
| RU | 2434641 C2 | 11/2011 |
| RU | 2010141584 A | 4/2012 |
| RU | 2478400 C2 | 4/2013 |
| WO | WO198807089 A1 | 9/1988 |
| WO | 199325687 A1 | 12/1993 |
| WO | 199411026 A2 | 5/1994 |
| WO | 199411026 A3 | 8/1994 |
| WO | WO199818810 A1 | 5/1998 |
| WO | 199843089 A1 | 10/1998 |
| WO | 199852976 A1 | 11/1998 |
| WO | 199917798 A1 | 4/1999 |
| WO | WO200107055 A1 | 2/2001 |
| WO | 2001030381 A2 | 5/2001 |
| WO | 2001030381 A3 | 5/2001 |
| WO | WO2001030381 A2 | 5/2001 |
| WO | WO2001030381 A3 | 5/2001 |
| WO | WO2003040170 A2 | 5/2003 |
| WO | WO2003040170 A3 | 10/2003 |
| WO | WO2004045532 A2 | 6/2004 |
| WO | WO2005046657 A2 | 5/2005 |
| WO | WO2005046657 A3 | 11/2005 |
| WO | WO2004045532 A3 | 1/2006 |
| WO | 2006012451 A2 | 2/2006 |
| WO | 2006012451 A3 | 3/2006 |
| WO | WO2006096489 A2 | 9/2006 |
| WO | 2006133396 A2 | 12/2006 |
| WO | WO2006096489 A3 | 3/2007 |
| WO | 2007075326 A2 | 7/2007 |
| WO | 2007081879 A2 | 7/2007 |
| WO | 2007081879 A3 | 9/2007 |
| WO | 2008073959 A2 | 6/2008 |
| WO | 2008083174 A2 | 7/2008 |
| WO | 2007075326 A3 | 9/2008 |
| WO | 2008119493 A1 | 10/2008 |
| WO | 2008073959 A3 | 11/2008 |
| WO | 2008083174 A3 | 12/2008 |
| WO | 2008153926 A2 | 12/2008 |
| WO | WO2009026303 A1 | 2/2009 |
| WO | 2008153926 A3 | 3/2009 |
| WO | 2008153926 A4 | 5/2009 |
| WO | 2006133396 A3 | 8/2009 |
| WO | 2009120903 A2 | 10/2009 |
| WO | WO2009112245 A9 | 11/2009 |
| WO | 2009120903 A3 | 1/2010 |
| WO | 2010077634 A1 | 7/2010 |
| WO | WO2010088395 A2 | 8/2010 |
| WO | WO2010088395 A3 | 11/2010 |
| WO | 2011066389 A1 | 6/2011 |
| WO | WO2011070024 A1 | 6/2011 |
| WO | 2011107553 A1 | 9/2011 |
| WO | 2011117329 A1 | 9/2011 |
| WO | 2011131407 A1 | 10/2011 |
| WO | WO2011123381 A1 | 10/2011 |
| WO | WO2011140249 A2 | 11/2011 |
| WO | 2012068470 A2 | 5/2012 |
| WO | WO2012085291 A1 | 6/2012 |
| WO | WO2012110360 A1 | 8/2012 |
| WO | 2013011021 A1 | 1/2013 |
| WO | 2013019906 A1 | 2/2013 |
| WO | 2013057281 A2 | 4/2013 |
| WO | 2013057281 A3 | 6/2013 |
| WO | 2013079174 A1 | 6/2013 |
| WO | 2013087699 A1 | 6/2013 |
| WO | 2013119716 A1 | 8/2013 |
| WO | WO2011140249 A3 | 8/2013 |
| WO | 2012068470 A3 | 9/2013 |
| WO | 2013135648 A1 | 9/2013 |
| WO | WO2013132044 A1 | 9/2013 |
| WO | 2013169264 A1 | 11/2013 |
| WO | 2014072441 A1 | 5/2014 |

(56) References Cited

FOREIGN PATENT DOCUMENTS

| WO | WO2014173814 A1 | 10/2014 |
|---|---|---|
| WO | WO2015036511 A1 | 3/2015 |
| WO | 2016001160 A1 | 1/2016 |
| WO | WO2016023960 A1 | 2/2016 |
| WO | 2016069727 A1 | 5/2016 |
| WO | 2016081384 A1 | 5/2016 |
| WO | 2016109310 A1 | 7/2016 |
| WO | 2016196935 A1 | 12/2016 |
| WO | 2018115051 A1 | 6/2018 |
| WO | 2018160917 A1 | 9/2018 |

OTHER PUBLICATIONS

US 9,951,140 B2, 04/2018, Fertig et al. (withdrawn)
Agrawal, S. et al. (2007) "Synthetic Agonists of Toll-Like Receptors 7, 8 and 9." Biochemical Society Transactions 35(Pt. 6):1461-1467.
Albert, M.L. et al. (1998). "Dendritic Cells Acquire Antigen From Apoptotic Cells and Induce Class I-Restricted CTLs," Nature 392(6671):86-89.
Alderson, M.R. et al. (1993). "CD40 Expression by Human Monocytes: Regulation by Cytokines and Activation of Monocytes by the Ligand for CD40," J. Exp. Med. 178:669-674.
Altenburg, A. et al. (1999). "CD40 Ligand-CD40 Interaction Induces Chemokines in Cervical Carcinoma Cells in Synergism With IFN-γ," J. Immmol. 162(7):4140-4147.
Armant, M. et al. (1996). "Functional CD40 Ligand Expression on T Lymphocytes in the Absence of T Cell Receptor Engagement: Involvement in Interleukin-2-Induced Interleukin-12 and Interferon-Gamma Production," Eur. J. Immunol. 26(7):1430-1434.
Ashmun, R.A. et al. (1989). "Monoclonal Antibodies to the Human CSF-1 Receptor (c-fms Proto-Oncogene Product) Detect Epitopes on Normal Mononuclear Phagocytes and on Human Myeloid Leukemic Blast Cells," Blood 73 (3):827-837.
ATCC CCL 87—"Jiyoye,", retrieved from <https//www.atcc.org/Products/All/CCL-87.aspx>, last visited Jul. 12, 2019, 3 pages.
Ausubel, F. et al. (1987). Current Protocols in Molecular Biology, Greene Publishing and Wiley Interscience, New York, TOC, 7 pages.
Banchereau, J. et al. (1995). "Functional CD40 Antigen on B Cells, Dendritic Cells and Fibroblasts," Adv. Exp. Med. & Biol. 378:79-83.
Barnes, L.M. et al. (2000). "Advances in Animal Cell Recombinant Protein Production: GS-NS0 Expression System," Cytotechnology 32:109-123.
Barnes, L.M. et al. (2001). "Characterization of the Stability of Recombinant Protein Production in the GS-NS0 Expression System," Biotech. Bioeng. 73:261-270.
Bauer, S. et al. (2001). "Human TLR9 Confers Responsiveness to Bacterial DNA Via Species-Specific CpG Motif Recognition," Proc. Natl. Acad. Sci. USA 98(16):9237-9242.
Bauer, S. et al. (2002). "Bacterial CpG-DNA Licenses TLR9," Current Topics in Microbiology and Immunology 270:145-154.
Beatty, G.L. et al. (2011). "CD40 Agonists Alter Tumor Stroma and Show Efficacy Against Pancreatic Carcinoma in Mice and Humans," Science 331(6024):1612-1616, 9 pages.
Bellovin, D. I. et al. (2015). "Tumor Weight (mean g SEM) Tumor Weight (mean g SEM) cmFPA008, an Anti-Mouse CSF-IR Antibody, Combines with Multiple Immunotherapies to Reduce Tumor Growth in Nonclinical Models", Poster, 1 page.
Bennett, S.R. et al. (1997). "Induction of a CD8+ Cytotoxic T Lymphocyte Response by Cross-Priming Requires Cognate CD4+ T Cell Help," J. Exp. Med. 186(1):65-70.
Bennett, S.R. et al. (1998). "Help for Cytotoxic-T-Cell Responses is Mediated by CD40 Signalling," Nature 393 (6684):478-480.
Bingle, L. et al. (2002). "The Role of Tumour-Associated Macrophages in Tumour Progression: Implications for New Anticancer Therapies," J. Pathol. 196(3):254-265.

Boackle, R.J. et al. (1979). "An IgG Primary Sequence Exposure Theory for Complement Activation Using Synthetic Peptides," Nature 282:742-743.
Boettler, T. et al. (2006). "Expression of the Interleukin-7 Receptor Alpha Chain (CD127) on Virus-Specific CD8+ T Cells Identifies Functionally and Phenotypically Defined Memory T Cells during Acute Resolving Hepatitis B Virus Infection," J. Virol. 80(7):3532-3540.
Bourette, R.P. et al. (2000). "Early Events in M-CSF Receptor Signaling," Growth Factors 17(3):155-166.
Brassard, D.L. et al. (2002). "Interferon-α As an Immunotherapeutic Protein," J Leukoc. Biol. 71(4):565-581.
Brossart, P. et al. (1998). "Generation of Functional Human Dendritic Cells From Adherent Peripheral Blood Vlonocytes by CD40 Ligation in the Absence of Granulocyte-Macrophage Colony-Stimulating Factor," Blood 92 (11):4238-4247.
Brunhouse, R. et al. (1997). "Isotypes of IgG: Comparison of the Primary Structure of Three Pairs of Isotypes which Differ in Their Ability to Activate Complement," J. Mol. Immunol. 16:907-917.
Bryne, K.T. et al. (2016). "CSF-IR-Dependent Lethal Hepatotoxicity When Agonistic CD40 Antibody is Given before but Not after Chemotherapy", J. Immunol. 197(1):179-187, 20 pages.
Buhlmann J.E. et al. (1995). "In the Absence of a CD40 Signal, B Cells are Tolerogenic," Immunity 2:645-653.
Burton, D.R. et al. (1980). "The C1q Receptor Site on Immunoglobulin," Nature 288:338-344.
Butte, M.J. et al. (2007). "Programmed Death-1 Ligand 1 Interacts Specifically with the B7-1 Costimulatory Molecule to Inhibit T Cell Responses," Immunity 27:111-122, 22 pages.
Carbone, E. et al. (1997). "A New Mechanism of NK Cell Cytotoxicity Activation: The CD40—CD40 Ligand Interaction," J. Exp. Med. 185(12):2053-2060.
Carpentier, A.F. et al. (2006). "Phase 1 Trial of a CpG Oligodeoxynucleotide for Patients With Recurrent Glioblastoma," Neuro-Oncology 8(1):60-66.
Carter, L. et al. (2002). "PD-1: PD-L Inhibitory Pathway Affects Both CD4(+) and CD8(+) T Cells and is Overcome by IL-2," Eur. J. Immunol. 32(3):634-643.
Carter, P. et al. (1992). "Humanization of an Anti-p185HER2 Antibody for Human Cancer Therapy," Proc. Natl. Acad. Sci. USA 89:4285-4289.
CAS No. 880486-59-9, retrieved from <https:pubchem.ncbi.nlm.nih.gov/substance/135323347>, last visited Jul. 12, 2019. 3 pages.
Caux, C. et al. (1994). "Activation of Human Dendritic Cells Through CD40 Cross-Linking," J. Exp. Med. 180 (4):1263-1272.
Cella, M. et al. (1996). "Ligation of CD40 on Dendritic Cells Triggers Production of High Levels of Interleukin-12 and Enhances T Cell Stimulatory Capacity: T-T Help Via APC Activation," J. Exp. Med. 184(2):747-752.
Chambers, S.K. (2009). "Role of CSF-1 in Progression of Epithelial Ovarian Cancer," Future Oncol 5(9):1429-1440, 18 pages.
Chaussabel, D. et al. (1999). "CD40 Ligation Prevents Trypanosoma cruzi Infection through Interleukin-12 Upregulation," Infection & Immunity 67(4):1929-1934.
Coffman, R.L. et al. (2010) "Vaccine Adjuvants: Putting Innate Immunity to Work," Immunity 33(4):492-503, 21 pages.
Coussens, L, et al. (1986). "Structural Alteration of Viral Homologue of Receptor Proto-Oncogene fms at Carboxyl Terminus," Nature 320(60659):277-280.
CP-870,893—"CD40 Agonist Monoclonal Antibody CP-870,893," retrieved from <https://www.ncbi.nlm.nih.gov/medgen/?term=CP-870%2C893>, last visited Jul. 12, 2019, 2 pages.
Dai, X.-M. et al. (2002). "Targeted Disruption of the Mouse Colony-Stimulating Factor 1 Receptor Gene Results in Osteopetrosis, Mononuclear Phagocyte Deficiency, Increased Primitive Progenitor Cell Frequencies, and Reproductive Defects," Blood 99(1):111-120.
Dalpke, A.H. et al. (2002). "Phosphodiester CpG Oligonucleotides as Adjuvants: Polyguanosine Runs Enhance Cellular Uptake and Improve Immunostimulative Activity of Phosphodiester CpG Oligonucleotides in vitro and in vivo," Immunology 106(1):102-112.
Deckers, J.G.M. et al. (1998). "IL-4 and IL-13 Augment Cytokine- and CD40-Induced RANTES Production by Human Renal Tubular Epithelial Cells in vitro," J. Am. Soc. Nephrol. 9:1187-1193.

(56) References Cited

OTHER PUBLICATIONS

Denardo, D.G. et al. (2011). "Leukocyte Complexity Predicts Breast Cancer Survival and Functionally Regulates Response to Chemotherapy," Cancer Discovery 1:54-67, 30 pages.
Denardo, D.G. et al. (2009) "CD4+ T Cells Regulate Pulmonary Metastasis of Mammary Carcinomas by Enhancing Protumor Properties of Macrophages," Cancer Cell 16(2):91-102, 24 pages.
Denfeld, R. W. et al. (1996). "CD40 Is Functionally Expressed on Human Keratinocytes," Eur. J. Immunol. 26 (10):2329-2334.
Diehl, L. et al. (1999). "CD40 Activation In Vivo Overcomes Peptide-Induced Peripheral Cytotoxic T-Lymphocyte Tolerance and Augments Anti-Tumor Vaccine Efficacy," Nature Medicine 5(7):774-779.
Donepudi, M. et al. (1999). "Signaling Through CD40 Enhances Cytotoxic T Lymphocyte Generation by CD8+ T Cells From Mice Bearing Large Tumors," Cancer Immunol. Immunother. 48(2-3):153-164.
Dong, H. et al. (1999). "B7-H1, A Third Member of the B7 Family, Co-Stimulates T-Cell Proliferation and Interleukin-10 Secretion," Nature Med. 5(12):1365-1369.
Durocher, Y. et al. (2002). "High-level and High-Throughput Recombinant Protein Production by Transient Transfection of Suspension-Growing Human 293-EBNA1 Cells," Nucl. Acids. Res. 30(2):e9:1-9.
Eppihimer, M.J. et al. (2002). "Expression and Regulation of the PD-L1 Immunoinhibitory Molecule on Microvascular Endothelial Cells," Microcirculation 9(2):133-145, 20 pages.
Ferlin, W.G. et al. (1998). "The Induction of a Protective Response in Leishmania major-Infected BALB/c Mice With Anti-CD40 mAb," Eur. J. Immunol. 28(2):525-531.
Flores-Romo, L. et al. (1997). "CD40 Ligation on Human Cord Blood CD34+ Hematopoietic Progenitors Induces Their Proliferation and Differentiation into Functional Dendritic Cells," J. Exp. Med. 185(2):341-349.
Flores-Romo, L. et al. (1993). "Anti-CD40 Antibody Stimulates the VLA-4-Dependent Adhesion of Normal and LFA-1-Deficient B Cells to Endothelium," Immunol. 79(3):445-451.
Foy, T.M. et al. (1996). "Immune Regulation by CD40 and Its Ligand GP39," Ann. Rev. Immunol. 14:591-617.
Freeman, G.J. et al. (2000, e-pub. Oct. 2, 2000). "Engagement of the PD-1 Immunoinhibitory Receptor by a Novel B7 Family Member Leads to Negative Regulation of Lymphocyte Activation," J. Exp. Med. 192:1027-1034.
French, R.R. et al. (1999). "CD40 Antibody Evokes a Cytotoxic T-Cell Response That Eradicates Lymphoma and Bypasses T-Cell Help," Nature Medicine 5(5):548-553.
Funakoshi, S. et al. (1996). "Differential in vitro and in vivo Antitumor Effects Mediated by Anti-CD40 and Anti-CD20 Monoclonal Antibodies Against Human B-Cell Lymphomas," J. Immunother. Emphasis Tumor Immunol. 19(2):93-101.
Galluzzi, L. et al. (2012). "Trial Watch: Experimental Toll-like Receptor Agonists for Cancer Therapy," OncoImmunology 1(5):699-716.
Geisse, S. et al. (1996). "Eukaryotic Expression Systems: A Comparison," Protein Expr. Purif. 8(3):271-282.
Grammar, A.C. et al. (1998). "TNF Receptor-Associated Factor-3 Signaling Mediates Activation of p38 and Jun N-Terminal Kinase, Cytokine Secretion, and Ig Production Following Ligation of CD40 on Human B Cells," J. Immunol. 161:1183-1193.
Grewal, I.S. et al. (1998). "CD40 and CD154 in Cell-Mediated Immunity," Ann. Rev. Immunol. 16:111-135.
Grewal, I.S. et al. (1996). "Requirement for CD40 Ligand in Costimulation Induction, T Cell Activation, and Experimental Allergic Encephalomyelitis," Science 273(5283):1864-1867.
Grewal, I.S. et al. (1995). "Impairment of Antigen-Specific T-Cell Priming in Mice Lacking CD40 Ligand," Nature 378 (6557):617-620.
Grousson, J. et al. (1998). "Effects of CD40 Ligation on Human Keratinocyte Accessory Function," Archives Dermatol. Res. 290(6):325-330.

Gruss, H.J. et al. (1994). "Expression and Function of CD40 on Hodgkin and Reed-Stemberg Cells and the Possible Relevance for Hodgkin's Disease," Blood 84(7):2305-2314.
Guzman-Montes, G.Y. et al. (2009). "Indirect Patient Expenses for Antituberculosis Treatment in Tijuana, Mexico: is Treatment Really Free?" Clin. Cancer Res. 3(10):778-787.
Heath, A.W. et al. (1994). "Monoclonal Antibodies to Murine CD40 Define Two Distinct Functional Epitopes," Eur. J Immunol. 24(8):1828-1834. Abstract Only.
Heckman, K.L. et al. (2007). "Fast-Tracked CTL: Rapid Induction of Potent Anti-Tumor Killer T Cells in situ," Eur. J. Immunol. 37:1827-1835.
Hemmi, H. et al. (2000). "A Toll-Like Receptor Recognizes Bacterial DNA," Nature 408(6813):740-745.
Hezareh et al. (2001). "Effector function activities of a panel of mutants of a broadly neutralizing antibody against human immunodeficiency virus type 1" J. Virol. 75(24):12161-12168.
Hirano, A. et al. (1999). "Inhibition of Human Breast Carcinoma Growth by a Soluble Recombinant Human CD40 Ligand," Blood 93(9):2999-3007.
Hollenbaugh, D. et al. (1995). "Expression of Functional CD40 by Vascular Endothelial Cells," J. Exp. Med. 182:33-40.
Huang, A.Y. et al. (1994). "Bone Marrow-Derived Cells Present MHC Class I-Restricted Tumour Antigens in Priming of Antitumour Immune Responses," Ciba Foundation Symp. 187:229-244.
Hume, D.A. et al. (2012). "Therapeutic Applications of Macrophage Colony-Stimulating Factor-1 (CSF-1) and Antagonists of CSF-1 Receptor (CSF-1R) Signaling," Blood 119(8):1810-1820.
Idusogie, E.E. et al. (2000). "Mapping of the C1q Binding Site on Rituxan, a Chimeric Antibody With a Human IgG1 Fc," J. Immunol. 164:4178-4184.
International Preliminary Report on Patentability dated Feb. 26, 2019, for PCT Application No. PCT/EP2017/070570, filed Aug. 14, 2017, 9 pages.
International Search Report and Written Opinion dated Oct. 9, 2017, for PCT Application No. PCT/EP2017/070570, filed Aug. 14, 2017, 12 pages.
Ishida, T.K. et al. (1996). "TRAF5, a Novel Tumor Necrosis Factor Receptor-Associated Factor Family Protein, Mediates CD40 Signaling," Proc. Natl. Acad. Sci. USA 93(18):9437-9442.
Jeppson, J.D. et al. (1998). "Requirement for Dual Signals by Anti-CD40 and IL-4 for the Induction of Nuclear Factor-κB, IL-6, and IgE in Human B Lymphocytes," J. Immunol. 161:1738-1742.
Johnson, G. et al. (2000). "Kabat Database and Its Applications: 30 Years After the First Variability Plot," Nucleic Acids Res. 28:214-218.
Jones, K.W. et al. (1996). "Activated T Hybridomas Induce Upregulation of B7-1 on Bystander B Lymphoma Cells by a Contact-Dependent Interaction Utilizing CD40 Ligand," Cellular Immunol. 174(1):42-53.
Kabat, E.A. et al. (1991). Sequences of Proteins of Immunological Interest, 5th ed., Public Health Service, National Institutes of Health, Bethesda, MD. TOC, 21 pages.
Kandimalla, E.R. et al. (2003). "Divergent Synthetic Nucleotide Motif Recognition Pattern: Design and Development of Potent Immunomodulatory Oligodeoxyribonucleotide Agents With Distinct Cytokine Induction Profiles," Nucleic Acids Res. 31(9)2393-2400.
Kandimalla, E.R. et al. (2001). "Effect of Chemical Modifications of Cytosine and Guanine in a CpG-Motif of Oligonucleotides: Structure-Immunostimulatory Activity Relationships," Bioorg. Med. Chem. 9(3):807-813.
Kandimalla, E.R. et al. (2005). "Immunomodulatory Oligonucleotides Containing a Cytosine-Phosphate-2'-Deoxy-7-Deazaguanosine Motif as Potent Toll-Like Receptor 9 Agonists," Proc. Natl. Acad. Sci. USA. 102(19):6925-6930.
Kandimalla, E.R. et al. (2003). "A Dinucleotide Motif in Oligonucleotides Shows Potent Immunomodulatory Activity and Overrides Species-Specific Recognition Observed With CpG Motif," Proc. Natl. Acad. Sci. USA. 100 (24):14303-14308.

(56) References Cited

OTHER PUBLICATIONS

Katada, Y. et al. (1996). "B Cell-B Cell Interaction Through Intercellular Adhesion Molecule-1 and Lymphocyte Functional Antigen-1 Regulates Immunoglobulin E Synthesis by B Cells Stimulated With Interleukin-4 and Anti-CD40 Antibody," Eur. J. Immunol. 26(1):192-200.
Kaufman, R.J. (2000). "Overview of Vector Design for Mammalian Gene Expression," Mol. Biotechnol. 16:151-161.
Kawai, O. et al. (2008, e-pub. Jul. 31, 2008). "Predominant Infiltration of Macrophages and CD8+ T Cells in Cancer Nests is a Significant Predictor of Survival in Stage IV Nonsmall Cell Lung Cancer," Cancer 6:1387-1395.
Kawai, T. et al. (2010, e-pub. Apr. 20, 2010). "The Role of Pattern-Recognition Receptors in Innate Immunity: Update on Toll-Like Receptors," Nature Immunol. 11(5):373-384.
Kawamura, K. et al. (2009). "Detection of M2 Macrophages and Colony-Stimulating Factor 1 Expression in Serous and Mucinous Ovarian Epithelial Tumors," Pathol. Int. 59(5):300-305.
Keir, M.E. et al. (2008, e-pub. Jan. 2, 2008). "PD-1 and Its Ligands in Tolerance and Immunity," Annu. Rev. Immunol. 26:677-704.
Khalil, M. et al. (2007). "Anti-CD40 Agonist Antibodies: Preclinical and Clinical Experience," Update Cancer Ther.; 2 (2):61-65, 9 pages.
Kiener, P.A. et al. (1995). "Stimulation of CD40 With Purified Soluble gp39 Induces Proinflammatory Responses in Human Monocytes," J. Immunol. 155(10):4917-4925.
Kitaura, H. et al. (2008). "An Anti-c-Fms antibody Inhibits Orthodontic Tooth Movement," J. Dental Res. 87 (4):396-400.
Koch, F. et al. (1996). "High Level IL-12 Production by Murine Dendritic Cells: Upregulation Via MHC Class II and CD40 Molecules and Downregulation by IL-4 and IL-10," J. Exp. Med. 184(2):741-746.
Krug, A. et al. (2001). "Identification of CpG Oligonucleotide Sequences With High Induction of IFN-α/β in Plasmacytoid Dendritic Cells," Eur. J. Immunol., 31(7):2154-2163.
Kuipers, H. et al. (2006). "Contribution of the PD-1 Ligands/PD-1 Signaling Pathway to Dendritic Cell-Mediated CD4+ T Cell Activation," Eur. J. Immunol. 36(9):2472-2482.
Kuniyoshi, J.S. et al. (1999). "Dendritic Cell Secretion of IL-15 is Induced by Recombinant huCD40LT and Augments the Stimulation of Antigen-Specific Cytolytic T Cells," Cellular Immunol. 193(1):48-58.
Langmead, B. et al. (2012) "Fast Gapped-Read Alignment With Bowtie 2," Nat Methods 9(4):357-359, 8 pages.
Latchman, Y. et al. (2001). "PD-L2 is a Second Ligand for PD-1 and Inhibits T Cell Activation," Nature Immunol. 2 (3):261-268.
Latchman, Y.E. et al. (2004). "PD-L1-Deficient Mice Show That PD-L1 on T Cells, Antigen-Presenting Cells, and Host Tissues Negatively Regulates T Cells," Proc. Natl. Acad. Sci. USA 101(29):10691-10696.
Lazaar, A.L. et al. (1998). "CD40-Mediated Signal Transduction in Human Airway Smooth Muscle," J. Immunol. 161:3120-3127.
Lee, H.H. et al. (1999). "Specificities of CD40 Signaling: Involvement of TRAF2 in CD40-Induced NF-κB Activation and Intercellular Adhesion Molecule-1 Up-Regulation," Proc. Natl Acad. Sci. USA 96(4):1421-1426.
Lee, P.S.W. et al. (1999). "The Cbl Protooncoprotein Stimulates CSF-1 Receptor Multiubiquitination and Endocytosis, and Attenuates Macrophage Proliferation," EMBO J. 18(13):3616-3628.
Lee, S.J. et al.(2006, e-pub. Jan. 9, 2006). "Interferon Regulatory Factor-1 is Prerequisite to the Constitutive Expression and IFN-γ-Induced Upregulation of B7-H1 (CD274)," FEBS Lett. 580(3):755-762.
Lenda, D.M. et al. (2003). "Reduced Macrophage Recruitment, Proliferation, and Activation in Colony-Stimulating Factor-1-Deficient Mice Results in Decreased Tubular Apoptosis During Renal Inflammation," J. Immunol. 170:3254-3262.
Li, F. et al. (2011). "Inhibitory Fcγ Receptor Engagement Drives Adjuvant and Anti-Tumor Activities of Agonistic CD40 Antibodies,"Science 333(6045):1030-1034, 13 pages.
Li, W. et al. (1991). "Role of Dimerization and Modification of the CSF-1 Receptor in Its Activation and Internalization During the CSF-1 Response," EMBO J. 10(2):277-288.
Liang, S.C. et al. (2003). "Regulation of PD-1, PD-L1, and PD-L2 Expression During Normal and Autoimmune Responses," Eur. J. Immunol. 33(10): 2706-2716.
Liang, X. et al. (2010, e-pub. Mar. 25, 2010). "Toll-like Receptor 9 Signaling by CpG-B Oligodeoxynucleotides Induces an Apoptotic Pathway in Human Chronic Lymphocytic Leukemia B Cells," Blood 115(24):5041-5052.
Lin, E.Y. et al. (2001). "Colony-Stimulating Factor 1 Promotes Progression of Mammary Tumors to Malignancy," J. Exp. Med. 193(6):727-740.
Lin, H. et al. (2008). "Discovery of a Cytokine and Its Receptor by Functional Screening of the Extracellular Proteome," Science 320(5877):807-811.
Liu, J. et al. (2007). "Plasma Cells From Multiple Myeloma Patients Express B7-H1 (PD-L1) and Increase Expression After Stimulation With IFN-γ and TLR Ligands Via a MyD88-, TRAF6-, and MEK-Dependent Pathway," Blood 110 (1):296-304.
Loke, P. et al. (2003). "PD-L1 and PD-L2 are Differentially Regulated by Th1 and Th2 Cells," Proc. Natl Acad. Sci. USA 100(9):5336-5341.
Longhi, M.P. et al. 2009). "Dendritic Cells Require a Systemic Type I Interferon Response to Mature and Induce CD4+ Th1 Immunity With Poly IC as Adjuvant," J. Exp. Med. 206(7):1589-1602.
Lukas, T.J. et al. (1981). "Inhibition of C1-Mediated Immune Hemolysis by Monomeric and Dimeric Peptides From the Second Constant Domain of Human immunoglobulin G," J. Immunol. 127(6):2555-2560.
Mackey, M.F. et al. (1998). "Cutting Edge: Dendritic Cells Require Maturation via CD40 to Generate Protective Antitumor Immunity," J. Immunol. 161:2094-2098.
Mackey, M.F. et al. (1998). "The Role of CD40/CD154 Interactions in the Priming, Differentiation, and Effector Function of Helper and Cytotoxic T Cell," J. Leukocyte Biol. 63(4):418-428.
Mackey, M.F. et al. (1997). "Protective Immunity Induced by Tumor Vaccines Requires Interaction between CD4OandIts Ligand, CD154," Cancer Research 57:2569-2574.
Mahl, R.S. et al. (2013, e-pub. Sep. 2, 2013). "Sweeten PAMPs: Role of Sugar Complexed PAMPs in Innate Immunity and Vaccine Biology," Front. Immunol. 4:248.
Makrides, S.C. (1999). "Components of Vectors for Gene Transfer and Expression in Mammalian Cells," Protein Expr. Purif. 17(2):183-202.
Mantovani, A et al. (2004, e-pub. May 19, 2004). "Tumour-Associated Macrophages as a Prototypic Type II Polarised Phagocyte Population: Role in Tumour Progression," Eur. J. Cancer 40(11):1660-1667.
Mantovani, A. et al. (2010, e-pub. Feb. 9, 2010). "Macrophages, Innate Immunity and Cancer: Balance, Tolerance, and Diversity," Curr. Opin. Immunol. 22(2):231-237.
Martin-Fontecha, A. et al. (1999). "Triggering of Murine NK Cells by CD40 and CD86 (B7-2)," J. Immunol. 162:5910-5916.
Martinez, F.O. et al. (2013). "Genetic Programs Expressed in Resting and IL-4 Alternatively Activated Mouse and Human Macrophages: Similarities and Differences," Blood 21(9):e57-e69.
Mayumi, M. et al. (1995). "Session II: Allergy and Intracellular Signal Transmission Mechanisms: Role of LFA-1/ICAM-1-Dependent Cell Adhesion in CD40-Mediated Inhibition of Anti-IgM Antibody-Induced B-Cell Death," J. Allergy & Clin. Immunol. 96(6 Pt. 2):1136-1144.
Mcdyer, J.F. et al. (1999). "Differential Effects of CD40 Ligand/Trimer Stimulation on the Ability of Dendritic Cells to Replicate and Transmit HIV Infection: Evidence for CC-Chemokine-Dependent and -Independent Mechanisms," J. Immunol. 162:3711-3717.
Meng, Y. et al. (2005). "Successful Combination of Local CpG-ODN and Radiotherapy in Malignant Glioma," Int. J. Cancer 116(6):992-997.
Morgan, A. et al. (1995). "The N-Terminal End of the CH2 Domain of Chimeric Human IgG1 Anti-HLA-DR is Necessary for C1q, FcγRI and FcγRIII Binding," Immunology 86(2):319-324.

(56) References Cited

OTHER PUBLICATIONS

Mortazavi, A. et al. (2008, e-pub. May 30, 2008). "Mapping and Quantifying Mammalian Transcriptomes by RNA-Seq," Nat. Methods 5(7):621-628.
Nielsen, C. et al. (2005. e-pub. Sep. 19, 2005). "Alternative Splice Variants of the Human PD-1 Gene," Cell. Immunol. 235(2):109-116.
Nishimura, H. et al. (2001). "Autoimmune Dilated Cardiomyopathy in PD-1 Receptor-Deficient Mice," Science 291 (5502)319-322.
Nishimura, H. et al. (1999). "Development of Lupus-Like Autoimmune Diseases by Disruption of the PD-1 Gene Encoding an ITIM Motif-Carrying Immunoreceptor," Immunity 11(2):141-151.
Vishimura, H. et al. (1996). "Developmentally Regulated Expression of the PD-1 Protein on the Surface of Double-Negative (CD4−CD8−) Thymocytes," Int. Immunol. 8(5):773-780.
Noelle, R.J (1998). "CD40 and Its Ligand in Cell-Mediated Immunity," Agents & Actions Suppl. 49:17-22.
Norderhaug, L. et al. (1997). "Versatile Vectors for Transient and Stable Expression of Recombinant Antibody Molecules in Mammalian Cells," J. Immunol. Methods 204(1):77-87.
Orlandi, R. et al. (1989). "Cloning Immunoglobulin Variable Domains for Expression by the Polymerase Chain Reaction," Proc. Natl. Acad. Sci. USA 86(10):3833-3837.
Orre, M. et al. (1999). "Macrophages and Microvessel Density in Tumors of the Ovary," Gynecol. Oncol. 73 (1):47-50.
Parsa, A.T. et al. (2007, e-pub. Dec. 20, 2006). "Loss of Tumor Suppressor PTEN Function Increases B7-H1 Expression and Immunoresistance in Glioma," Nat. Med. 13(1):84-88.
Paulie, S. et al. (1985). "A p50 Surface Antigen Restricted to Human Urinary Bladder Carcinomas and B Lymphocytes," Cancer Immunol. Immunother. 20(1):23-28.
Pixley, F.J. et al. (2004). "CSF-1 Regulation of the Wandering Macrophage: Complexity in Action," Trends Cell Biol. 14(11):628-638.
Pollard, J.W. (1997). "Role of Colony-Stimulating Factor-1 in Reproduction and Development," Mol. Reprod. Dev. 46(1):54-61.
Price, F. et al. (1993). "Colony-Stimulating Factor-1 in Primary Ascites of Ovarian Cancer is a Significant Predictor of Survival," Am. J. Obstet. Gynecol. 168(2):520-527.
Pullen S.S. et al. (1999). "CD40 Signaling through Tumor Necrosis Factor Receptor-associated Factors (TRAFs)," J. Biol. Chem. 274(20):14246-14254.
Pullen, S.S. et al. (1998). "CD40—Tumor Necrosis Factor Receptor-Associated Factor (TRAF) Interactions: Regulation of CD40 Signaling Through Multiple TRAF Binding Sites and TRAF Hetero-Oligomerization," Biochemistry 37(34)11836-11845.
Putta, M.R. et al. (2006, e-pub. Jun. 23, 2006). "Novel Oligodeoxynucleotide Agonists of TLR9 Containing N3-Me-dC or N1-Me-dG Modifications," Nucleic Acids Res. 34(11):3231-3238.
Richmann, L.P. et al. (2013, e-pub. Nov. 5, 2013). "Role of Crossliniking for Agonistic CD40 Monoclonal Antibodies as Immune Therapy of Cancer," Cancer Immunology Research, 2:19-26.
Roth, P. et al. (1992). "The Biology of CSF-1 and Its Receptor," Curr. Top. Microbiol. Immunol. 181:141-167.
Rothenfusser, S. et al. (2002). "Plasmacytoid Dendritic Cells: The Key to CpG," Human Immunology 63 (12):1111-1119.
Roussel, M.F. et al. (1987). "Transforming Potential of the c-fms Proto-Oncogene (CSF-1 Receptor)," Nature 325 (6104):549-552.
Roy, M. et al. (1995). "Studies on the Interdependence of gp39 and B7 Expression and Function During Antigen-Specific Immune Responses," Eur. J. Immunol. 25(2):596-603.
Ruggiero, G. et al. (1996). "CD40 Expressed on Thymic Epithelial Cells Provides Costimulation for Proliferation but Not for Apoptosis of Human Thymocytes," J. Immunol. 156(10):3737-3746.
Sandmann, T. et al. (2014, e-pub. Oct. 15, 2013). "gCMAP: User-Friendly Connectivity Mapping With R," Bioinformatics 30(1):127-128.
Santos-Argumedo, L. et al. (1994). "Antibodies to Murine CD40 Protect Normal and Malignant B Cells From Induced Growth Arrest," Cellular Immunol. 156(2):272-285.

Schaniel, C. et al. (1998). "Activated Murine B Lymphocytes and Dendritic Cells Produce a Novel CC Chemokine which Acts Selectively on Activated T Cells," J. Exp. Med. 188(3):451-463.
Schlaeger, E.-J. (1996). "The Protein Hydrolysate, Primatone RL, is a Cost-Effective Multiple Growth Promoter of Mammalian Cell Culture in Serum-Containing and Serum-Free Media and Displays Anti-Apoptosis Properties," J. Immunol. Methods 194(2):191-199.
Schlaeger, E.-J. et al. (1999). "Transient Gene Expression in Mammalian Cells Grown in Serum-Free Suspension Culture," Cytotechnology 30(1-3):71-83.
Schmieder, A. et al. (2012, e-pub. Feb. 13, 2012). "Differentiation and Gene Expression Profile of Tumor-Associated Macrophages," Semin. Cancer Biol. 22(4):289-297.
Schoenberger, S.P. et al. (1998). "T-Cell Help for Cytotoxic T Lymphocytes is Mediated by CD40-CD40L Interactions," Nature 393(6684):480-483.
Scholl, S. et al. (1994). "Circulating Levels of Colony-Stimulating Factor 1 as a Prognostic Indicator in 82 Patients With Epithelial Ovarian Cancer," Br. J. Cancer 62:342-346.
Schreiner, B. et al. (2004). "Interferon-Beta Enhances Monocyte and Dendritic Cell Expression of B7-H1 (PD-L1), A Strong Inhibitor of Autologous T-Cell Activation: Relevance for the Immune Modulatory Effect in Multiple Sclerosis," J. Neuroimmunol. 155(1-2):172-182.
Schroder, K. et al. (2007). "PU.1 and ICSBP control constitutive and IFN-γ-regulated Tlr9 Gene Expression in Mouse Macrophages," J. Leukoc. Biol. 81(6)1577-1590.
Sherr, C.J. et al. (1985). "The c-fms Proto-Oncogene Product is Related to the Receptor for the Mononuclear Phagocyte Growth Factor, CSF-1," Cell 41(3):665-676.
Sotomayor, E.M. et al. (1999). "Conversion of Tumor-Specific CD4+ T-Cell Tolerance to T-Cell Priming Through in vivo Ligation of CD40", Nature Medicine 5(7):780-787.
Stanley, E.R. et al. (1983). "CSF-1—A Mononuclear Phagocyte Lineage-Specific Hemopoietic Growth Factor," J. Cell. Biochem. 21(2):151-159.
Stanley, E.R. et al. (1994). "The Biology and Action of Colony Stimulating Factor-1," Stem Cells 12(Suppl. 1):15-25.
Stanley, E.R. et al. (1997). "Biology and Action of Colony-Stimulating Factor-1," Mol. Reprod. Dev. 46(1):4-10.
Steidl, C. et al. (2010). "Tumor-Associated Macrophages and Survival in Classic Hodgkins's Lymphoma," N. Engl. J. Med. 362(10):875-885.
Steinhagen, F. et al. (2011, e-pub. Aug. 14, 2011). "TLR-Based Immune Adjuvants," Vaccine 29(17):3341-3355, 33 pages.
Subramanian, A. et al. (2005). "Gene Set Enrichment Analysis: A Knowledge-Based Approach for Interpreting Genome-Wide Expression Profiles," Proc. Natl. Acad. Sci. USA 102(43):15545-15550.
Sutherland, C.L et al. (1999). "An 11-Amino Acid Sequence in the Cytoplasmic Domain of CD40 is Sufficient for Activation of c-Jun N-Terminal Kinase, Activation of MAPKAP Kinase-2, Phosphorylation of IkBa, and Protection of WEHI-231 Cells from Anti-IgM-Induced Growth Arrest," J. Immunol. 162:4720-4730.
Séguin, R. et al. (1999). "Sensitized Lymphocytes and CD40 Ligation Augment Interleukin-12 Production by Human Dendritic Cells in Response to Toxoplasma gondii," J. Infect. Dis. 179(2):467-474.
Thommesen, J.E. et al. (2000). "Lysine 322 in the Human IgG3 C(H)2 Domain is Crucial for Antibody Dependent Complement Activation," Mol. Immunol. 37(16):995-1004.
Toes, R.E.M. et al. (1998). "CD40-CD40 Ligand Interactions and Their Role in Cytotoxic T Lymphocyte Priming and Anti-Tumor Immunity," Sem. Immunol. 10(6):443-448.
Tseng, S.-Y. et al. (2001). "B7-Dc, A New Dendritic Cell Molecule with Potent Costimulatory Properties for T Cells," J. Exp. Med. 193(7):839-846.
Tsukamoto, N. et al. (1999). "Two Differently Regulated Nuclear Factor κB Activation Pathways Triggered by the Cytoplasmic Tail of CD40," Proc. Natl. Acad. Sci. USA 96(4):1234-1239.
Tutt, A.L. et al. (1998). "Monoclonal Antibody Therapy of B Cell Lymphoma: Signaling Activity on Tumor Cells Appears More Important Than Recruitment of Effectors," J. Immunol. 161:3176-3185.

(56) References Cited

OTHER PUBLICATIONS

Ueda, H. et al. (2003, e-pub. Apr. 30, 2003). "Association of the T-Cell Regulatory Gene CTLA4 With Susceptibility to Autoimmune Disease," Nature 423(6939):506-511.
Jejima, Y. et al. (1996). "Effect of Interleukin-10 on Anti-CD40- and Interleukin-4-Induced Immunoglobulin E Production by Human Lymphocytes," Int. Arch. of Allergy & Immunol. 110(3):225-232.
Von Leoprechting, A. et al. (1999). "Stimulation of CD40 on Immunogenic Human Malignant Melanomas Augments Their Cytotoxic T Lymphocyte-mediated Lysis and Induces Apoptosis," Cancer Res. 59:1287-1294.
Vonderheide, R.H. et al. (2007). "Clinical Activity and Immune Modulation in Cancer Patients Treated With CP-870,893, A Novel CD40 Agonist Monoclonal Antibody," J. Clin. Oncol. 25(7):876-883.
Waltenbaugh, C. et al. (2008). Immunology Lippincott's Illustrated Reviews. Philadelphia: Wolters Kluwer Health/Lippincott's Williams & Wilkins. p. 17, 5 pages.
Wan, B. et al. (2006). "Aberrant Regulation of Synovial T Cell Activation by Soluble Costimulatory Molecules in Rheumatoid Arthritis," J. Immunol. 177:8844-8850.
Wang, Z., et al. (1993). "identification of the Ligand-Binding Regions in the Macrophage Colony-Stimulating Factor Receptor Extracellular Domain," Mol. Cell. Biol. 13(9):5348-5359.
Weiner, G.J. et al. (1997). "Immunostimulatory Oligodeoxynucleotides Containing the CpG Motif are Effective as Immune Adjuvants in Tumor Antigen Immunization," Proc. Natl. Acad. Sci. USA 94(20):10833-10837.
Werner, R.G. et al. (1998). "Appropriate Mammalian Expression Systems for Biopharmaceuticals," Arzneimittelforschung 48:870-880.
West, R.B. et al. (2006). "A Landscape Effect in Tenosynovial Giant-Cell Tumor From Activation of CSF1 Expression by a Translocation in a Minority of Tumor Cells," Proc. Natl. Acad. Sci. USA 103(3):690-695.
White A.L. et al. (2011, e-pub. Jul. 8, 2011). "Interaction with FcgammaRIIB is Critical for the Agonistic Activity of Anti-CD40 Monoclonal Antibody," J. Immunol. 187(4):1754-1763.
Wyckoff, J.B. et al. (2007). "Direct Visualization of Macrophage-Assisted Tumor Cell Intravasation in Mammary Tumors," Cancer Res. 67(6):2649-2656.
Xiong, Y. et al.(2011). "A CSF-1 Receptor Phosphotyrosine 559 Signaling Pathway Regulates Receptor Ubiquitination and Tyrosine Phosphorylation," J. Biol. Chem. 286(2):952-960.
Yamazaki, T. et al. (2002). "Expression of Programmed Death 1 Ligands by Murine T Cells and APC1," J. Immunol. 169:5538-5545.
Yellin, M.J. et al. (1995). "Ligation of CD40 on Fibroblasts Induces CD54 (ICAM-1) and CD106 (VCAM-1) Up-Regulation and IL-6 Production and Proliferation," J. Leukocyte Biol. 58(2):209-216.
Yeung, Y.-G. et al. (2003). "Proteomic Approaches to the Analysis of Early Events in Colony-stimulating Factor-1 Signal Transduction," Mol. Cell. Proteomics 2:1143-1155.
Zhong, X. et al. (2007). "PD-L2 Expression Extends Beyond Dendritic Cells/Macrophages to B1 Cells Enriched for VH11/VH12 and Phosphatidylcholine Binding," Eur. J. Immunol. 37(9):2405-2410.
Ries et al., "CSF-1/CSF-1R targeting agents in clinical development for cancer therapy" Current Opinion in Pharmacology 23:45-51 (2015).
Sica et al., "Macrophage Plasticity and Polarization in Liver Homeostasis and Pathology" Hepatology 59(5):2035-2043 (Nov 5, 2014).
Abu-Duhier, F.M. et al. (2003). "Mutational Analysis Of Class III Receptor Tyrosine Kinases (C-KIT, C-FMS, FLT3) In Idiopathic Myelofibrosis," Br. J. Haematol. 120(3):464-470.
Aflymetrix Ebioscience. (2000-2014). "Anti-Mouse CD115 (c-fms) Purified," located at httg://www.ebiosciencecom/mouse-cd115-antibody-purified-afs98.htm, last visited on Mar. 26, 2015, 1 page.

Aharinejad, S. et al. (2004). "Colony-Stimulating Factor-1 Blockade By Antisense Oligonucleotides and Small Interfering RNAs Suppresses Growth of Human Mammary Tumor Xenografts in Mice," Cancer Res 64(15):5378-5384.
Anonymous (1988). "Macrophage Colony-Stimulating Factor 1 Receptor (P07333),", 36 pages.
Anonymous (1988). "MCSF Receptor Antibody (AB 10676),", 2 pages.
Anonymous (2016). "NCT02452424: A Combination Clinical Study of PLX3397 and Pembrolizumab To Treat Advanced Melanoma and Other Solid Tumors," pp. 1-7.
Anonymous. (2016). "NCT02323191 : A Study of Emactuzumab (R05509554) and (MPDL3280A) Administered in Combination in Patients With Advanced Solid Tumors," pp. 1-5. MPDL3280A Administered in Combination in Patients With Advanced Solid Tumors, pp. 1-5.
Baker, A.H. et al. (1993). "Expression of The Colony-Stimulating Factor 1 Receptor in B Lymphocytes," Oncogene 8(2):371-378.
Balkwill, F. (2006, e-pub. Sep. 2, 2006). "TNF-α In Promotion and Progression Of Cancer," Cancer Metastasis Rev. 25:409-416.
Balkwill, R. et al. (2005), "Smoldering and Polarized Inflammation in The Initiation and Promotion Of Malignant Disease," Cancer Cell 7(3):211-217.
Beiboer, S.H.W. et al. (2000). "Guided selection of a pan carcinoma specific antibody reveals similar binding characteristics yet structural divergence between the original murine antibody and its human equivalent," J Mol Biol. 296(3):833-849.
Boerner, P. et al. (1991). "Production of a Antigen-Specific Human Monoclonal Antibodies from in Vitro-Primed Human Splenocytes," J. Immunol. 147(1):86-95.
Bonelli, S. et al. (2017). "Beyond the M-CSF Receptor—Novel Therapeutic Targets in i umor-Associated Macrophages," FEBS J. 285(4): 777-787.
Bonham et al. (2009). "Antagonistic Antibodies To c-fms Block c-fms-Mediated Activities Reduce Tumor-Associated Macrophages and Decrease Tumor Growth in Preclinical Models," in Proc Am Assoc Cancer Res 50:503, Abstract #2077, 1 page.
Brahmer et al. (2012). "Safety and Activity of anti-PD-L1 Antibody in Patients With Advanced Cancer," N Engl J Med 366(26): 2455-2465.
Bretscher, P. et al. (1970). "A Theory of Self-Nonself Discrimation," Science 169:1042-1049.
Bretscher, P.A. (1999). "A Two-Step, Two-Signal Model for the Primary Activation of Precursor Helper T Ceils," Proc. Natl. Acad. Sci. USA, 96:185-190.
Bristol-Myers Squibb Cinical Trial (2009). "Multiple Ascending Dose (MDX1105-01) (Anti-PDL1)," retrieved from https://clinicaitrials.gov/ct2/show/NCT00729664 lasted visited on Aug. 10, 2021, 8 pages.
Brodská, B. et al., (2016, e-pub. Aug. 19, 2016). "Correlation of PD-L1 Surface Expression on Leukemia Cells With the Ratio of PD-L1 mRNA Variants and With Electrophoretic Mobility," Cancer Immunol. Res. 4(10):815-819.
Brown, M. et al. (1996) "Tolerance to Single, but Not Multiple, Amino Acid Replacements in Antibody VH CDR2," J. Immunol. 156:3285-3291.
Brüggemann, M. et al. (1993). "Designer Mice: The Production of Human Antibody Repertoires in Transgenic Animals," Year in Immuno. 7:33-40.
Burmester, G.R., et al. (2011). "Mavrilimumab, A. Human Monoclonal Antibody Targeting GM-CSF Receptor[alpha], In Subjects With Rheumatoid Arthritis: A Randomised, Double-Blind, Placebo-Controlled, Phase 1, First-In-Human Study," Ann Rheum Dis. 70(9): 1542-1549.
Caldas, C. et al. (May 2003). "Humanization Of The Anti-CD-18 Antibody 6.7: An Unexptected Effect Of A Framework Residue In Binding To Antigen," Mol. Immunol. 39(15):941 -952.
Callahan, M.K. et al. (2013), "At the Bedside: CTLA-4-and PD-1-Blocking Antibodies in Cancer Immunotherapy," J. Leukoc, Biol. 94:41-53.

(56) References Cited

OTHER PUBLICATIONS

Campbell, I. K et al. (2000). "The Colony-Stimulating Factors and Collagen-Induced Arthritis: Exacerbation Of Disease By M-CSF and G-CSF and Requirement For Endogenous M-CSF," J. Leukoc. Biol. 68:144-150.
Gasset, F. et al. (2003) "A Peptide Mimetic Of An Anti-CD4 Monoclonal Antibody By Rational Design," BBRC 307:198-205.
Cenci, S. et al. (2000). "M-CSF Neutralization and Egr-1 Deficiency Prevent Ovariectomy-Induced Bone Loss," J. Clin. Invest. 105(9):1279-1287.
Chari, R.V.J. et al. (1992). "Immunoconjugates Containing Noveal maytansinoids: Promising Anticancer Drugs," Cancer Res. 52:127-131.
Chase, A. et al. (2009, e-pub. Oct. 30, 2008). "Imatinib Sensitivity As A Consequence Of A CSF1R-Y571D Mutation and CSF1/CSF1 R Signaling Abnormalities In The Cell Line GDM1" Leukemia 23(2):358-364.
Chin, L.-T. et al. (2008). "Immune Intervention With Monoclonal Antibodies Targeting CD152 (CTLA-4) for Autoimmune and Malignant Diseases," Chang Gung Med. J. 31 (1):1-15.
Choueiri, M.B. et al. (2006). "The Central Role Of Osteoblasts In The Metastasis Of Prostate Cancer," Cancer Metastasis Rev. 25:601-609.
Clinicaltrials.gov NCT02323191 (2014). "A Study of Emactuzumab and Atezolizumab Administered in Combination in Participants With Advanced Solid Tumors," 10 pages.
Cole, S.P.C. et al. (1985). "The EBV-Hybridoma Technique and Its Appiicaton to Human Lung Cancer," in Monoclonal Antibodies and Cancer Therapy, Alan R. Liss, p. 77-96.
Da Costa, C.E. et al. (2005). "Presence Of Osteoclast-Like Muitinucieated Giant Cells In The Bone and Nonostotic Lesions Of Langerhans Cell Histiocytosis," J. Exp. Med. 201 (5):687-693.
Damiano, V. et al. (2006). "Novel Toll-Like Receptor 9 Agonist Induces Epidermal Growth Factor Receptor (EGFR) Inhibition and Synergistic Antitumor Activity With EGFR Inhibitors," Clin. Cancer Res. 12(2):577-583.
Daroszewska, A. et al. (2006). "Mechanisms of Disease: Genetics of Paget's Disease of Bone and Related Disorders," Nat. Clin. Pract. Rheumatol. 2(5):270-277.
Davies, J. et al. (1996). "Affinity Improvement Of Single Antibody VH Domains: Residues in All Three Hypervariabie Regions Affect Antigen Binding," Immunol. 2:169-179.
De Palma, M. et al. (2013). "Macrophage Regulation of Tumor Responses to Anticancer Therapies" Cancer Cell 23 K3):277-286.
Denardo, D.G. et al., (2011). "Leukocyte Complexity Predicts Breast Cancer Survival An Dfunctionally Regulates Response To Chemotherapy," Cancer Research 1(1):1-14.
Dewar, A.L. et al. (2005). "Macrophage Colony-Simulating Factor Receptor c-fms Is a Novel Target of Imatinib," Blood, 105(8):3127-3132.
Dhupkar, P. et al. (2018). "Anti-PD-1 Therapy Redirects Macrophages From an M2 to An M1 Phenotype inducting Regression of OS Lung Metastases," Cancer Med. 7(6):2654-2664.
Drees, P. et al. (2007). "Mechanisms of Disease: Molecular Insights Into Aseptic Looseing Of Orthopedic Implants," Nat. Clin. Pract. Rheumatol. 3(3):165-171.
Dubowchik, G.M. et al., (2002), "Doxorubicin Immunoconjugates Containing Bivalent, Lysosomally-Cleavabie Dipeptide Linkages," Bioorganic & Medicinal ChemistryLetters 12:1529-1532.
English Translation of Notification of Reasons for Rejection for Japanese Patent Application No. 2012-542522, dated Feb. 25, 2014 (3 pages}.
Espinosa, I. et al. (2009). "Coordinate Expression of Colony-Stimulating Factor-1 and Colony-Stimulating Factor-1-Related Proteins Is Associated with Poor Prognosis in Gynecological and Nongynecoiogicai Leiomyosarcoma," Am. J. Pathol. 174(6):2347-2356.
European Search Report for Application No. EP 09007224.0 pp. 1-9 (Nov. 24, 2009).

European Search Report for Application No. EP 09015310 pp. 1-8 (Sep. 20, 2010).
Extended Search Report for European Patent Application No. EP 12158519.4, dated Aug. 2, 2012 (8 pages).
Feldstein, A.C. et al. (2005). "Practice Patterns In Patients At Risk For Glucocorticoid-Induced Osteoporosis," Osteoporos. Int. 16:2168-2174.
Flatman, S. et al. (2007, e-pub. Dec. 11, 2006). "Process Analytics for Purification of Monoclonal Antibodies," J. Chromatogr. B. 848:79-87.
Flick, M.B. et al. (1997). "Recognition of Activated CSF-1 Receptor In Breast Carcinomas By a Tyrosine 723 Phosphospecific Antibody," Oncogene 14:2553-2561.
Genentech. "Our Pipeline," retrieved from https://www.gene.com/medical-professionais/pipeline, last visited Aug. 10, 2021, 7 pages.
Gordon, M.S. et al. (2013). "Abstract. LB-288: A Phase I Study of MPDL3280A, An Engineered PD-L1 Antibody In Patients With Locally Advanced Or Metastatic Tumors," Proceedings: AACR 104th Annual Meeting 2013, 4 pages.
Guo, Z. et al. (2015). "Combined Trabectedin and Anti-PD1 Antibody Produces a Synergistic Antitumor Effect in a Murine Model of Ovarian Cancer," J. Transl. Med. 13(247):1-13.
Guzman-Clark, J.R. et al. (2007). "Barriers in the Management of Glucocorticoid-Induced Osteoporosis," Arthritis Rheum. 57(1):140-146.
Haegel, H. et al. (2013, e-pub. Jul. 15, 2013). "A Unique Anti-CD115 Monoclonal Antibody Which Inhibits Osteolysis and Skews Human Monocyte Differentiation From M2-Polarized Macrophages Toward Dendritic Cells," mAbs 5 (5):736-747.
Hamilton, J.A. (2008). "Colony-Stimulating Factors In Inflammation and Autoimmunity," Nat Rev Immunol.8 (7):533-544.
Hao, A.-J. et al., (2002), "Expression Of Macrophage Colony-Stimulating Factor And Its Receptor In Microglia Activation Is Linked To Teratogen-Induced Neuronal Damage," Neuroscience 112(4):889-900.
Haran-Ghera, N. et al. (1997)., "Increased Circulating Colony-Stimulating Factor-1 (CSF-1) in SJL/J Mice Eith Radiation-Induced Acute Myeloid Leukemia (AML) is Associated With Autocrine Regulation of AML Cells By CSF-1," The American Society of Hematology 89(7):2537-2545.
Hayashi, S.-I. et al. (1997). "Osteoclast Precursors in Bone Marrow and Peritoneal Cavity," J. Cell Physiol. 170(3):241-247.
Hinman, L.M. et al. (1993). "Preparation and Characterization of Monoclonal Antibody Conjugates of the Calicheamicins: A Novel and Potent Family of Antitumor Antibiotics," Cancer Research 53:3336-3342.
Holt, L., et al. (2003) "Domain Antibodies: Proteins For Therapy," Trends in Biotechnology 21(11): 484-490.
Hoogenboom, H.R. et al. (1992). "By-Passing Immunisation: Human Antibodies from Synthetic Repertoires of Germline VH Gene Segments Rearranged in vitro," Journal of Molecular Biology 227(2):381-388.
Hoves, S. et al. (2006), "Monocyte-Derived Human Macrophages Mediate Anergy In Allogeneic T Cells and Induce Regulatory T Cells," J. Immunol. 177:2691-2698.
Hu-Lieskovan, S. et al. (2015). "Phase 1/2a Study of Double Immune Suppression Blockade by Combing a CSF1R Inhibitor (pexidartinlb/PLX3397) With an Anti PD-1 Antibody (pembrolizumab) to Treat Advance Melanoma and Other Solid Tumors," Ann. Oncol. 26(Suppl. 8):vili5-viii1 4 Abstract #18TIP, 1 pages.
Huston, J.S. et al. (1991). "Protein Engineering Of Single-Chain Fv Analogs and Fusion Proteins," Methods in Enzymology 203:46-88.
Ide, H. et al. (2002, e-pub. Oct. 15, 2002). "Expression of Colony-Stimulating Factor 1 Receptor During Prostate Development and Prostate Cancer Progression," Proc. Natl. Acad. Sci. U.S.A. 99(22): 14404-14409.
Ikonomidis, I. et al. (2005). "Increased Circulating C-Reactive Protein and Macrophage-Colony Stimulating Factor Are Complementary Predictors Of Long-Term Outcome In Patients With Chronic Coronary Artery Disease," Eur. Heart. J. 26:1618-1624.
Inaba, T. et al. (1992). "Expression of M-CSF Receptor Encoded by c-fms on Smooth Muscle Cells Derived from Arteriosclerotic Lesion," J. Biol. Chem. 267(8):5693-5699.

(56) References Cited

OTHER PUBLICATIONS

Ingram, J.R. et al. (2018). "Anti-CTLA-4 Therapy Requires an Fc Domain For Efficacy," Proc. Natl. Acad. Sci. USA 115(15):3912-3917.
International Preliminary Report on Patentability, dated Jun. 25, 2019, for PCT Application No. PCT/EP2017/083696, filed Dec. 20, 2017.
International Search Report and Written for International Patent Application No. PCT/EP2013/054676, dated May 7, 2013, filed Aug. 3, 2013, 18 pages.
International Search Report and Written Opinion for PCT Application No. PCT/EP2014/057909, dated Sep. 1, 2014, filed on Apr. 17, 2014, 14 pages.
International Search Report and Written Opinion for International Patent Application No. PCT/EP2011/053214, dated Apr. 28, 2011, filed Mar. 3, 2011, 13 pages.
International Search Report and Written Opinion for International Patent Application No. PCT/EP2012/075241, dated Feb. 22, 2013, filed Dec. 12, 2012, 14 pages.
International Search Report and Written Opinion for PCT Application No. PCT/EP2014/069451, dated Nov. 18, 2014, filed on Sep. 11, 2014, 12 pages.
International Search Report and Written Opinion dated Dec. 18, 2020, filed Sep. 29, 2020, directed to International Application No. PCT/US2020/053213, 13 pages.
International Search Report and Written Opinion, dated Feb. 19, 2018, for PCT Application No. PCT/EP2017/083696, filed Dec. 20, 2017.
Iwai, Y. et al., (2002), "Involvement of PD-L1 on Tumor Cells in the Escape from Host immune System and Tumor Immunotherapy by PD-L1 Blockade," Proc. Natl. Acad. Sci. USA 90(19): 12293-12297.
Jakobovits, A. et al. (1993). "Germ-Line Transmission and Expression of a Human-Derived Yeast Artificial Chromosome," Nature 362:255-258.
Jakobovits, A. et al. (1993), "Analysis of Homozygous Mutant Chimeric Mice: Deletion of the Immunoglobulin Heavy-Chain Joining Region Blocks B-Cell Development and Antibody Production," Proc, Natl, Acad. Sci. USA 90 (6):2551-2555.
Jeffrey, S.C. et al. (2006, e-pub. Nov. 3, 2005). "Dipeptide-based Highly Potent Doxorubicin Antibody Conjugates," Bioorganic Medicinal Chemistry Letters 16:358-362.
Jenkins, M.K. et al. (1987). "Antigen Presentation By Chemically Modified Splenocytes Induces Antigen-Specific T Cell Unresponsiveness in vitro and in vivo," J. Exp. Med. 165:302-319.
Jiang, B. et al. (2005). "A Novel Peptide isolated From a Phage Display Peptide Library With Trastuzumab Can Mimic Antigen Epitope of HER-2," J. Biol. Chem. 280(6):4656-4662.
Jose, M.D. et al. (2003). "Blockade of Macrophage Colony-Stimulating Factor Reduces Macrophage Proliferation and Accumulation in Renal Allograft Rejection," American Journal of Transplantation 3:294-300.
Kabat, E.A. et al. (1983). "Tabulation and Analysis Of Amino Acid And Nucleic Acid Sequences Of Precursors, v-Regions, c-Regions, j-Chain, beta2-Microglobulins, Major Histocompatibility Antigens, Thy-1, Complement, c-Reactive Protein, Thymopoietin, Post-gamma Globulin, and alpha2macroglobulin," Sequences of Proteins of Immunological Interest. U.S. Dept. of Health and Human Services, 10L, 2 pages.
Kacinski, B.M. (1997). "CSF-1 and Its Receptor in Breast Carcinomas and Neoplasms of the Female Reproductive Tract," Moi. Reprod. Dev. 46:71-74.
Kacinski, B.M. et al. (1990). "Ovarian Adenocarcinomas Express fms-Complementary Transcripts and fms Antigen, Often With Coexpression of CSF-1," American Journal of Pathology 137(1):135-147.
Kaku, M. et al. (2003). "Amyloid β Protein Deposition and Neuron Loss In Osteopetrotic (op/op) Mice," Brain Res. Brain Res. Protoc. 12:104-108.

Kawakami, Y. et al. (2000). "Macophage-Colony Stimulating Factor Inhibits the Growth of Human Ovarian Cancer Cells in vitro," European Journal of Cancer 36:1991-1997.
Kim, K. et al., (2014), Eradication of Metastatic Mouse Cancers Resistant to Immune Checkpoint Blockade by Suppression of Myeloid-Derived Cells, Proc. Natl. Acad. Sci. USA 111(32): 11774-11779.
King, H.D. et al. (2002, e-pub. Aug. 14, 2002). "Monoclonal Antibody Conjugates of Doxorubicin with Branched Peptide Linkers: Inhibition of Aggregation by Methoxytriethyleneglycol Chains," J. Med. Chem. 45(19):4336-4343.
Kipps, T.J. et al. (1985). "Importance of Immunoglobulin Isotype in Human Antibody-Dependent, Cell-Mediated Cytotoxicity Directed by Murine Monoclonal Antibodies," J. Exp. Med. 161(1):1-17.
Kirma, N. et al. (2007). "Elevated Expression of the Oncogene c-fms and its Ligand, the Macrophage Colony-Stimulating Factor-1, in Cervical Cancer and the Role of Transforming Growth Factor-B1 in Inducing c-fms Expression," Cancer Res 67(5):1918-1926.
Kitaura, H. et al. (2005). "M-CSF Mediates TNF-Induced inflammatory Osteolysis," J. Clin. Invest. 115(12): 3418-3427.
Kommoss, F. et al. (1994). "Co-Expression of M-CSF Transcripts and Protein, Fms (M-CSF Receptor) Transcripts and Protein, and Steroid Receptor Content in Adenocarcinomas of the Ovary," Journal of Pathology 174:111-119.
Kratz, F. et al. (2006). "Prodrugs of Anthracyclines in Cancer Chemotherapy," Current Medicinal Chemistry 13(5):477-523.
Krieg, A.M. (2008). "Toll-Like Receptor 9 (TLR9) Agonists in the Treatment of Cancer," Oncogene 7:27(2):161-167.
Kuester, K. et al. (2006). "Pharmacokinetics of Monoclonal Antibodies," Chapter 3 in "Pharmacokinetics and Pharmacodynamics of Biotech Drugs," Meibohm (Ed.), Wiley-VCH, pp. 45-91.
Lafferty et al. (1975). "A New Analysis of Allogeneic interactions," Aust. J. Exp. Biol. Med. Sci. 53(1):27-42.
Laoui, D. et al. (2014). "Functional Relationship Between Tumor-Associated Macrophages and Macrophage Colony-Stimulation Factor s Contributors to Cancer Progression," Front. Immunol. 5:489, 15 pages.
Lee, A. et al. (1992). "Functional Dissection Of Structural Domains In The Receptor For Colony-Stimulating Factor-1," The Journal of Biological Chemistry 267(23):16472-16483.
Lenschow, D.J. et al. (1996). "CD28/B7 System of T Cell Costimulation," Ann. Rev. Immunol. 14:233-258.
Lester, J.E. et al. (2006, e-pub. Nov. 29, 2005). "Current management Of Treatment-Induced Bone Loss In Women With Breast Cancer Treated In The United Kingdom," Br. J. Cancer 94:30-35.
Lewis, T.S. et al. (2011, e-pub. May 24, 2011). "Distinct Apoptotic Signaling Characteristics Of The Anti-CD40 Monoclonal Antibody Dacetuzumab And Rituximab Produce Enhanced Antitumor Activity In Non-Hodgkin Lymphoma," Clin Cancer Res. 17(14):4672-4681.
Li, J. et al. (2012). "Abstract P4-04-01: Combination Of Intratumoral CpG With Systemic Anti-OX40 and Anti-CTLA4 mAbs Eradicates Established Triple Negative Breast Tumors In Mice," Cancer Research (retrieved Mar. 26, 2015 from http://cancerres.aacrjournals.org/content/72/24_Supplement/P4-04-01.short), 4 pages.
Lode, H.N. et al. (1998), "Targeted Therapy with a Novel Enediyene Antibiotio Calicheamicin 011 Effectively Suppresses Growth and Dissemination of Liver Metastases in a Syngeneic Model of Murine Neuroblastoma," Cancer Res. 58:2925-2928.
MacCallum, R.M. et al. (1996). "Antibody-Antigen Interactions: Contact Analysis and Binding Site Topography," J. Mol. Biol. 262:732-745.
MacDonald, K.P.A. et al. (2010). "An Antibody Against The Colony-Stimulating Factor 1 Receptor Depletes The Resident Subset Of Monocytes and Tissue-and Tumor-Associated Macrophages But Does Not Inhibit Inflammation," Blood 116(19) 3955-3963.
Magiera-Mularz, K. et al. (2021). "Human and Mouse PD-L1: Similar Molecular Structure, But Different Druggability Profiles," iScience 24(101960):1-26, Supplemental Information.
Mancinio, A.T. et al. (2001, e-pub. Jul. 24, 2001). "Breast Cancer increases Osteoclastogenesis By Secreting M-CSF and Upregulating RANKL in Stromal Cells," Journal of Surgical Research 100:18-24.

(56) References Cited

OTHER PUBLICATIONS

Mantovani, A. et al. (2004). "The Chemokine System In Diverse Forms of Macrophage Activation and Polarization," Trends Immunol. 25(12):677-686.

Marks, J.D. et al. (1991). "By-Passing Immunization. Human Antibodies From V-Gene Libraries Displayed on Phage," J. Mol. Biol. 222:581-597.

Martin, T.A. et al. (2003). "Growth and Angiogenesis Of Human Breast Cancer In a Nude Mouse Tumour Model Is Reduced By NK4, a HGF/SF Antagonist," Carcinogenesis. 24(8):1317-1323.

Matsusaki, M. et al. (2019). "Three-Dimensional Cell Culture Technique and Pathophysiology," Advanced Drug Delivery Reviews, 74:95-103, 36 pages.

Mitchem, J.B. et al. (2013, e-pub. Dec. 5, 2012). "Targeting Tumor-Infiltrating Macrophages Decreases Tumor-Initiating Cells, Relieves Immunosuppression, and Improves Chemotherapeutic Responses," Cancer Res. 73(3):1128-1141.

Morrison, S.L. et al. (1984). "Chimeric Human Antibody Molecules: Mouse Antigen-Binding Domains With Human Constant Region Domains," Proc. Natl. Acad. Sci. USA 81:6851-6855.

Murad, Y.M. et al. (2009). "CpG Oligodeoxynucleotides As TLR9 Agonists: Therapeutic Applications In Cancer," BioDrugs. 23(6):361-375.

Murayama, T. et al. (1999). "Intraperitoneal Administration of Anti-c-fms Monoclonal Antibody Prevents Initial Events of Atherogenesis But Does Not Reduce the Size of Advanced Lesions in Apolipoprotein E-Deficient Mice," Circulation 99:1740-1746.

Murphy, G.M. Jr. et al. (1998). "Macrophage Colony-Stimulating Factor Augments β-Amyloid-induced Interleukin-1, Interleukin-6, and Nitric Oxide Production by Microglial Ceils," J. Biol. Chem. 273(33):20967-20971.

Murphy, G.M., Jr. et al. (2000). "Expression of Macrophage Colony-Stimulating Factor Receptor Is Increased in the AβPPV717F Transgenic Mouse Model of Alzheimer's Disease," Am. J. Pathol. 157(3):895-904.

Nagy, A. et al. (2000). "Stability of Cytotoxic Luteinizing Hormone-Releasing Hormone Conjugate (AN-152) Containing Doxorubicin 14-O-Hemiglutarate in Mouse and Human Serum in Vitro: Implications for the Design of Preclinical Studies," Proc. Nat'l. Acad. Sci. 97(2):829-334.

Neuberger, M.S. et al. (1985). "A Hapten-Specific Chimaeric IgE Antibody With Human Physiological Effector Function," Nature 314:268-270.

Ngan, H.Y. et al. (1999), "Proto-oncogenes and p53 Protein Expression in Normal Cervical Stratified Squamous Epithelium and Cervical Intra-Epithelial Neoplasia," Eur. J. Cancer 35(10): 1546-1550.

Nicola, N.A. et al. (1993). "Neutralizing and Nonneutralizing Monoclonal Antibodies To The Human Granulocyte-Macrophage Colony-Stimulating Factor Receptor α-Chain," Blood 82(6):1724-1731.

Patel, S. et al. (2009). "Colony-Stimulating Factor-1 Receptor Inhibitors For The Treatment Of Cancer and Inflammatory Disease," Curr Top Med Chem, 9(7):599-610.

Paul, W.E. (1993). Chapter 9: Fundamental Immunology, 3rd ed. Raven Press, NY., 292-295, 6 pages.

Paulus, P. et al. (2006, e-pub. Apr. 17, 2006). "Colony-Stimulating Factor-1 Antibody Reverses Chemoresistance in Human MCF-7 Breast Cancer Xenografts," Cancer Res. 66:4349-4356.

Pollard, J.W. (2004). "Tumour-Educated Macrophages Promote Tumour Progression and Metastasis," Nat. Rev. Cancer 4:71-78.

Queen, C. et al. (1989). "A Humanized Antibody That Binds to the Interleukin 2 Receptor," Proc. Natl Acad. Sci. USA 86:10029-10033.

Rabello, D. et al., (2006, e-pub. Jul. 7, 2016). "CSF1 Gene Associated With Aggressive Periodontitis In The Japanese Population," Biochem. Biophys. Res. Commun. 347:791-796.

Richman, L.P. et al. (2013, e-pub. Nov. 5, 2013). "Role of Crossliniking for Agonistic CD40 Monoclonal Antibodies as Immune Therapy of Cancer," Cancer Immunology Research, 2(1):19-26, 12 pages.

Ridge, S.A. et al. (1990). "FMS Mutations In Myelodysplastic, Leukemic, and Normal Subjects," Proc. Natl. Acad. Sci. USA 87:1377-1380.

Riechmann, L. et al. (1988). "Reshaping Human Antibodies for Therapy," Nature 332:323-327.

Riemer, A.B. et al. (2005). "Matching of Trastuzumab (Herceptin®) Epitope Mimics onto the Surface of Her-2/neu- A New Method of Epitope Definition," Molecular Immunology 42:1121-1124.

Ries, C.H. et al. (2014, e-pub. Jun. 2, 2014). "Targeting Tumor-Associated Macrophages With Anti-CSF-1R Antibody Reveals A Strategy For Cancer Therapy," Cancer Cell 25(6):846-859.

Ritchlin, C.T. et al. (2003). "Mechanisms of TNF-α- and RANKL-Mediated Osteoclastogenesis and Bone Resorption In Psoriatic Arthritis," J. Clin, Invest. 111(6):821-831.

Roggia, C. et al. (2004). "Role of TNF-α Producing T-Cells in Bone Loss Inducted by Estrogen Deficiency," Minerva Med. 95(2):125-132.

Roussel, M.F. et al. (1989). "Mouse NIH 3T3 Cells Expressing Human Colony-Stimulating Factor 1 (CSF-1) Receptors Overgrow In Serum-Free Medium Containing Human CSF-1 As Their Only Growth Factor," Proc Natl Acad Sci US A. 86(20)7924-7927.

Saitoh, T. et al. (2000). "Clinical Significance of Increased Plasma Concentration of Macrophage Colony—Stimulating Factor in Patients With Angina Pectoris," J. Am. Coll. Cardiol. 35(3):655-665.

Sapi, E. et al. (1999). "Effect of All-trans-Retinoic Acid on c-fms Proto-Oncogene [Colony-Stimulating Factor 1 (CSF-1) Receptor] Expression and CSF-1-Induced Invasion andAnchorage-Independent Growth of Human Breast Carcinoma Cells," Cancer Res. 59:5578-5585.

Sawada, M. et al. (1990). "Activation and Proliferation Of The Isolated Microglia By Colony Stimulating Factor-1 and Possible Involvement Of Protein Kinase C," Brain Res. 509:119-124.

Scholl, S.M. et al. (1994). "Anti-Colony-Stimulating Factor-1 Antibody Staining in Primary Breast Adenocarcinomas Correlates With Marked Inflammatory Cell Infiltrates and Prognosis," J. Natl. Cancer Inst. 86(2):120-126.

Shadduck, R.K. et al. (1996). "Paradoxical Stimulation of Normal and Leukemic Rat Hematopoiesis By Monoclonal Antibody to CSF-1 Receptor," Experimental Hematology 24:314-317.

Sherr, C.J. et al., (1985). "The c-fms Proto-Oncogene Product Is Releated To the Receptor For The Mononuclear Phagocyte Growth Factor, CSF-1," Cell 41(3):665-676.

Sherr, C.J. et al., (1989). "Inhibition of Colony-Stimulating Factor-i Activity By Monoclonal Antibodies To The human CSF-1 Receptor," Blood 73(7):1786-1793.

Shulman, T et al. (1997). "An Antibody Reactive With Domain 4 Of The Platelet-Derived Growth Factor β Receptor Allows BB Binding While Inhibiting Proliferation By Impairing Receptor Dimerization," The Journal Of Biological Chemistry 272(28):17400-17404.

Sloan-Lancaster et al. (993) "Induction of T-Cell Anergy by Altered T-Cell-Receptor Ligand on Live Antigen-Presenting Cells," Nature 363:156-159.

Stoch, S.A. et al. (2001). "Bone Loss in Men with Prostate Cancer Treated With Gonadotropin-Releasing Hormone Agonists," J. Clin. Endocrinol. Metab, 86(6):2787-2791.

Strausberg et al. (2008, updated Jul. 11, 2021). CSFR1 Colony Stimulating Factor 1 Receptor [*Homo Sapiens*] Accession No. AAH47521, 15 pages.

Su, H. et al. (2014). "Identification of an Isoform of Colony-Stimulationg Factor 1 Receptor mRNA in the Rat Testis," Biochem. Genet. 52(5-6):310-319.

Sudo, T. et al. (1995). "Functional Hierarchy Of c-kit and c-fms In Intramarrow Production Of CFU-M" Oncogene 11(12):2469-2476.

Sundberg, E.J. (2009, e-pub, Feb. 24, 2009). "Structural Basis Of Antibody-Antigen Interactions," Methods Mol Biol. 524:23-36.

Swierczak, A. et al. (2014, e-pub. Apr. 29, 2014). "The Promotion of Breast Cancer Metastasis Caused by Inhibition of CSF-1 R Signaling Is Blocked by Targeting the G-CSF Receptor," Cancer Immunol. Res. 2(8):765-766.

Tanaka, S. et al. (1993). "Macrophage Colony-stimulating Factor Is Indispensable for both Proliferation and Differentiation of Osteoclast Progenitors," J. Clin. Invest. 91(1):257-263.

(56) References Cited

OTHER PUBLICATIONS

Taylor, J.R. et al. (2005). "FMS Receptor for M-CSF (CSF-1) Is Sensitive To The Kinase Inhibitor Imatinib and Mutation of Asp-802 to Val Confers Resistance," Oncogene pp. 1-5.

Torgov, M.Y. et al. (2005; e-published on Apr. 27, 2005). "Generation of an Intensely Potent Anthracycline by a Monoclonal Antibody-β-Galactosidase Conjugate," Bioconjugate Chem. 16:717-721.

Tortora, G. et al. (2010), "Novel Toll-Like Receptor 9 (TLR9) Agonists IMO Inhibits Tumor Growth An Cooperates With Cetuximab In K-Ras Mutant Colon Pancreatic Cancers," Proceedings of the American Association for Cancer Research. 51:146., 1 page.

Vajdos, F. et al. (2002) "Comprehensive Functional Maps of the Antigen Binding Site of an Anti-ErbB2 Antibody Obtained with Shotgun Scanning Mutagenesis," J. Mol. Biol. 320:415-428.

Van Dijk, M.A. et al. (2001). "Human Antibodies As Next Generation Therapeutics," Curr. Opin. Chem. Biol. 5:368-374.

Vessella, R.L. et al. (2006) "Targeting Factors Involved in Bone Remodeling as Treatment Strategies in Prostate Cancer Bone Metastasis," Clin. Cancer Res. 12(20 Pt 2):6285s-6290s.

Viola, A. et al. (1996). "T Cell Activation Determined by T Cell Receptor Number and Tunable Thresholds," Science 273:104-106.

Vitetta, E.S. et al. (1987). 'Redesigning Nature's Poisons to Creaie Anti-Tumor Reagents;' Science 238:1098-1104.

Weir, E.C. et al. (1996). "Colony Stimulating Factor-1 Plays a Role in Osteoclast Formation and Function in Bone Resorption Induced By Parathyroid Hormone and Parathyroid Hormone-Related Protein," Journal of Bone and Mineral 11(10):1474-1481.

White, C.A. et al. (2001). "Antibody-Targeted Immunotherapy For Treatment of Malignancy," Annual Review of Medicine 52:125-145.

WHO Drug Information (2014). "International Nonproprietary Names for Pharmaceutical Substances (INN)," 28(2):111, 84 pages.

Yang, D.-H. et al. (2004). "The Relationship Between Point Mutation and Abnormal Expression of c-fms Oncogene in Hepatocellular Carcinoma," Hepatobiliary Pancreat. Dis. Int. 3(1):86-89.

Yuzawa, S. et al. (2007). "Structural Basis For Activation Of The Receptor Tyrosine Kinase KIT By Stem Cell Factor," Cell 130(2):323-334.

Zhang, L. et al. (2020). "Single-Cell Analyses Inform Mechanisms of Myeloid-Targeted Therapies in Colon Cancer," Cell 181(2):442-459, and Supplemental Information, 47 pages.

Zheng, G. et al. (2000). "Membrane-Bound Macrophage Colony-Stimulating Factor and Its Receptor Play Adhesion Molecule-Like Roles in Leukemic Cells," Leuk Res. 24(5):375-383.

Zhu, Y. et al. (2014, e-pub. Jul. 31, 2014). "CSF1/CSF1R Blockade Reprograms Tumor-Inflitrating Macrophages and Improves Response to T-Cell Checkpoint Immunotherapy in Pancreatic Cancer Models," Cancer Res. 74(18):5057-5069.

Zins, K. et al. (2007). "Colon Cancer Cell-Derived Tumor Necrosis Factor-α Mediates the Tumor Growth-Promoting Response in Macrophages by Up-regulating the Colony-Stimulating Factor-1 Pathway," Cancer Res. 67(3):1038-1045.

Clinical Trials.gov (Sep. 14, 2021). NCT03336216—"A Study of Cabiralizumab Given With Nivolumab With and Without Chemotherapy in Patients With Advanced Pancreatic Cancer," 9 pages.

Columbus, G. (Feb. 18, 2020). "Nivolumab/Cabiralizumab Combo Misses PFS Endpoint In Pancreatic Cancer," OncLive®, 3 pages.

Fares, C.M. et al. (Jan. 2019). "Mechanisms of Resistance to Immune Checkpoint Blockage: Why Does Checkpoint Inhibitor Immunotherapy Not Work For all Patients?," Am. Soc. Clin. Oncol. Educ. Book, 39:147-164.

Lianfang, Q. et al. (Jan. 1, 1997). Biological Effect of Monoclonal Antibodies Against CSF1 & CSF1R on Human Hepatic Cancer Cells Transplanted I Nude Mice, Tumor, 4:207-208, English Translation, 4 pages.

Ruffell, B. et al. (Apr. 13, 2015). "Macrophages and Therapeutic Resistance in Cancer," Cancer Cell, 27(4):462-472.

Stanley, E.R. et al. (Jun. 2014). "CSF-1 Receptor Signaling in Myeloid Cells," Cold Spring Habor Perspectives In Biology, 6(6):a021857, 21 pages.

METHOD OF TREATING CANCER IN A PATIENT BY ADMINISTERING AN ANTIBODY WHICH BINDS COLONY STIMULATING FACTOR-1 RECEPTOR (CSF-1R)

CROSS REFERENCE TO RELATED APPLICATIONS

This application is continuation of International Application No. PCT/EP2017/070570, filed Aug. 14, 2017, which claims priority from European Patent Application No. 16185704.0, filed Aug. 25, 2016. The contents of each of foregoing applications are incorporated herein by reference in their entireties.

SEQUENCE LISTING

This application contains a Sequence Listing submitted via EFS-WEB and hereby incorporated by reference in its entirety. Said ASCII copy, created on Jan. 31, 2019, is named P33829-US-SequenceListing.txt and is 73,728 bytes in size.

FIELD OF THE INVENTION

The current invention relates to the intermittent dosing of an anti-CSF-1R antibody in combination with macrophage activating agent, corresponding pharmaceutical compositions or medicaments using such combination therapy.

BACKGROUND OF THE INVENTION

CSF-1R and CSF-1R Antibodies

The human CSF-1 receptor (CSF-1R; colony stimulating factor 1 receptor; synonyms: M-CSF receptor; Macrophage colony-stimulating factor 1 receptor. Fms proto-oncogene, c-fms) is known since 1986 (Coussens, L., et al., Nature 320 (1986) 277-280). CSF-1R is a growth factor and encoded by the c-fms proto-oncogene (reviewed e.g. in Roth, P., and Stanley, E. R., Curr. Top. Microbiol. Immunol. 181 (1992) 141-167).

CSF-1R is the receptor for CSF-1 (colony stimulating factor 1, also called M-CSF, macrophage colony-stimulating factor) and mediates the biological effects of this cytokine (Sherr, C. J., et al., Cell 41 (1985) 665-676). The cloning of the colony stimulating factor-1 receptor (CSF-1R) (also called c-fms) was described for the first time in Roussel, M. F., et al., Nature 325 (1987) 549-552. In that publication, it was shown that CSF-1R had transforming potential dependent on changes in the C-terminal tail of the protein including the loss of the inhibitory tyrosine 969 phosphorylation which binds Cbl and thereby regulates receptor down regulation (Lee, P. S., et al., Embo J. 18 (1999) 3616-3628). Recently a second ligand for CSF-1R termed interleukin-34 (IL-34) was identified (Lin, H., et al, Science 320 (2008) 807-811).

Currently two CSF-1R ligands that bind to the extracellular domain of CSF-1R are known. The first one is CSF-1 (colony stimulating factor 1, also called M-CSF, macrophage; SEQ ID NO: 28) and is found extracellularly as a disulfide-linked homodimer (Stanley, E. R. et al., Journal of Cellular Biochemistry 21 (1983) 151-159; Stanley, E. R. et al., Stem Cells 12 Suppl. 1 (1995) 15-24). The second one is IL-34 (Human IL-34; SEQ ID NO: 29) (Hume, D. A., et al, Blood 119 (2012) 1810-1820). The main biological effects of CSF-1R signaling are the differentiation, proliferation, migration, and survival of hematopoietic precursor cells to the macrophage lineage (including osteoclast). Activation of CSF-1R is mediated by its CSF-1R ligands. CSF-1 (M-CSF) and IL-34. Binding of CSF-1 (M-CSF) to CSF-1R induces the formation of homodimers and activation of the kinase by tyrosine phosphorylation (Li, W. et al, EMBO Journal. 10 (1991) 277-288; Stanley. E. R., et al., Mol. Reprod. Dev. 46 (1997) 4-10).

The biologically active homodimer CSF-1 binds to the CSF-1R within the subdomains D1 to D3 of the extracellular domain of the CSF-1 receptor (CSF-1R-ECD). The CSF-1R-ECD comprises five immunoglobulin-like subdomains (designated D1 to D5). The subdomains D4 to D5 of the extracellular domain (CSF-1R-ECD) are not involved in the CSF-1 binding (Wang, Z., et al Molecular and Cellular Biology 13 (1993) 5348-5359). The subdomain D4 is involved in dimerization (Yeung, Y-G., et al Molecular & Cellular Proteomics 2 (2003) 1143-1155; Pixley, F. J., et al., Trends Cell Biol. 14 (2004) 628-638).

Further signaling is mediated by the p85 subunit of PI3K and Grb2 connecting to the PI3K/AKT and Ras/MAPK pathways, respectively. These two important signaling pathways can regulate proliferation, survival and apoptosis. Other signaling molecules that bind the phosphorylated intracellular domain of CSF-1R include STAT1, STAT3, PLCy, and Cbl (Bourette, R. P. and Rohrschneider, L. R., Growth Factors 17 (2000) 155-166).

CSF-1R signaling has a physiological role in immune responses, in bone remodeling and in the reproductive system. The knockout animals for either CSF-1 (Pollard, J. W., Mol. Reprod. Dev. 46 (1997) 54-61) or CSF-1R (Dai, X. M., et al., Blood 99 (2002) 111-120) have been shown to have osteopetrotic, hematopoietic, tissue macrophage, and reproductive phenotypes consistent with a role for CSF-1R in the respective cell types.

Sherr, C. J., et al., Blood 73 (1989) 1786-1793 relates to some antibodies against CSF-1R that inhibit the CSF-1 activity. Ashmun, R. A., et al., Blood 73 (1989) 827-837 relates to CSF-1R antibodies. Lenda, D., et al., Journal of Immunology 170 (2003) 3254-3262 relates to reduced macrophage recruitment, proliferation, and activation in CSF-1-deficient mice results in decreased tubular apoptosis during renal inflammation. Kitaura, H., et al., Journal of Dental Research 87 (2008) 396-400 refers to an anti-CSF-1 antibody which inhibits orthodontic tooth movement. WO 2001/030381 mentions CSF-1 activity inhibitors including antisense nucleotides and antibodies while disclosing only CSF-1 antisense nucleotides. WO 2004/045532 relates to metastases and bone loss prevention and treatment of metastatic cancer by a CSF-1 antagonist disclosing as antagonist anti-CSF-1-antibodies only. WO 2005/046657 relates to the treatment of inflammatory bowel disease by anti-CSF-1-antibodies. US 2002/0141994 relates to inhibitors of colony stimulating factors. WO 2006/096489 relates to the treatment of rheumatoid arthritis by anti-CSF-1-antibodies. WO 2009/026303 and WO 2009/112245 relate to certain anti-CSF-1R antibodies binding to CSF-1R within the first three subdomains (D1 to D3) of the Extracellular Domain (CSF-1R-ECD). WO2011/123381, WO2011/140249, WO2012/110360 relate to antibodies against CSF-1R. WO2011/070024 relate to certain anti-CSF-1R antibodies binding to CSF-1R within the dimerization domain (D4 to D5).

WO2013/132044, WO2014/173814 and WO 2015/036511 relate inter alia to the combination therapy of anti-CSF-1R antibodies with different macrophage activating agents like agonistic CD40 antibodies, a TLR agonists, an antagonistic PD-L1 antibodies. It has now been found that a combination therapy with a treatment scheme comprising an intermediate delay or stop of the anti-CSF-1R antibody is advantageous over a treatment scheme comprising continuous co-administration of both the anti CSF-1R antibody and the macrophage activating agent.

SUMMARY OF THE INVENTION

Combination of cancer immunotherapies to harness the amplifying cytotoxic T cells to fight cancer has become a major focus in the treatment of patients. CSF-1R blocking agents that eliminate T cell suppressive tumor-associated macrophages (TAM) in tumors, represent a novel player for combinatorial immunotherapies. Surprisingly, we found that an agonistic CD40 antibody which requires TAM as effector cells for its therapeutic effect, induced complete remission in various cancer mouse models when combined with the TAM depleting CSF-1R antibody. Ex vivo analysis of sorted monocyte and TAM populations revealed that only the combination treatment resulted in an immediate, transient and unique activation of proinflammatory TAM before they were eliminated by the CSF-1R mAb.

TAM and $CD8^+$ T cell depletion experiments indicated that therapeutic benefit of this combination depended on the presence of both populations. Colorectal cancer patients show co-expression of CSF1R and CD40 on TAMs and will be treated with this combination in a recently started clinical trial.

Combined depletion of immune-suppressive tumor-associated macrophages together with activating CD40 antibody leads to complete tumor rejection in various tumor models depending on the macrophage infiltrate. Prevalence data from various human cancer patients showed both show co-expression of CSF1R and CD40.

In case if a combination treatment of anti-CSF1R and anti-CD40 is given before the full depletion of all TAMS by anti-CSF1R there is a change of phenotype and a a strong synergistic anti-tumoral effect of the combination treatment can be seen. In contrast, in case of a complete pre-depletion of all TAMS before the combination treatment of anti-CSF1R and anti-CD40, no synergistic anti-tumoral effects can be observed. So in consequence macrophages are needed for a strong anti-tumoral effect of the combination treatment of anti-CSF1R and anti-CD40.

Consequently a recovery of macrophages is needed for the next synergistic combination treatment.

Therefore one aspect of the invention is an antibody which binds to human CSF-1R, for use in
  a) the treatment of cancer (preferably solid tumors, melanoma, colorectal, mesothelioma), or
  b) the treatment of a patient having a tumor with CSF-1R expressing macrophage infiltrate,
  wherein the anti-CSF-1R antibody is administered in a first treatment cycle in combination with a macrophage activating agent selected from the group of an agonistic CD40 antibody, a Toll-like receptor (TLR) ligand, a TLR agonist, an antagonistic PD-L1 antibody,
  and wherein in the following treatment cycles the anti-CSF-1R antibody is administered only at every second cycle in combination with the macrophage activating agent, while the macrophage activating agent is administered at each treatment cycle.

Another aspect of the invention is an antibody which binds to human CSF-1R, for use in
  a) the treatment of cancer (preferably solid tumors, melanoma, colorectal, mesothelioma), or
  b) the treatment of a patient having a tumor with CSF-1R expressing macrophage infiltrate,
  wherein the anti-CSF-1R antibody is administered in a first treatment cycle in combination with a macrophage activating agent selected from the group of an agonistic CD40 antibody, a Toll-like receptor (TLR) ligand, a TLR agonist, an antagonistic PD-L1 antibody,
  and wherein in the following the anti-CSF-1R antibody is administered only in combination with the macrophage activating agent after a significant recovery of CD14+ CD16+ positive monocytes in blood serum (in one embodiment the recovery is more than 60%, in one embodiment more than 80%).

Another aspect of the invention is an antibody which binds to human CSF-1R, for use in
  a) the treatment of cancer (preferably solid tumors, melanoma, colorectal, mesothelioma), or
  b) the treatment of a patient having a tumor with CSF-1R expressing macrophage infiltrate,
  wherein the anti-CSF-1R antibody is administered in a first treatment cycle in combination with a macrophage activating agent selected from the group of an agonistic CD40 antibody, a Toll-like receptor (TLR) ligand, a TLR agonist, an antagonistic PD-L1 antibody,
  and wherein in the following the anti-CSF-1R antibody is administered only in combination with the macrophage activating agent after a significant recovery of CD163+/CD68+ positive tumor associated macrophages (in one embodiment the recovery is more than 60%, in one embodiment more than 80%).

One embodiment of the invention is the described anti-CSF-1R antibody for use in one of the above treatments, wherein in the following treatment cycles the anti-CSF-1R antibody is administered only at every second cycle in combination with the macrophage activating agent, while the macrophage activating agent is administered at each treatment cycle.

One embodiment of the invention is the described anti-CSF-1R antibody for use in one of the above treatments, wherein the length of the treatment cycle is between 2 and 4 weeks,
  in one preferred embodiment the length of the treatment cycle is between 18 and 24 days,
  in one preferred embodiment the length of the treatment cycle is (about) 3 weeks.

One embodiment of the invention is the described anti-CSF-1R antibody for use in one of the above treatments, wherein the anti-CSF-1R antibody is administered at a dose of 600-1200 mg (in one preferred embodiment at a dose of 750-1100 mg, in one embodiment at a dose of 750-1000 mg, in another embodiment at a dose of 900-1000 mg, in another embodiment at a dose of 750 mg, in another embodiment at a dose of 900 mg, in another embodiment at a dose of 1000 mg).

One embodiment of the invention is the described anti-CSF-1R antibody for use in one of the above treatments, wherein the macrophage activating agent is an agonistic CD40 antibody and wherein the agonistic CD40 antibody is administered at a dose of 4-16 mg (in one preferred embodiment at a dose of 8-16 mg) at each cycle.

One embodiment of the invention is the described anti-CSF-1R antibody for use in one of the above treatments, wherein the macrophage activating agent is an antagonistic PD-L antibody and wherein the antagonistic PD-L1 antibody is administered at a dose of 1100-1300 mg (in one preferred embodiment at a dose of 1200) at each cycle.

One embodiment of the invention is the described anti-CSF-1R antibody for use in one of the above treatments, wherein the combined therapy is for use in treating or delaying progression of an immune related disease such as tumor immunity.

One embodiment of the invention is the described anti-CSF-1R antibody for use in one of the above treatments, wherein the combined therapy is for use in stimulating an immune response or function, such as T cell activity.

DESCRIPTION OF THE FIGURES

FIGS. 1A, 1B, and 1C show the combined treatment using anti-CD40 and anti-CSF-1R results in complete rejection of MC38 tumors. FIG. 1A shows the overall study design. FIG. 1B shows the survival readout. Mice were graphically censored once the tumor volume measured ≥700 mm³. Numbers indicate the amount of tumor free mice in the combination group at the end of the study on day 71; n=10 mice per group. FIG. 1C shows the re-challenge of tumor-free mice using 5×10⁶ tumor cells. Tumor volume was monitored daily by caliper measurement.

FIGS. 2A and 2B show the depletion of CD8α positive T cells prior to combined anti-CD40 and anti-CSF-1R treatment abolishes high survival rates in MC38 tumor bearing mice. FIG. 2A shows the overall study design. FIG. 2B shows the survival readout. Day 11 indicates the start of anti-CD40 plus/minus anti-CSF-1R antibodies; while anti-CD40 was only given once, the anti-CSF-1R was given weekly from hereon. Mice were graphically censored once the tumor volume measured≥700 mm³. Numbers indicate the amount of tumor free mice in the combination group at the end of the study on day 71; n=10 mice per group.

FIGS. 3A, 3B, and 3C shows the depletion of TAM prior to combined anti-CD40 and anti-CSF-1R treatment abolishes high survival rates in MC38 tumor bearing mice. FIG. 3A shows the overall study design. FIG. 3B shows the flow cytometric analysis of TAM (DAPI⁻CD45⁺CD11b⁺F4/80$^{high}$Ly6G$^{negative}$Ly6C$^{low}$), n=4 per group; statistical analysis by ONE way ANOVA. *** p≤0.0001. FIG. 3C shows the survival readout. Mice were censored graphically once the tumor volume reached ≥700 mm³. Numbers indicate the amount of tumor free mice at the end of the study on day 49; n=10 mice per group.

FIGS. 4A and 4B show an RNA sequencing experiment on myeloid cells. FIG. 4A shows the gating strategy for analysis of myeloid cells. FIG. 4B shows an overview on signature analysis comparing RNAseq data to 88 available signatures.

FIG. 5 shows a correlation of quantified IHC analysis. CRC: colorectal carcinoma; TNBC: tripple negative breast cancer FIG. 6 shows that an anti-CD40 and anti-CSF-1R combination is well tolerated in MC38 tumor bearing mice.

FIG. 7 shows simulated Median Profiles of CD14+CD16+ Monocytes and anti-CSF-1R antibody Emactuzumab Pharmacokinetics Following Administration of 750 mg Q6W FIG. 8 shows mean Calculated Target Saturation using TMDD Model Following IV Administration of Emactuzumab

DETAILED DESCRIPTION OF THE INVENTION

Figure 1A:
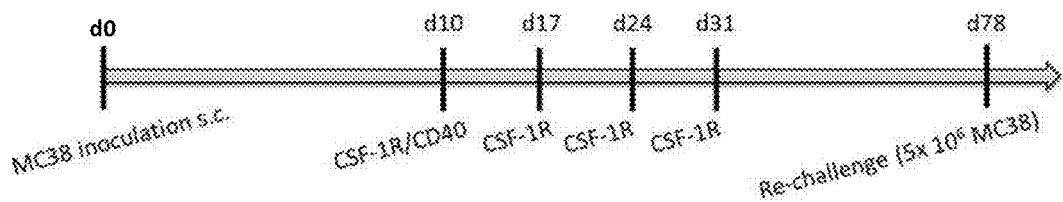
FIG. 1A-FIG. 1C.

The term "macrophage activating" refers e.g. to the stimulation of macrophages which are able to secrete a wide range of biologically active compounds such as several pro-inflammatory cytokines and expression of co-stimulatory surface molecules, enhanced antigen presentation or other surface markers associated with activation.

The "macrophage activating agent" according to the invention is selected to from the group of an CD40 agonist, a Toll-like receptor (TLR) ligand, a TLR agonist, an antagonistic PD-L1 antibody.

A "tumor with CSF-1R expressing macrophage infiltrate" refers to a heterogenous tumor comprising tumor cells and infiltrating CSF-1R-expressing tumor-associated macrophages (TAMs) or tissue resident macrophages.

As surrogate for the tumor associated macrophages (TAMs) the precursor human CD14+CD16+(positive) monocytes in blood serum are measured, as the recovery of this blood monocytes correlates with the subsequent recovery of the tumor associated macrophages (TAMs). The term "after a significant recovery of CD14+CD16+ positive monocytes in blood serum (in one embodiment the recovery is more than 60%, in one embodiment more than 80%)" as used herein refers to E.g. in an Example 1B, a pharmacodynamic model has been fitted to the human CD14+CD16+ monocyte data. Based on preliminary population analysis, a dose of 750 mg administered Q6W shows recovery of CD14+CD16+ monocytes towards.

As the first treatment with the anti-CSF-1R antibody leads to a strong reduction/depletion of tumor associated macrophages (TAMs) and their precursor human CD14+CD16+ (positive) monocytes in blood serum, the length of an treatment cycle is chosen to provide enough time that a significant recovery of the of this human CD14+CD16+ (positive) monocytes blood monocytes correlating with the subsequent recovery of the tumor associated macrophages (TAMs), so that the TAMs are not continuously depleted. And the combination treatment with the CD40 agonist can exert its strong synergistic anti-tumor efficacy.

CSF-1R is a protein encoded by the CSF-1R gene. It controls the production, differentiation, and function of M2 macrophages, which, in turn, support tumor growth and metastasis formation and secrete immunosuppressive cytokines, leading to a poor prognosis in patients. Furthermore, presence of CSF-1R positive macrophages in several human cancers (such as ovarian and breast carcinoma) has been shown to correlate not only with increased vascular density but also worse clinical outcome. CSF-1R inhibitors, which selectively inhibit M2-like TAMs, have demonstrated activity in preclinical models (DeNardo, D. et al., Cancer Discovery 1 (2011) 54-67; Lin, E. et al., J. Exp. Med. 193 (2001) 727-740). Blockade of CSF-1R activity results in reduced recruitment of TAMs and, in combination with chemotherapy, a synergistic action results in reduced tumor growth and metastatic burden. Recent data have shown that in patients with PVNS and TGCT, overexpression of the CSF-1 is detected and is in part mediated by a translocation of the CSF-1R gene (West, R. B. et al., Proc. Natl. Acad. Sci. USA 3 (2006) 690-695). In breast cancer the presence of a CSF-1 response gene signature predicts risk of recurrence and metastasis (Beck, A. et al., Clin. Cancer Res. 3 (2009) 778-787).

Many tumors are characterized by a prominent immune cell infiltrate, including macrophages. Initially, the immune cells were thought to be part of a defense mechanism against the tumor, but recent data support the notion that several immune cell populations including macrophages may, in fact, promote tumor progression. Macrophages are characterized by their plasticity. Depending on the cytokine microenvironment, macrophages can exhibit so-called M1 or M2-subtypes. M2 macrophages are engaged in the suppression of tumor immunity. They also play an important role in tissue repair functions such as angiogenesis and tissue remodeling which are coopted by the tumor to support growth. In contrast to tumor promoting M2 macrophages, M1 macrophages exhibit antitumor activity via the secretion of inflammatory cytokines and their engagement in antigen presentation and phagocytosis (Mantovani, A. et al., Curr. Opin. Immunol. 2 (2010) 231-237).

By secreting various cytokines such as colony stimulating factor 1 (CSF-1) and IL-10, tumor cells are able to recruit and shape macrophages into the M2-subtype, whereas cytokines such as granulocyte macrophage colony stimulating factor (GM-CSF), IFN-gamma program macrophages towards the M1 subtype. Using immunohistochemistry, it is possible to distinguish between a macrophage subpopulation co-expressing CD68 and CD163, which is likely to be enriched for M2 Macrophages, and a subset showing the CD68+/MHC II+, or CD68+/CD80+ immunophenotype, likely to include M1 macrophages. Cell shape, size, and spatial distribution of CD68 and CD163 positive macrophages is consistent with published hypotheses on a tumor-promoting role of M2 macrophages, for example by their preferential location in tumor intersecting stroma, and vital tumor areas. In contrast. CD68+/MHC class II+ macrophages are ubiquitously found. Their hypothetical role in phagocytosis is reflected by clusters of the CD68+/MHC class II+, but CD163-immunophenotype near apoptotic cells and necrotic tumor areas.

The subtype and marker expression of different macrophage subpopulations is linked with their functional state. M2 macrophages can support tumorigenesis by:
  a) enhancing angiogenesis via the secretion of angiogenic factors such as VEGF or bFGF,
  b) supporting metastasis formation via secretion of matrix metalloproteinases(MMPs), growth factors and migratory factors guiding the tumor cells to the blood stream and setting up the metastatic niche (Wyckoff, J. et al., Cancer Res. 67 (2007) 2649-2656),
  c) playing a role in building an immunosuppressive milieu by secreting immunosuppressive cytokines such as IL-4, 11-13, IL-Ira and IL-10, which in turn regulate T regulatory cell function. Conversely CD4 positive T cells have been shown to enhance the activity of tumor promoting macrophages in preclinical models (Mantovani, A. et al., Eur. J. Cancer 40 (2004) 1660-1667; DeNardo, D. et al., Cancer Cell 16 (2009) 91-102).

Accordingly, in several types of cancer (e.g. breast, ovarian, Hodgkin's lymphoma) the prevalence of M2 subtype tumor associated macrophages (TAMs) has been associated with poor prognosis (Bingle, L. et al., J. Pathol. 3 (2002) 254-265; Orre, M., and Rogers, P. A., Gynecol. Oncol. 1 (1999) 47-50; Steidl, C. et al., N. Engl. J. Med. 10 (2010) 875-885). Recent data show a correlation of CD163 positive macrophage infiltrate in tumors and tumor grade (Kawamura, K. et al., Pathol. Int. 59 (2009) 300-305). TAMs isolated from patient tumors had a tolerant phenotype and were not cytotoxic to tumor cells (Mantovani, A. et al., Eur. J. Cancer 40 (2004) 1660-1667). However, infiltration of TAMs in the presence of cytotoxic T cells correlates with improved survival in non small cell lung cancer and hence reflects a more prominent M1 macrophage infiltrate in this tumor type (Kawai, O. et al., Cancer 6 (2008) 1387-1395).

CSF-1R belongs to the class III subfamily of receptor tyrosine kinases and is encoded by the c-fms proto-oncogene. Binding of CSF-1 or IL-34 induces receptor dimerization, followed by autophosphorylation and activation of downstream signaling cascades. Activation of CSF-1R regulates the survival, proliferation and differentiation of monocytes and macrophages (Xiong, Y. et al., J. Biol. Chem. 286 (2011) 952-960).

In addition to cells of the monocytic lineage and osteoclasts, which derive from the same hematopoietic precursor as the macrophage, CSF-1R/c-fms has also been found to be expressed by several human epithelial cancers such as ovarian and breast cancer and in leiomvosarcoma and TGCT/PVNS, albeit at lower expression levels compared to macrophages. As with TGCT/PVNS, elevated levels of CSF-1, the ligand for CSF-1R, in serum as well as ascites of ovarian cancer patients have been correlated with poor prognosis (Scholl, S. et al., Br. J. Cancer 62 (1994) 342-346; Price, F. et al., Am. J. Obstet. Gynecol. 168 (1993) 520-527). Furthermore, a constitutively active mutant form of CSF1R is able to transform NIH3T3 cells, one of the properties of an oncogene (Chambers, S., Future Oncol 5 (2009) 1429-1440).

The human CSF-1R (CSF-1 receptor; synonyms: M-CSF receptor; Macrophage colony-stimulating factor 1 receptor, Fins proto-oncogene, c-fins, SEQ ID NO: 24)) is known since 1986 (Coussens, L., et al., Nature 320 (1986) 277-280). CSF-1R is a growth factor and encoded by the c-fms proto-oncogene (reviewed e.g. in Roth, P. and Stanley, E. R., Curr. Top. Microbiol. Immunol. 181 (1992) 141-167).

CSF-1R is the receptor for the CSF-1R ligands CSF-1 (macrophage colony stimulating factor, also called M-CSF) (SEQ ID No.: 28) and IL-34 (SEQ ID No.: 29) and mediates the biological effects of these cytokines (Sherr, C. J., et al., Cell 41 (1985) 665-676; Lin, H., et al., Science 320 (2008) 807-811). The cloning of the colony stimulating factor-1 receptor (also called c-fms) was described for the first time in Roussel, M. F., et al., Nature 325 (1987) 549-552. In that publication, it was shown that CSF-1R had transforming potential dependent on changes in the C-terminal tail of the protein including the loss of the inhibitory tyrosine 969 phosphorylation which binds Cbl and thereby regulates receptor down regulation (Lee, P. S., et al., Embo J. 18 (1999) 3616-3628).

CSF-1R is a single chain, transmembrane receptor tyrosine kinase (RTK) and a member of the family of immunoglobulin (Ig) motif containing RTKs characterized by 5 repeated Ig-like subdomains D1-D5 in the extracellular domain (ECD) of the receptor (Wang, Z., et al Molecular and Cellular Biology 13 (1993) 5348-5359). The human CSF-1R Extracellular Domain (CSF-1R-ECD) (SEQ ID NO: 25) comprises all five extracellular Ig-like subdomains D1-D5. The human CSF-1R fragment D1-D3 (SEQ ID NO: 26) comprises the respective subdomains D1-D3. The sequences are listed without the signal peptide. The human CSF-1R fragment D4-D5 (SEQ ID NO: 27) comprises the respective subdomains D4-D5.

Currently two CSF-1R ligands that bind to the extracellular domain of CSF-1R are known. The first one is CSF-1 (colony stimulating factor 1, also called M-CSF, macrophage; human CSF-1, SEQ ID NO: 28) and is found extracellularly as a disulfide-linked homodimer (Stanley, E. R. et al., Journal of Cellular Biochemistry 21 (1983) 151-159; Stanley, E. R. et al., Stem Cells 12 Suppl. 1 (1995) 15-24). The second one is IL-34 (human IL-34; SEQ ID NO: 29) (Hume, D. A., et al, Blood 119 (2012) 1810-1820). Thus in one embodiment the term "CSF-1R ligand" refers to human CSF-1 (SEQ ID NO: 28) and/or human IL-34 (SEQ ID NO: 29).

For experiments often the active 149 amino acid (aa) fragment of human CSF-1 (aa 33-181 of SEQ ID NO: 28) is used. This active 149 as fragment of human CSF-1 (aa 33-181 of SEQ ID NO: 28) is contained in all 3 major forms of CSF-1 and is sufficient to mediate binding to CSF-1R (Hume. D. A., et al, Blood 119 (2012) 1810-1820).

The main biological effects of CSF-1R signaling are the differentiation, proliferation, migration, and survival of hematopoietic precursor cells to the macrophage lineage (including osteoclast). Activation of CSF-1R is mediated by its CSF-1R ligands, CSF-1 (M-CSF) and IL-34. Binding of CSF-1 (M-CSF) to CSF-1R induces the formation of homodimers and activation of the kinase by tyrosine phosphorylation (Li, W. et al, EMBO Journal. 10 (1991) 277-288; Stanley, E. R., et al., Mol. Reprod. Dev. 46 (1997) 4-10).

As used herein, "binding to human CSF-1R" or "specifically binding to human CSF-1R" or "which binds to human CSF-1R" or "anti-CSF-1R antibody" refers to an antibody specifically binding to the human CSF-1R antigen with a binding affinity of KD-value of $1.0 \times 10^{-8}$ mol/l or lower, in one embodiment of a KD-value of $1.0 \times 10^{-9}$ mol/l or lower. The binding affinity is determined with a standard binding assay, such as surface plasmon resonance technique (BIAcore®, GE-Healthcare Uppsala, Sweden). Thus an "antibody binding to human CSF-1R" as used herein refers to an antibody specifically binding to the human CSF-1R antigen with a binding affinity of KD $1.0 \times 10^{-8}$ mol/l or lower (in one embodiment $1.0 \times 10^{-8}$ mol/l-$1.0 \times 10^{-13}$ mol/l), in on embodiment of a KD $1.0 \times 10^{-9}$ mol/l or lower (in one embodiment $1.0 \times 10^{-9}$ mol/l-$1.0 \times 10^{-13}$ mol/l).

In one embodiment the antibody which binds to human CSF-1R used in the combination therapy described herein is selected from the group consisting of hMab 2F11-c11, hMab 2F11-d8, hMab 2F11-e7, hMab 2F11-f12, and hMab 2F11-g1.

These antibodies are described in WO2011/070024 and are characterized in comprising the following VH and VL sequences as described herein:

TABLE 1

| anti-CST-1R antibody | amino acid sequence of the heavy chain variable domain VH, SEQ ID NO: | amino acid sequence of the light chain variable domain VL, SEQ ID NO: |
| --- | --- | --- |
| hMab 2F11-c11 | 1 | 2 |
| hMab 2F11-d8 | 3 | 4 |
| hMab 2F11-e7 | 5 | 6 |
| hMab 2F11-f12 | 7 | 8 |
| hMab 2F11-g1 | 9 | 10 |

These anti-CSF-1R antibodies described in the invention bind to the extracellular domain of human CSF-1R, in one embodiment to the membrane proximal domains D4 and D5 which constitute the receptor dimerization interface.

In one embodiment they bind to the domains D1 to D3. In one embodiment, the antibody which binds to human CSF-1R used in the combination therapy described herein are disclosed in WO 2009/026303, WO 2009/112245, WO2011/123381, WO2011/140249, WO2012/110360 (which all are incorporated by reference).

The anti-CSF-1R antibodies described in the invention block CSF-1, IL-34 mediated as well as ligand-independent activation of the receptor resulting in induction of apoptosis of M2-like macrophages differentiated in vitro in the presence of CSF-1 while sparing the M1-like GM-CSF differentiated macrophages. In human breast cancer tissue, M2 (CD68+/CD163+) macrophages and CSF1R-expressing macrophages are co-localized.

The CD40 antigen is a 50 kDa cell surface glycoprotein which belongs to the Tumor Necrosis Factor Receptor (TNF-R) family. (Stamenkovic et al., EMBO J. 8:1403-10 (1989).) CD40 is expressed in many normal and tumor cell types, including B lymphocytes, dendritic cells, monocytes, macrophages, thymic epithelium, endothelial cells, fibroblasts, and smooth muscle cells. (Paulie S. et al., Cancer Immunol. Immunother. 20:23-8 (1985); Banchereau J. et al., Adv. Exp. Med. & Biol. 378:79-83 (1995); Alderson M. R. et al., J. of Exp. Med. 178:669-74 (1993); Ruggiero G. et al., J. of Immunol. 156:3737-46 (1996); Hollenbaugh D. et al., J. of Exp. Med. 182:33-40 (1995); Yellin M. J. et al., J. of Leukocyte Biol. 58:209-16 (1995); and Lazaar A. L. et al., J. of Immunol. 161:3120-7 (1998).) CD40 is expressed in all B-lymphomas and in 70% of all solid tumors. Although constitutively expressed, CD40 is up-regulated in antigen presenting cells by maturation signals, such as LPS, IL-1beta, IFN-gamma and GM-CSF.

CD40 activation plays a critical role in regulating humoral and cellular immune responses. Antigen presentation without CD40 activation can lead to tolerance, while CD40 signaling can reverse such tolerance, enhance antigen presentation by all antigen presenting cells (APCs), lead to secretion of helper cytokines and chemokines, increase co-stimulatory molecule expression and signaling, and stimulate cytolytic activity of immune cells. CD40 plays a critical role in B cell proliferation, maturation and class switching. (Foy T. M. et al., Ann. Rev. of Immunol. 14:591-617 (1996).) Disruption of the CD40 signaling pathway leads to abnormal serum immunoglobulin isotype distribution, lack of CD4+ T cell priming, and defects in secondary humoral responses. For example, the X-linked hyper-lgM syndrome is a disease associated with a mutation in the human CD40L gene, and it is characterized by the inability of affected individuals to produce antibodies other than those of the IgM isotype, indicating that the productive interaction between CD40 and CD40L is required for an effective immune response.

CD40 engagement by CD40L leads to the association of the CD40 cytoplasmic domain with TRAFs (TNF-R associated factors). (Lee H. H. et al., Proc. Natl. Acad. Sci. USA 96:1421-6 (1999); Pullen S. S. et al., Biochemistry 37:11836-45 (1998); Grammar A. C. et al., J. of Immunol. 161:1183-93 (1998); Ishida T. K. et al., Proc. Acad Acad Sci. USA 93:9437-42 (1996); Pullen S. S. et al., J. of Biol. Chem. 274:14246-54 (1999)). The interaction with TRAFs can culminate in the activation of both NFkappa B and Jun/API pathways. (Tsukamoto N. et al., Proc. Natl. Acad. Sci. USA 96:1234-9 (1999); Sutherland C. L. et al., J. of Immunol. 162:4720-30 (1999).) Depending on cell type, this signaling leads to enhanced secretion of cytokines such as IL-6 (Jeppson J. D. et al., J. of Immunol. 161:1738-42 (1998); Uejima Y. et al., Int. Arch. of Allergy & Immunol. 110:225-32, (1996), IL-8 (Gruss H. J. et al., Blood 84:2305-14 (1994); von Leoprechting A. et al., Cancer Res. 59:1287-94 (1999); Denfeld R. W. et al., Europ. J. of Immunol. 26:2329-34 (1996)), IL-12 (Cella M. et al., J. of Exp. Med. 184:747-52 (1996); Ferlin W. G. et al., Europ. J. of Immunol. 28:525-31 (1998); Armant M. et al., Europ. J. of Immunol. 26:1430-4 (1996); Koch F. et al., J. of Exp. Med. 184:741-6 (1996); Seguin R. and L. H. Kasper, J. of Infect. Diseases 179:467-74 (1999); Chaussabel D. et al., Infection & Immunity 67:1929-34 (1999)), IL-15 (Kuniyoshi J. S. et al., Cellular Immunol. 193:48-58 (1999)) and chemokines (MIP1alpha, MIP1beta, RANTES, and others) (McDyer J.

F. et al., J. of Immunol. 162:3711-7 (1999); Schaniel C. et al., J. of Exp. Med. 188:451-63 (1998); Altenburg A. et al., J. of Immunol. 162:4140-7 (1999), Deckers J. G. et al., J. of the Am. Society of Nephrology 9:1187-93 (1998)), increased expression of MHC class I and II (Santos-Argumedo L. et al., Cellular Immunol. 156:272-85 (1994)), and increased expression of adhesion molecules (e.g., ICAM) (Lee H. H. et al., Proc. Natl. Acad. Sci. USA. 96:1421-6 (1999); Grousson J. et al., Archives of Dermatol. Res. 290:325-30 (1998); Katada Y. et al., Europ. J. of Immunol. 26:192-200 (1996); Mavumi M. et al., J. of Allergy & Clin. Immunol. 96:1136-44 (1995); Flores-Romo L. et al., Immunol. 79:445-51 (1993)) and costimulatory molecules (e.g., B7) (Roy M. et al., Europ. J. of Immunol. 25:596-603 (1995); Jones K. W. and C. J. Hackett, Cellular Immunol. 174:42-53 (1996); Caux C. et al., Journal of Exp. Med. 180:1263-72 (1994); Kiener P. A. et al., J. of Immunol. 155:4917-25 (1995)). Cytokines induced by CD40 engagement enhance T cell survival and activation.

In addition to enhancement of cellular and immune function, the effects of CD40 activation include: cell recruitment and differentiation by chemokines and cytokines; activation of monocytes; increased cytolytic activity of cytolytic T lymphocyte (CTL) and natural killer (NK) cells; induction of apoptosis in CD40 positive tumors; enhancement of immunogenicity of CD40 positive tumors; and tumor-specific antibody production. The role of CD40 activation in cell-mediated immune responses is also well established, and it is reviewed in: Grewal et al., Ann. Rev. of Immunol. 16:111-35 (1998); Mackey et al., J. of Leukocvte Biol. 63:418-28 (1998); and Noelle R. J., Agents & Actions— Suppl. 49:17-22 (1998).

Studies using a cross-priming model system showed that CD40 activation of APCs can replace helper T cell requirement for the generation of ctolytic T lymphocyte (CTL). (Bennett et al., Nature 393:478-480 (1998).) Evidence from CD40L deficient mice indicates a clear requirement for CD40 signaling in helper T cell priming. (Grewal I. S. et al., Science 273:1864-7 (1996); Grewal I. S. et al., Nature 378:617-20 (1995).) CD40 activation converts otherwise tolerogenic, antigen bearing B cells into competent APCs. (Buhlmann J. E. et al., Immunity 2:645-53 (1995).) CD40 activation induces maturation and differentiation of cord blood progenitors into dendritic cells. (Flores-Romo L. et al., J. of Exp. Med. 185:341-9 (1997); Mackey M. F. et al., J. of Immunol. 161:2094-8 (1998).) CD40 activation also induces differentiation of monocytes into functional dendritic cells. (Brossart P. et al., Blood 92:4238-47 (1998).) Further, CD40 activation enhances cytolytic activity of NK cells through APC-CD40 induced cytokines (Carbone E. et al., J. of Exp. Med. 185:2053-60 (1997); Martin-Fontecha A. et al., J. of Immunol. 162:5910-6 (1999).) These observations indicate that CD40 plays an essential role in the initiation and enhancement of immune responses by inducing maturation of APCs, secretion of helper cytokines, upregulation of costimulatory molecules, and enhancement of effector functions.

The critical role of CD40 signaling in the initiation and maturation of humoral and cytotoxic immune responses makes this system an ideal target for immune enhancement. Such enhancement can be particularly important for mounting effective immune responses to tumor antigens, which are generally presented to the immune system through cross-priming of activated APCs. (Huang A. Y. et al., Ciba Foundation Symp. 187:229-44 (1994); Toes R E. M. et al., Seminars in Immunol. 10:443-8 (1998); Albert M. L. et al., Nature 392:86-9 (1998); Bennett S. R. et al., J. of Exp. Med. 186:65-70 (1997).)

Several groups have demonstrated the effectiveness of CD40 activation for antitumor responses in vitro and in vivo. (Toes R. E. M. et al., Seminars in Immunol. 10:443-8 (1998).) Two groups, using lung metastatic model of renal cell carcinoma and subcutaneous tumors by virally transformed cells, have independently demonstrated that CD40 activation can reverse tolerance to tumor-specific antigens, resulting in efficient antitumor priming of T cells. (Sotomayor E. M. et al., Nature Medicine 5:780-787 (1999); Diehl L. et al., Nature Medicine 5:774-9 (1999).) Antitumor activity in the absence of immune cells was also reported by CD40L and anti-CD40 antibody treatment in a human breast cancer line model in SCID mice. (Hirano A. et al., Blood 93:2999-3007 (1999).) CD40 activation by anti-CD40 antibody was recently shown to eradicate CD40+ and CD40- lymphoma in mouse models. (French R. R. et al., Nature Medicine 5:548-53 (1999).) Furthermore, previous studies by Glennie and co-workers conclude that signaling activity by anti-CD40 antibodies is more effective for inducing in vivo tumor clearance than other anti-surface marker antibodies capable of recruiting effectors. (Tutt A. L. et al., J. of Immunol. 161:3176-85 (1998).) Consistent with these observations, when anti-CD40 antibodies were tested for activity against CD40+ tumor cells in vivo, most but not all of the tumoricidal activity was associated with CD40 signaling rather than ADCC. (Funakoshi S. et al., J. of Immunotherapy with Emphasis on Tumor Immunol. 19:93-101 (1996).) In another study, bone marrow dendritic cells were treated ex vivo with a variety of agents, and tested for in vivo antitumor activity. These studies demonstrated that CD40L stimulated DCs were the most mature and most effective cells that mounting an antitumor response.

The essential role of CD40 in antitumor immunity has also been demonstrated by comparing responses of wild-type and CD40−/− mice to tumor vaccines. These studies show that CD40−/− mice are incapable of achieving the tumor immunity observed in normal mice. (Mackey M. F. et al., Cancer Research 57:2569-74 (1997).) In another study, splenocytes from tumor bearing mice were stimulated with tumor cells and treated with activating anti-CD40 antibodies ex vivo, and were shown to have enhanced tumor specific CTL activity. (Donepudi M. et al., Cancer Immunol. Immunother. 48:153-164 (1999).) These studies demonstrate that CD40 occupies a critical position in antitumor immunity, in both CD40 positive and negative tumors. Since CD40 is expressed in lymphomas, leukemias, multiple myeloma, a majority of carcinomas of nasopharynx, bladder, ovary, and liver, and some breast and colorectal cancers, activation of CD40 can have a broad range of clinical applications.

The "CD40 agonist" as used herein includes any moiety that agonizes the CD40/CD40L interaction. CD40 as used in this context refers preferably to human CD40, thus the CD40 agonist is preferably an agonist of human CD40. Typically these moieties will be "agonistic CD40 antibodies" or "agonistic CD40L polypeptides". These antibodies include by way of example human antibodies, chimeric antibodies, humanized antibodies, bispecific antibodies, scFvs, and antibody fragments that specifically agonize the CD40/CD40L binding interaction. In one preferred embodiment the agonistic CD40 antibody will comprise a chimeric, fully human or humanized CD40 antibody. In another preferred embodiment the agonistic CD40 antibody will comprise a chimeric, fully human or humanized CD40 antibody.

An "agonist" combines with a receptor on a cell and initiates a reaction or activity that is similar to or the same as that initiated by a natural ligand of the receptor. An "CD40 agonist" induces any or all of, but not limited to, the following responses: B cell proliferation and/or differentiation; upregulation of intercellular adhesion via such molecules as ICAM-1, E-selectin, VC AM, and the like; secretion of pro-inflammatory cytokines such as IL-1, IL-6, IL-8, IL-12. TNF, and the like; signal transduction through the CD40 receptor by such pathways as TRAF {e.g., TRAF2 and/or TRAF3), MAP kinases such as NIK (NF-kB inducing kinase), I-kappa B kinases (IKK/.beta), transcription factor NF-kB, Ras and the MEK/ERK pathway, the PI3K AKT pathway, the P38 MAPK pathway, and the like; transduction of an anti-apoptotic signal by such molecules as XIAP, mcl-1, bcl-x, and the like; B and/or T cell memory generation; B cell antibody production; B cell isotype switching, up-regulation of cell-surface expression of MHC Class II and CD80/86, and the like.

By agonist activity is intended an agonist activity of at least 30%, 10 35%, 40%, 45%, 50%, 60%, 70%, 75%, 80%, 85%, 90%, 95%, or 100% greater than the agonist activity induced by a negative control as measured in an assay of a B cell response.

In one preferred embodiment an CD40 agonist has an agonist activity that is at least 2-fold greater or at least 3-fold greater than the agonist activity induced by a negative control as measured in an assay of a B cell response.

Thus, for example, where the B cell response of interest is B cell proliferation, agonist activity would be induction of a level of B cell proliferation that is at least 2-fold greater or at least 3-fold greater than the level of B cell proliferation induced by a negative control.

In one embodiment, an antibody that does not bind to CD40 serves as the negative control. A substance "free of significant agonist activity" would exhibit an agonist activity of not more than about 25% greater than the agonist activity induced by a negative control, preferably not more than about 20% greater, 15% greater, 10% greater, 5% greater, 1% greater, 0.5% greater, or even not more than about 0.1% greater than the agonist activity induced by a negative control as measured in an assay of a B cell response.

An "agonistic CD40 antibody", or "activating CD40antibody" or "agonistic or activating anti-CD40 antibody" as used herein means an antibody that binds to human CD40 and that increases one or more CD40 activities by at least about 20% when added to a cell, tissue or organism expressing CD40. In some embodiments, the antibody activates CD40 activity by at least 40%, 50%, 60%, 70%, 80%, 85%.

In some embodiments, the activating antibody is added in the presence of CD40L.

In another preferred embodiment, the agonist activity of the agonistic CD40 antibody is measured as follows:
Increase of Immunogenicity of Cell Line Jy by Anti-CD40 Antibodies CD40 positive JIYOYE cells (ATCC CCL 87) ("Jy cells") were cultured and maintained in RPMI medium. JIYOYE cells were incubated for 24 hours with an anti-CD40 antibody of the invention (21.4.1), or with an isotype matched antibody (anti-KLH), in complete RPMI medium. Cells were then washed and treated with 25 mg mitomycin C (Sigma)/7 ml media for 60 min. These cells were then incubated with isolated human T cells at a 1:100 ratio for 6 days at 37 deg. C. (5% CO2). T cells were then collected, washed, and the level of CTL activity determined against fresh chromium 51 (New England Nuclear, Boston, Mass.) labeled JIYOYE cells. Specific CTL activity was calculated as % specific cytolysis=(cytolysis Jy (cpm)-spontaneous cytolysis (cpm))/(total cytolysis (cpm)-spontaneous cytolysis (cpm)).

In one preferred embodiment the agonistic CD40 antibody as used herein inreases immunogenicity in CD40 positive JIYOYE cells (ATCC CCL 87) by at least 50% as measured in (above described) in vitro JIYOYE cells (ATCC CCL 87) assay.

Agonistic CD40 antibodies also named anti-CD40 activating antibodies herein can contribute to tumor eradication via several important mechanisms. Foremost among these is activation of host dendritic cells for enhanced tumor antigen processing and presentation, as well as enhanced antigen presentation or immunogenicity of CD40 positive tumor cells themselves, leading to activation of tumor specific CD4+ and CD8+ lymphocytes. Additional antitumor activity can be mediated by other immune-enhancing effects of CD40 signaling (production of chemokines and cytokines, recruitment and activation monocytes, and enhanced CTL and NK cytolytic activity), as well as direct killing of CD40+ tumors by induction of apoptosis or by stimulating a humoral response leading to ADCC. Apoptotic and dying tumor cells can also become an important source of tumor-specific antigens that are processed and presented by CD40 activated APCs.

The present invention describes an isolated antibody or antigen-binding portion thereof that binds human CD40 and acts as a CD40 agonist.

Agonistic CD40 antibodies are described e.g. Beatty et al., Science 331 (2011) 1612-1616, R. H. Vonderheide et al., J Clin Oncol 25, 876 (2007); Khalil, M. et al., Update Cancer Ther. 2007 June 1; 2(2): 61-65, an agonist CD40 rat anti-mouse IgG2a mAb FGK45 as model antibody is described in S. P. Schoenberger, et al, Nature 393, 480 (1998)); the mouse cross-reactive agonistic CD40 antibody Clone 1C10 is described in Santos-Argumedo L. et al., Cell Immunol. 156 (1994) 272-285 and Heath A W et al. Eur J Immunol 24 (1994) 1828-34. Examples in clinical trials are e.g. CP-870, 893 and dacetuzumab (an agonist CD40 antibody, CAS number 880486-59-9, SGN-40; humanized S2C6 antibody) (Khalil, M, et al, Update Cancer Ther. 2007 June 1; 2(2): 61-65. Another agonistic antibody is ADC-1013 from WO 2016/023960, p. 54.

In one preferred embodiment the agonistic CD40 antibody is CP-870,893 which a fully human IgG2 agonistic CD40 antibody developed by Pfizer. It binds human CD40 with a KD of $3.48 \times 10^{-10}$ M, but does not block binding of CD40L (see e.g., U.S. Pat. No. 7,338,660 or EP1476185 wherein CP-870,893 is described as antibody 21.4.1). CP-870,893 (antibody 21.4.1 of U.S. Pat. No. 7,338,660) is characterized by comprising (a) a heavy chain variable domain amino acid sequence of QVQLVQSGAEVKKP-GASVKVSCKAS GYTFTGYYMHWVRQAPGQ-GLEWMGWINPDSGGTNYAQKFQGRVTMTR DTSIS-TAYMELNRLRSDDTAVYYCARDQPLGYCTNGVCSY-FDYWGQGTL VTVSS (SEQ ID NO: 11) (which corresponds to SEQ ID NO: 42 of U.S. Pat. No. 7,338,660) (b) a light chain variable domain amino acid sequence of DIQMTQSPSSVSASVGDRVTIT-CRASQGIYSWLAWYQQKPGKAPNLLIYTA STLQSGVPSRFSGSGSGTDFTLTISSLQPEDFA-TYYCQQANIFPLTFGGGTKV EIK (SEQ ID NO: 12) (which corresponds to SEQ ID NO: 44 of U.S. Pat. No. 7,338,660); and/or having the heavy chain variable domain and light chain variable domain amino acid sequences of the antibody produced by hybridoma 21.4.1 having American Type Culture Collection (ATCC) accession number PTA-3605. Dacetuzumab and other humanized S2C6 antibodies are described in U.S. Pat. Nos. 6,946,129 and 8,303,955.

Therefore in one preferred embodiment the agonistic CD40 antibody used in the combination therapy with an anti-CSF-1R antibody is characterized by comprising (a) a heavy chain variable domain amino acid sequence of QVQLVQSGAEVKKPGASVKVSCKAS GYTFTGYYMHWVRQAPGQ-GLEWMGWINPDSGGTNYAQKFQGRVTMTR DTSIS-TAYMELNRLRSDDTAVYYCARDQPLGYC-TNGVCSYFDYWGQGTL VTVSS (SEQ ID NO: 11) (which corresponds to SEQ ID NO: 42 of U.S. Pat. No. 7,338,660) (b) a light chain variable domain amino acid sequence of DIQMTQSPSSVSASVGDRVTIT-CRASQGIYSWLAWYQQKPGKAPNLLIYTA STLQSGVPSRFSGSGSGTDFTLTISSLQPEDFA-TYYCQQANIFPLTFGGGTKV EIK (SEQ ID NO: 12) (which corresponds to SEQ ID NO: 44 of U.S. Pat. No. 7,338,660); and/or having the heavy chain variable domain and light chain variable domain amino acid sequences of the antibody produced by hybridoma 21.4.1 having American Type Culture Collection (ATCC) accession number PTA-3605. Dacetuzumab and other humanized S2C6 antibodies are described in U.S. Pat. Nos. 6,946,129 and 8,303,955.

In one preferred embodiment the agonistic CD40 antibody used in the combination therapy with an anti-CSF-1R antibody is a humanized S2C6 antibody. A humanized S2C6 antibody is e.g. based on the CDR1, 2 and 3 of the heavy and light chain variable domain of murine mAB S2C6 (deposited with the ATCC as PTA-110). The CDR1, 2 and 3 of the heavy and light chain variable domain of murine mAB S2C6 is described and disclosed U.S. Pat. No. 6,946,129. In one embodiment the agonistic CD40 antibody is dacetuzumab. In one embodiment the agonistic CD40 antibody is characterized by comprising (a) a heavy chain variable domain amino acid sequence of EVQLVESGGGLVQPGGSLRLSC AASGYSFTGYYIHWVRQAPGKGLEWVA RVIPNAGGTSYNQKFKGRFTLSVDNSKNTAY-LQMNSLRAEDTAVYYCARE GIYWWGQGTLVTVS (SEQ ID NO: 13) (b) a light chain variable domain amino acid sequence of DIQMTQSPSSLSASVGDRVTIT-CRSSQSLVHSNGNTFLHW YQQKPGKAPKL LIYTVSNRFSGVPSRFSGSGSGTDFTLTISSLQPEDFAT YFCSQTTHVPWTFGQGTKVEIKR (SEQ ID NO: 14).

In one embodiment the agonistic CD40 antibody is a human antibody. As used herein, the term "human antibody" means an antibody in which the variable and constant domain sequences are derived from human sequences. Human agonistic CD40 antibodies are described in detail in WO 03/040170 the entire disclosure of which is hereby incorporated by reference. Human antibodies provide a substantial advantage in the treatment methods of the present invention, as they are expected to minimize the immunogenic and allergic responses that are associated with use of non-human antibodies in human patients.

Other Exemplary human anti-CD40 antibodies useful for the present invention include antibodies having the amino acid sequences of antibodies designated 3.1.1, 3.1.1 H-A78T, 3.1.1 H-A78T-V88A-V97A, 7.1.2, 10.8.3, 15.1.1, 21.4.1, 21.2.1, 22.1.1, 22.1.1 H-C109A, 23.5.1, 23.25.1, 23.28.1, 23.28.1H-D16E, 23.29.1, 24.2.1, 3.1.1H-A78T-V88A-V97A/3.1.1L-L4M-L83V and 23.28.1L-C92A, described in WO03/040170 as well as an antibody comprising a CDR or variable region of any of the exemplary antibodies.

In one embodiment of the invention the antibody which binds to human CSF-1R used in the combination therapy described herein is characterized in comprising
a) a heavy chain variable domain VH of SEQ ID NO:1 and a light chain variable domain VL of SEQ ID NO:2, or
b) a heavy chain variable domain VH of SEQ ID NO:3 and a light chain variable domain VL of SEQ ID NO:4, or
c) a heavy chain variable domain VH of SEQ ID NO:5 and a light chain variable domain VL of SEQ ID NO:6, or
d) a heavy chain variable domain VH of SEQ ID NO:7 and a light chain variable domain VL of SEQ ID NO:8, or
e) a heavy chain variable domain VH of SEQ ID NO:9 and a light chain variable domain VL of SEQ ID NO: 10; and
the agonistic CD40 antibody used in the combination therapy is characterized in comprising
a) a heavy chain variable domain VH of SEQ ID NO:11 and a light chain variable domain VL of SEQ ID NO: 12, or In one preferred embodiment of the invention the antibody which binds to human CSF-1R used in the combination therapy described herein is characterized in comprising a heavy chain variable domain VH of SEQ ID NO:5 and a light chain variable domain VL of SEQ ID NO:6, and
the agonistic CD40 antibody used in the combination therapy is characterized in comprising
a heavy chain variable domain VH of SEQ ID NO: 11 and a light chain variable domain VL of SEQ ID NO: 12.

In certain embodiments, the cancer or tumor treatment inhibits cancer cell proliferation, inhibits or prevents an increase in tumor weight or volume, and/or causes a decrease in tumor weight or volume. In some embodiments, the cancer treatment prolongs patient survival. In certain embodiments, tumor growth is inhibited at least 50%, 55%, 60%, 65%, 70% or 75%, compared to those not treated. In some embodiments, the cancer or tumor is CD40 positive.

In the present invention the term "CD40L" or "CD154" as it alternatively known in the art includes all mammalian CD40L's, e.g., human, rat, non-human primate, murine as well as fragments, variants, oligomers, and conjugates thereof that bind to at least the corresponding mammalian CD40 polypeptide, e.g., human CD40. In the present invention the administered CD40L may comprise a CD40L polypeptide or a DNA encoding said CD40L polypeptide. Such CD40L polypeptides and DNAs include in particular native CD40L sequences and fragments, variants, and oligomers thereof as disclosed in Immunex U.S. Pat. Nos. 6,410,711; 6,391,637; 5,981,724; 5,961,974 and US published application No. 20040006006 all of which patents and application and the CD40L sequences disclosed therein are incorporated by reference in their entirety herein.

The CD40L polypeptide can be used as CD40 agonist according to the invention and includes in particular native CD40L sequences and fragments, variants, and oligomers thereof as disclosed in Immunex U.S. Pat. Nos. 6,410,711; 6,391,637; 5,981,724; 5,961,974 and US published application No. 20040006006 all of which patents and application and the CD40L sequences disclosed therein are incorporated by reference in their entirety herein.

PD-1/PD-L1/PD-L2 Pathway:

An important negative co-stimulatory signal regulating T cell activation is provided by programmed death—1 receptor (PD-1)(CD279), and its ligand binding partners PD-L1 (B7-H1, CD274; SEQ ID NO: 31) and PD-L2 (B7-DC, CD273). The negative regulatory role of PD-1 was revealed by PD-1 knock outs (Pdcdl−/−), which are prone to autoimmunity. Nishimura et al., Immunity 11: 141-51 (1999); Nishimura et al., Science 291: 319-22 (2001). PD-1 is related to CD28 and CTLA-4, but lacks the membrane proximal cysteine that allows homodimerization. The cytoplasmic domain of PD-1 contains an immunoreceptor tyrosine-based inhibition motif (ITIM, V/IxYxxL/V). PD-1 only binds to PD-L1 and PD-L2. Freeman et al., J. Exp. Med. 192: 1-9 (2000); Dong et al., Nature Med. 5: 1365-1369 (1999); Latchman et al., Nature Immunol. 2: 261-268 (2001); Tseng et al., J. Exp. Med. 193: 839-846 (2001).

PD-1 can be expressed on T cells, B cells, natural killer T cells, activated monocytes and dendritic cells (DCs). PD-1 is expressed by activated, but not by unstimulated human CD4+ and CD8+ T cells, B cells and myeloid cells. This stands in contrast to the more restricted expression of CD28 and CTLA-4. Nishimura et al., Int. Immunol. 8: 773-80 (1996); Boettler et al., J. Virol. 80: 3532-40 (2006). There are at least 4 variants of PD-1 that have been cloned from activated human T cells, including transcripts lacking (i) exon 2, (ii) exon 3, (iii) exons 2 and 3 or (iv) exons 2 through 4. Nielsen et al., Cell. Immunol. 235: 109-16 (2005). With the exception of PD-1 Δex3, all variants are expressed at similar levels as full length PD-1 in resting peripheral blood mononuclear cells (PBMCs). Expression of all variants is significantly induced upon activation of human T cells with anti-CD3 and anti-CD28. The PD-1 Δex3 variants lacks a transmembrane domain, and resembles soluble CTLA-4, which plays an important role in autoimmunity. Ueda et al., Nature 423: 506-11 (2003). This variant is enriched in the synovial fluid and sera of patients with rheumatoid arthritis. Wan et al., J. Immunol. 177: 8844-50 (2006).

The two PD-1 ligands differ in their expression patterns. PD-L1 is constitutively expressed on mouse T and B cells, CDs, macrophages, mesenchymal stem cells and bone marrow-derived mast cells. Yamazaki et al., J. Immunol. 169: 5538-45 (2002). PD-L1 is expressed on a wide range of nonhematopoietic cells (e.g., cornea, lung, vascular epithelium, liver nonparenchymal cells, mesenchymal stem cells, pancreatic islets, placental synctiotrophoblasts, keratinocytes, etc.) [Keir et al., Annu. Rev. Immunol. 26: 677-704 (2008)], and is upregulated on a number of cell types after activation. Both type I and type II interferons IFN's) upregulate PD-L1. Eppihimer et al., Microcirculation 9: 133-45 (2002): Schreiner et al., J. Neuroimmunol. 155: 172-82 (2004). PD-L1 expression in cell lines is decreased when MyD88, TRAF6 and MEK are inhibited. Liu et al., Blood 110: 296-304 (2007). JAK2 has also been implicated in PD-L1 induction. Lee et al., FEBS Lett. 580: 755-62 (2006): Liu et al., Blood 110: 296-304 (2007). Loss or inhibition of phosphatase and tensin homolog (PTEN), a cellular phosphatase that modified phosphatidylinositol 3-kinase (PI3K) and Akt signaling, increased post-transcriptional PD-L1 expression in cancers. Parsa et al., Nat. Med. 13: 84-88 (2007).

PD-L2 expression is more restricted than PD-L1. PD-L2 is inducibly expressed on DCs, macrophages, and bone marrow-derived mast cells. PD-L2 is also expressed on about half to two-thirds of resting peritoneal B1 cells, but not on conventional B2 B cells. Zhong et al., Eur. J. Immunol. 37: 2405-10 (2007). PD-L2+B1 cells bind phosphatidylcholine and may be important for innate immune responses against bacterial antigens. Induction of PD-L2 by IFN-gamma is partially dependent upon NF-κB. Liang et al., Eur. J. Immunol. 33: 2706-16 (2003). PD-L2 can also be induced on monocytes and macrophages by GM-CF, IL-4 and IFN-gamma. Yamazaki et al., J. Immunol. 169: 5538-45 (2002); Loke et al., PNAS 100:5336-41 (2003).

PD-1 signaling typically has a greater effect on cytokine production than on cellular proliferation, with significant effects on IFN-gamma. TNF-alpha and IL-2 production. PD-1 mediated inhibitory signaling also depends on the strength of the TCR signaling, with greater inhibition delivered at low levels of TCR stimulation. This reduction can be overcome by costimulation through CD28 [Freeman et al., J. Exp. Med. 192: 1027-34 (2000)] or the presence of IL-2 [Carter et al., Eur. J. Immunol. 32: 634-43 (2002)].

Evidence is mounting that signaling through PD-L and PD-L2 may be bidirectional. That is, in addition to modifying TCR or BCR signaling, signaling may also be delivered back to the cells expressing PD-L and PD-L2. While treatment of dendritic cells with a naturally human anti-PD-L2 antibody isolated from a patient with Waldenstrom's macroglobulinemia was not found to upregulate MHC II or B7 costimulatory molecules, such cells did produce greater amount of proinflammatory cytokines, particularly TNF-alpha and IL-6, and stimulated T cell proliferation. Nguyen et al., J. Exp. Med. 196: 1393-98 (2002). Treatment of mice with this antibody also (1) enhanced resistance to transplanted bl6 melanoma and rapidly induced tumor-specific CTL. Radhakrishnan et al., J. Immunol. 170: 1830-38 (2003); Radhakrishnan et al., Cancer Res. 64: 4965-72 (2004); Heckman et al., Eur. J. Immunol. 37: 1827-35 (2007); (2) blocked development of airway inflammatory disease in a mouse model of allergic asthma. Radhakrishnan et al., J. Immunol. 173: 1360-65 (2004); Radhakrishnan et al., J. Allergy Clin. Immunol. 116: 668-74 (2005).

Further evidence of reverse signaling into dendritic cells ("DC's") results from studies of bone marrow derived DC's cultured with soluble PD-1 (PD-1 EC domain fused to Ig constant region—"s-PD-1"). Kuipers et al., Eur. J. Immunol. 36: 2472-82 (2006). This sPD-1 inhibited DC activation and increased IL-10 production, in a manner reversible through administration of anti-PD-1.

Additionally, several studies show a receptor for PD-L1 or PD-L2 that is independent of PD-1. B7.1 has already been identified as a binding partner for PD-L1. Butte et al., Immunity 27: 111-22 (2007). Chemical crosslinking studies suggest that PD-L1 and B7.1 can interact through their IgV-like domains. B7.1:PD-L1 interactions can induce an inhibitory signal into T cells. Ligation of PD-L1 on CD4+ T cells by B7.1 or ligation of B7.1 on CD4+ T cells by PD-L1 delivers an inhibitory signal. T cells lacking CD28 and CTLA-4 show decreased proliferation and cytokine production when stimulated by anti-CD3 plus B7.1 coated beads. In T cells lacking all the receptors for B7.1 (i.e., CD28, CTLA-4 and PD-L), T cell proliferation and cytokine production were no longer inhibited by anti-CD3 plus B7.1 coated beads. This indicates that B7.1 acts specifically through PD-L1 on the T-cell in the absence of CD28 and CTLA-4. Similarly, T cells lacking PD-1 showed decreased proliferation and cytokine production when stimulated in the presence of anti-CD3 plus PD-L1 coated beads, demonstrating the inhibitory effect of PD-L1 ligation on B7.1 on T cells. When T cells lacking all known receptors for PD-L (i.e., no PD-1 and B7.1), T cell proliferation was no longer impaired by anti-CD3 plus PD-L1 coated beads. Thus, PD-L1 can exert an inhibitory effect on cells either through B7.1 or PD-1.

The direct interaction between B7.1 and PD-L1 suggests that the current understanding of costimulation is incomplete, and underscores the significance to the expression of these molecules on T cells. Studies of PD-L−/− T cells indicate that PD-L1 on T cells can downregulate T cell cytokine production. Latchman et al., Proc. Natl. Acad. Sci. USA 101: 10691-96 (2004). Because both PD-L and B7.1 are expressed on T cells, B cells, DCs and macrophages, there is the potential for directional interactions between B7.1 and PD-L1 on these cells types. Additionally, PD-L on non-hematopoietic cells may interact with B7.1 as well as PD-1 on T cells, raising the question of whether PD-L1 is involved in their regulation. One possible explanation for the inhibitory effect of B7.1:PD-L1 interaction is that T cell PD-L1 may trap or segregate away APC B7.1 from interaction with CD28.

As a result, the antagonism of signaling through PD-L1, including blocking PD-L1 from interacting with either PD-1, B7.1 or both, thereby preventing PD-L1 from sending a negative co-stimulatory signal to T-cells and other antigen presenting cells is likely to enhance immunity in response to infection (e.g., acute and chronic) and tumor immunity. In addition, the anti-PD-L1 antibodies of the present invention, may be combined with antagonists of other components of PD-1:PD-L1 signaling, for example, antagonist anti-PD-1 and anti-PD-L2 antibodies.

The term "human PD-L1" refers to the human protein PD-L (SEQ ID NO: 31, PD-1 signaling typically). As used herein. "binding to human PD-L1" or "specifically binding to human PD-Li" or "which binds to human PD-Li" or "anti-PD-L antibody" or "antagonistic anti-PD-L1" refers to an antibody specifically binding to the human PD-L1 antigen with a binding affinity of KD-value of $1.0 \times 10^{-8}$ mol/l or lower, in one embodiment of a KD-value of $1.0 \times 10^{-9}$ mol/l or lower. The binding affinity is determined with a standard binding assay, such as surface plasmon resonance technique (BIAcore®, GE-Healthcare Uppsala, Sweden). Thus an "antibody binding to human PD-L1" as used herein refers to an antibody specifically binding to the human PD-L1 antigen with a binding affinity of KD $1.0 \times 10^{-8}$ mol/l or lower (in one embodiment $1.0 \times 10^{-8}$ mol/l-$1.0 \times 10^{-13}$ mol/l), in on embodiment of a KD $1.0 \times 10^{-9}$ mol/l or lower (in one embodiment $1.0 \times 10^{-9}$ mol/l-$1.0 \times 10^{-13}$ mol/l).

In one embodiment the antibody which binds to human PD-L1 used in the combination therapy described herein is atezolizumab is characterized in comprising the following VH and VL sequences as described herein:

TABLE 2

| anti-PD-L1 antibody | amino acid sequence of the heavy chain variable domain VH, SEQ ID NO: | amino acid sequence of the light chain variable domain VL, SEQ ID NO: |
| --- | --- | --- |
| atezolizumab | 15 | 16 |

In one embodiment of the invention the antibody which binds to human CSF-1R used in the combination therapy described herein is characterized in comprising
a) a heavy chain variable domain VH of SEQ ID NO:1 and a light chain variable domain VL of SEQ ID NO:2, or
b) a heavy chain variable domain VH of SEQ ID NO:3 and a light chain variable domain VL of SEQ ID NO:4, or
c) a heavy chain variable domain VH of SEQ ID NO:5 and a light chain variable domain VL of SEQ ID NO:6, or
d) a heavy chain variable domain VH of SEQ ID NO:7 and a light chain variable domain VL of SEQ ID NO:8, or
e) a heavy chain variable domain VH of SEQ ID NO:9 and a light chain variable domain VL of SEQ ID NO: 10: and
the antibody which binds to human PD-L1 used in the combination therapy is characterized in comprising
a) a heavy chain variable domain VH of SEQ ID NO:15 and a light chain variable domain VL of SEQ ID NO:16, or In one preferred embodiment of the invention the antibody which binds to human CSF-1R used in the combination therapy described herein is characterized in comprising a heavy chain variable domain VH of SEQ ID NO:5 and a light chain variable domain VL of SEQ ID NO:6, and
the antibody which binds to human PD-L1 used in the combination therapy is characterized in comprising
a heavy chain variable domain VH of SEQ ID NO: 15 and a light chain variable domain VL of SEQ ID NO: 16.

TLRs and Toll-Like Receptor (TLR) Ligands Especially TLR9 and TLR9 Agonists

Different experimental Toll-like receptor agonists for cancer therapy are described (Galluzzi et al., OncoImmunology, 1:5, (2012) 699-716) Toll-like receptors (TLRs) in general are prototypic pattern recognition receptors (PRRs) best known for their ability to activate the innate immune system in response to conserved microbial components such as lipopolysaccharide and double-stranded RNA. Accumulating evidence indicates that the function of TLRs is not restricted to the elicitation of innate immune responses against invading pathogens. TLRs have indeed been shown to participate in tissue repair and injury-induced regeneration as well as in adaptive immune responses against cancer. In particular, TLR4 signaling appears to be required for the efficient processing and cross-presentation of cell-associated tumor antigens by dendritic cells, which de facto underlie optimal therapeutic responses to some anticancer drugs. Thus, TLRs constitute prominent therapeutic targets for the activation/intensification of anticancer immune responses. In line with this notion, long-used preparations such as the Coley toxin (a mixture of killed *Streptococcus pyogenes* and *Serratia marcescens* bacteria) and the *bacillus* Calmette-Gudrin (BCG, an attenuated strain of *Mycobacterium bovis* originally developed as a vaccine against tuberculosis), both of which have been associated with consistent anticancer responses, potently activate TLR2 and TLR4 signaling.

According to currently accepted models, TLRs operate as homo- or hetero-dimers and are expressed either at the plasma membrane (TLRs that mainly bind proteo-lipidic MAMPs, i.e., TLR1, TLR2, TLR4, TLR5, TLR6 and TLR10) or in endosomes (TLRs that detect microbial nucleic acids, i.e., TLR3, TLR7, TLR8, TLR9). TLR10, which is the only orphan receptor among human TLRs, has also been shown to co-localize with TLR2 at phagosomes, suggesting that it may share with TLR2 the ability to bind acylated lipopeptides. Conclusive data on this issue, however, have not yet been reported. TLR11-13 are not encoded in the human genome. In mice, TLR11-13 are constitutively expressed in the central nervous system and undergo several-fold induction in response to cysticercosis.21 TLR1 reportedly recognizes a profilin-like protein expressed by *Toxoplasma gondii* and has been localized at the endoplasmic reticulum. TLR13 also appears to be localized intracellularly, where it would specifically detect the vesicular stomatitis virus. So far, the ligand specificity and intracellular localization of TLR12 remain unexplored.

So in summary the different Toll-like receptors have different functions, structure and expression patterns. Consequently also their ligands and agonist have different functions and mode of action. E.g. LPS, the natural ligand of TLR2 and TLR4 also known as endotoxin, has anticancer properties which have been discovered as early as in the 1960s, when the existence of TLRs was not even suspected.

Toll-like receptors (TLRs) are a class of proteins that play a key role in the innate immune system. They are single, membrane-spanning, non-catalytic receptors usually expressed in sentinel cells such as macrophages and dendritic cells, that recognize structurally conserved molecules derived from microbes. Once these microbes have breached physical barriers such as the skin or intestinal tract mucosa, they are recognized by TLRs, which activate immune cell responses. The TLRs include TLR1, TLR2, TLR3. TLR4, TLR5, TLR6, TLR7, TLR8, TLR9, TLR10, TLR11, TLR12, and TLR13, though the latter two are not found in humans. (Mahla, R S, et al, Front Immunol 4 (2013) 248.

TLR Ligands:

Because of the specificity of toll-like receptors (and other innate immune receptors) they cannot easily be changed in the course of evolution, these receptors recognize molecules that are constantly associated with threats (i.e., pathogen or cell stress) and are highly specific to these threats (i.e., cannot be mistaken for self molecules that are normally expressed under physiological conditions). Pathogen-associated molecules that meet this requirement are thought to be critical to the pathogen's function and difficult to change through mutation; they are said to be evolutionarily conserved. Somewhat conserved features in pathogens include bacterialcell-surface lipopolysaccharides (LPS), lipoproteins, lipopeptides, and lipoarabinomannan; proteins such as flagellin from bacterial flagella; double-stranded RNA of viruses; or the unmethylated CpG islands of bacterial and viral DNA; and also of the CpG islands found in the promoters of eukaryotic DNA; as well as certain other RNA and DNA molecules. For most of the TLRs, ligand recognition specificity has now been established by gene targeting (also known as "gene knockout"): a technique by which individual genes may be selectively deleted in mice See the table below for a summary of known TLR ligands (Waltenbaugh C, et al Immunology. Lippincott's Illustrated reviews. Philadelphia: Wolters Kluwer Health/Lippincott Williams & Wilkins. (2008) p. 17).

TABLE 3

| Receptor | Ligand(s) | Ligand location | Adapter(s) | Location | Cell types |
|---|---|---|---|---|---|
| TLR 1 | multiple triacyl lipopeptides | Bacterial lipoprotein | MyD88/ MAL | cell surface | monocytes/ macrophages a subset of dendritic cells B lymphocytes |
| TLR 2 | multiple glycolipids | Bacterial peptidoglycans | MyD88/ MAL | cell surface | monocytes/ macrophages neutrophils[17] Myeloid dendritic cells[18] Mast cells |
|  | multiple lipopeptides | Bacterial peptidoglycans |  |  |  |
|  | multiple lipoproteins | Bacterial peptidoglycans |  |  |  |
|  | lipoteichoic acid | Gram-positive bacteria |  |  |  |
|  | HSP70 | Host cells |  |  |  |
|  | zymosan (Beta-glucan) Numerous others | Fungi |  |  |  |
| TLR 3 | double-stranded RNA, poly I:C | viruses | TRIF | cell compartment | Dendritic cells B lymphocytes |
| TLR 4 | lipopolysaccharide | Gram-negative bacteria | MyD88/ MAL/TRIF/ TRAM | cell surface | monocytes/ macrophages neutrophils[17] Myeloid dendritic cells[18] Mast cells B lymphocytes[19] Intestinal epithelium Breast cancer cells |
|  | several heat shock proteins | Bacteria and host cells |  |  |  |
|  | fibrinogen | host cells |  |  |  |
|  | heparan sulfate fragments | host cells |  |  |  |
|  | hyaluronic acid fragments | host cells |  |  |  |
|  | nickel Various opioid drugs |  |  |  |  |
| TLR 5 | Bacterial flagellin | Bacteria | MyD88 | cell surface | monocyte/ macrophages a subset of dendritic cells Intestinal epithelium Breast cancer cells |
|  | Profilin[20] | Toxoplasma gondii |  |  |  |
| TLR 6 | multiple diacyl lipopeptides | Mycoplasma | MyD88/ MAL | cell surface | monocytes/ macrophages Mast cells B lymphocytes |

TABLE 3-continued

| Receptor | Ligand(s) | Ligand location | Adapter(s) | Location | Cell types |
|---|---|---|---|---|---|
| TLR 7 | imidazoquinoline loxoribine (a guanosine analogue) bropirimine single-stranded RNA | small synthetic compounds RNA viruses | MyD88 | cell compartment | monocytes/ macrophages Plasmacytoid dendritic cells[18] B lymphocytes |
| TLR 8 | small synthetic compounds; single-stranded Viral RNA, phagocytized bacterial RNA(24) | | MyD88 | cell compartment | monocytes/ macrophages a subset of dendritic cells Mast cells Intestinal epithelial cells (IECs) *only in Crohn's or Ulcerative Colitis |
| TLR 9 | unmethylated CpG Oligodeoxynucleotide DNA | Bacteria, DNA viruses | MyD88 | cell compartment | monocytes/ macrophages Plasmacytoid dendritic cells[18] B lymphocytes |
| TLR 10 | unknown | | unknown | ? | |
| TLR 11 | Profilin | Toxoplasma gondii | MyD88 | cell compartment[22] | monocytes/ macrophages liver cells kidney urinary bladder epithelium |
| TLR 12 | Profilin | Toxoplasma gondii | MyD88 | | Neurons[24] plasmacytoid dendritic cells conventional dendritic cells macrophages |
| TLR 13 | bacterial ribosomal RNA sequence "CGGAAAGACC" | Virus, bacteria | MyD88, TAK-1 | cell compartment | monocytes/ macrophages conventional dendritic cells |

The stereotypic inflammatory response provoked by toll Like-Receptor activation has prompted speculation that endogenous activators of toll-like receptors might participate in autoimmune diseases. TLRs have been suspected of binding to host molecules including fibrinogen (involved in blood clotting), heat shock proteins (HSPs), HMGB1, extracellular matrix components and self DNA (it is normally degraded by nucleases, but under inflammatory and autoimmune conditions it can form a complex with endogenous proteins, become resistant to these nucleases and gain access to endosomal TLRs as TLR7 or TLR9). These endogenous ligands are usually produced as a result of non-physiological cell death (Kawai. T. et al; Nature Immunology. 11 (2010) 373-384.

Short overview: ligands for the different TLRs.
TLR-1:—Bacterial lipoprotein and peptidoglycans
TLR-2:—Bacterial peptidoglycans
TLR-3:—Double stranded RNA
TLR-4:—Lipopolysaccharides
TLR-5:—Bacterial flagella
TLR-6:—Bacterial lipoprotein
TLR-7:—Single stranded RNA, bacterial and viral
TLR-8:—Single stranded RNA, bacterial and viral, phagocytized bacterial RNA. [30]
TLR-9:—CpG DNA
TLR-10:—Unknown
TLR-11:—Profilin from *Toxoplasma gondii*, also possibly uropathogenic bacteria
TLR-12:—Profilin from *Toxoplasma gondii*
TLR-13:—bacterial ribosomal RNA TLR9 is mainly found in the endosomal compartment of B cells, monocytes, macrophages and plasmacytoid Dendritic Cells DCs (Galluzzi et al., OncoImmunology, 1:5, (2012) 699-716). The main ligand of TLR9 is bacterial/viral DNA, differing from its mammalian counterpart for the elevated frequency of unmethylated CpG oligodeoxynucleotides. Indeed, whereas mammalian DNA has no immunostimulatory activity, the administration of bacterial/viral DNA induces a potent Th1 immune response in vivo, which is entirely abrogated in TLR9$^{-/-}$ mice. CpG oligodeoxynucleotides (or CpG ODN) are short single-stranded synthetic DNA molecules that contain a cytidine triphosphate deoxynucleotide ("C") followed by a guanidine triphosphate deoxynucleotide ("G"). The "p" refers to the phosphodiester link between consecutive nucleotides, although some ODN have a modified phosphorothioate (PS) backbone instead. When these CpG motifs are unmethlyated, they act as immunostimulants (Weiner. G J; et al, PNAS 94 (1997) 10833-7).

CpG motifs are considered pathogen-associated molecular patterns (PAMPs) due to their abundance in microbial genomes but their rarity in vertebrate genomes (Bauer, S; Current Topics in Microbiology and Immunology 270 (2002) 145-54). The CpG PAMP is recognized by the pattern recognition receptor (PRR) Toll-Like Receptor 9 (TLR9), which is constitutively expressed only in B cells and plasmacytoid dendritic cells (pDCs) in humans and other higher primates (Rothenfusser, S; et al, Human immunology 63 (2002) 1111-9)

Synthetic CpG ODN differ from microbial DNA in that they have a partially or completely phosphorothioated (PS) backbone instead of the typical phosphodiester backbone and a poly G tail at the 3' end, 5' end, or both. PS modification protects the ODN from being degraded by nucleases such as DNase in the body and poly G tail enhances cellular uptake (Dalpke, A H et al, Immunology 106 (2002) 102-12). The poly G tails form intermolecular tetrads that result in high molecular weight aggregates. These aggregates are responsible for the increased activity the poly G sequence impart; not the sequence itself.

These synthetic oligodeoxynucleotides containing unmethylated CpG motifs (CpG ODNs), such as ODN 1826, have been extensively studied as adjuvants (Steinhagen F. et al., 2011; Vaccine 29(17):3341-55). These CpG motifs are present at a 20-fold greater frequency in bacterial DNA compared to mammalian DNA (Hemmi H. et al., 2000. Nature 408: 740-5). CpG ODNs agonize TLR9, which is expressed on human B cells and plasmacytoid dendritic cells (pDCs), thereby inducing Th1-dominated immune responses (Coffman et al., 2010. Immunity 33(4):492-503). Pre-clinical studies, conducted in rodents and non-human primates, and human clinical trials have demonstrated that CpG ODNs can significantly improve vaccine-specific antibody responses (Steinhagen F. et al., 2011; Vaccine 29(17):3341-55).

Numerous sequences have been shown to stimulate TLR9 with variations in the number and location of CpG dimers, as well as the precise base sequences flanking the CpG dimers. This led to the creation of classes or categories of CpG ODN, which are all TLR9 agonist based on their sequence, secondary structures, and effect on human peripheral blood mononuclear cells (PBMCs). The three main classes of CpG ODNs are class A, B and C, which differ in their immune-stimulatory activities (Krug A. et al., 2001, Eur J Immunol, 31(7): 2154-63). Furthermore, CpG ODNs activate TLR9 in a species-specific manner (Bauer, S. et al., 2001, PNAS, 98(16):9237-42). One of the first Class A ODN, ODN 2216, was described in 2001 by Krug et al (see above) This class of ODN was distinctly different from the previously described Class B ODN (i.e., ODN 2006) in that it stimulated the production of large amounts of Type I interferons, the most important one being IFNα, and induced the maturation of pDCs.

Class A ODN are also strong activators of NK cells through indirect cytokine signaling. Class A ODN typically contain 7 to 10 PS-modified bases at one or both ends that resist degradation by nucleases and increase the longevity of the ODN. The above rules strictly define the class, but variability of the sequence within these "rules" is possible. It should also be noted that changes to the sequence will affect the magnitude of the response. For example, the internal palindrome sequence can be 4 to 8 base pairs in length and vary in the order of bases, however the pattern, 5'-Pu Pu CG Pu Py CG Py Py-3', was found to be the most active when compared to several other sequences. The poly G tail found at either end of the DNA strand can vary in length and even number, but its presence is critical to the activity of the molecule.

Class B ODN (i.e. ODN 2007) are strong stimulators of human B cell and monocyte maturation. They also stimulate the maturation of pDC but to a lesser extent than Class A ODN and very small amounts of IFNα. The strongest ODN in this class have three 6mer sequences. Class B ODNs have been studied extensively as therapeutic agents because of their ability to induce a strong humoral immune response, making them ideal as a vaccine adjuvant.

ODN 1826 is a type B CpG ODN specific for mouse TLR9. Type B CpG ODNs contain a full phosphorothioate backbone with one or more CpG dinucleotides and can strongly activate B cells (Krug A. et al., 2001, Eur J Immunol, 31(7): 2154-63). ODN 1826, a mouse-reactive surrogate TLR9-agonist has been tested as an adjuvant in numerous animal models (Bauer, S. et al., 2001, PNAS, 98(16):9237-42). Research in mice demonstrated that ODN 1826 administration can induce the activation of antigen presenting cells and type I IFN anti-viral activity 8-9, indicative of a Th1 immune response (Longhi Mp. et al., 2009, J Exp Med 206: 1589-602).

Moreover, the administration of type B CpG oligonucleotides (alone or combined with chemotherapeutics or peptide vaccines) to tumor-bearing rodents reportedly exerts potent anticancer effects. Initial Phase I/II clinical trials to test the safety and efficacy of CpG-7909 for oncological indications were launched in April 2000. Approximately in the same period, CpG-7909 begun to be extensively investigated as an adjuvant for cancer-unrelated indications (mainly antiviral vaccines), showing no severe side effects and encouraging efficacy.

During the last decade, the safety and anticancer potential of CpG-7909 (as a standalone agent or in combination with chemotherapy and/or vaccination approaches) have been investigated in a large number of Phase I/II clinical trials, including studies with leukemia, lymphoma, basal cell carcinoma, lmelanoma, esophageal squamous cell carcinoma, NSCLC, renal cell carcinoma, and prostate cancer patients. Several TLR9 agonist are known and currently developed in clinical testing Agatolimod (tricosasodium salt of a synthetic 24-mer oligonucleotide containing 3 CpG motifs; Pfizer) GNKGI68 (CpG ODN; SBI Biotech), IMO-2055 (synthetic oligonucleotide containing unmethylated CpG dinucleotides; Idera Pharmaceuticals), MGN-1703 (Mologen). Typically these TLR9 agonist are used in the treatment of different cancers:

Schroder K et al, (J Leukoc Biol. 81(6) (2007) 1577-90 relates to TLR agonist (unmethylated CpG-containing DNA (CpG DNA)) the regulation of mouse TIR9 expression and defines a molecular mechanism by which IFN-gamma amplifies mouse macrophage responses to CpG DNA.

The term "Toll-like receptor 9" (TLR9. CD289: SEQ ID NO: 32) refers to a protein of the Toll-like receptor (TLR) family which plays a fundamental role in pathogen recognition and activation of innate immunity. TLRs are highly conserved from *Drosophila* to humans and share structural and functional similarities. They recognize pathogen-associated molecular patterns (PAMPs) that are expressed on infectious agents, and mediate the production of cytokines necessary for the development of effective immunity. The various TLRs exhibit different patterns of expression. This gene is preferentially expressed in immune cell rich tissues, such as spleen, lymph node, bone marrow and peripheral blood leukocytes. Studies in mice and human indicate that this receptor mediates cellular response to unmethylated CpG dinucleotides in bacterial DNA to mount an innate immune response.

TLR9 is mainly found in the endosomal compartment of B cells, monocytes, macrophages and plasmacytoid Dendritic Cells DCs (Galluzzi et al., OncoImmunology, 1:5, (2012) 699-716). The main ligand of TLR9 is bacterial/viral DNA, differing from its mammalian counterpart for the elevated frequency of unmethylated CpG oligodeoxynucleotides. Indeed, whereas mammalian DNA has no immunostimulatory activity, the administration of bacterialiviral DNA induces a potent Th1 immune response in vivo, which is entirely abrogated in TLR9$^{-/-}$ mice. CpG oligodeoxynucleotides (or CpG ODN) are short single-stranded synthetic DNA molecules that contain a cytidine triphosphate deoxynucleotide ("C") followed by a guanidine triphosphate deoxynucleotide ("G"). The "p" refers to the phosphodiester link between consecutive nucleotides, although some ODN have a modified phosphorothioate (PS) backbone instead. When these CpG motifs are unmethylated, they act as immunostimulants (Weiner, G J; et al. PNAS 94 (1997) 10833-7). Thus "Toll-like receptor 9 agonists" (TLR9 agonist) are characterized in binding to Toll-like receptor 9 and in stimulating TLR9 immune response. E.g. in one embodiment a Toll-like receptor 9 agonist (TLR9 agonist) is characterized by binding to Toll-like receptor 9 on human plasmacytoid dendritic cells (pDCs) and by induction of IFN-alpha. IL-6, and/or IL-12 (elevating the levels of IFN-alpha, IL-6, and/or IL-12) in these plasmacytoid dendritic cells (pDCs).

CpG motifs are considered pathogen-associated molecular patterns (PAMPs) due to their abundance in microbial genomes but their rarity in vertebrate genomes (Bauer, S; Current Topics in Microbiology and Immunology 270 (2002) 145-54). The CpG PAMP is recognized by the pattern recognition receptor (PRR) Toll-Like Receptor 9 (TLR9), which is constitutively expressed only in B cells and plasmacytoid dendritic cells (pDCs) in humans and other higher primates (Rothenfusser, S; et al, Human immunology 63 (2002) 1111-9)

Synthetic CpG ODN differ from microbial DNA in that they have a partially or completely phosphorothioated (PS) backbone instead of the typical phosphodiester backbone and a poly G tail at the 3' end, 5' end, or both. PS modification protects the ODN from being degraded by nucleases such as DNase in the body and poly G tail enhances cellular uptake (Dalpke, A H et al, Immunology 106 (2002) 102-12). The poly G tails form intermolecular tetrads that result in high molecular weight aggregates. These aggregates are responsible for the increased activity the poly G sequence impart; not the sequence itself.

These synthetic oligodeoxynucleotides containing unmethylated CpG motifs (CpG ODNs), such as ODN 1826, have been extensively studied as adjuvants (Steinhagen F. et al., 2011; Vaccine 29(17):3341-55). These CpG motifs are present at a 20-fold greater frequency in bacterial DNA compared to mammalian DNA (Hemmi H. et al., 2000. Nature 408: 740-5). CpG ODNs agonize TLR9, which is expressed on human B cells and plasmacytoid dendritic cells (pDCs), thereby inducing Th1-dominated immune responses (Coffman et al., 2010. Immunity 33(4):492-503). Pre-clinical studies, conducted in rodents and non-human primates, and human clinical trials have demonstrated that CpG ODNs can significantly improve vaccine-specific antibody responses (Steinhagen F. et al., 2011; Vaccine 29(17):3341-55).

Numerous sequences have been shown to stimulate TLR9 with variations in the number and location of CpG dimers, as well as the precise base sequences flanking the CpG dimers. This led to the creation of classes or categories of CpG ODN, which are all TLR9 agonist based on their sequence, secondary structures, and effect on human peripheral blood mononuclear cells (PBMCs). The three main classes of CpG ODNs are class A, B and C, which differ in their immune-stimulatory activities (Krug A. et al., 2001, Eur J Immunol, 31(7): 2154-63). Furthermore, CpG ODNs activate TLR9 in a species-specific manner (Bauer, S. et al., 2001, PNAS, 98(16):9237-42). One of the first Class A ODN, ODN 2216, was described in 2001 by Krug et al (see above) This class of ODN was distinctly different from the previously described Class B ODN (i.e., ODN 2006) in that it stimulated the production of large amounts of Type I interferons, the most important one being IFNα, and induced the maturation of pDCs.

Class A ODN are also strong activators of NK cells through indirect cytokine signaling. Class A ODN typically contain 7 to 10 PS-modified bases at one or both ends that resist degradation by nucleases and increase the longevity of the ODN. The above rules strictly define the class, but variability of the sequence within these "rules" is possible. It should also be noted that changes to the sequence will affect the magnitude of the response. For example, the internal palindrome sequence can be 4 to 8 base pairs in length and vary in the order of bases, however the pattern, 5'-Pu Pu CG Pu Py CG Py Py-3', was found to be the most active when compared to several other sequences. The poly G tail found at either end of the DNA strand can vary in length and even number, but its presence is critical to the activity of the molecule.

Class B ODN (i.e. ODN 2007) are strong stimulators of human B cell and monocyte maturation. They also stimulate the maturation of pDC but to a lesser extent than Class A ODN and very small amounts of IFNα. The strongest ODN in this class have three 6mer sequences. Class B ODNs have been studied extensively as therapeutic agents because of their ability to induce a strong humoral immune response, making them ideal as a vaccine adjuvant.

ODN 1826 is a type B CpG ODN specific for mouse TLR9. Type B CpG ODNs contain a full phosphorothioate backbone with one or more CpG dinucleotides and can strongly activate B cells (Krug A. et al., 2001, Eur J Immunol, 31(7): 2154-63). ODN 1826, a mouse-reactive surrogate TLR9-agonist has been tested as an adjuvant in numerous animal models (Bauer, S. et al., 2001, PNAS, 98(16):9237-42). Research in mice demonstrated that ODN 1826 administration can induce the activation of antigen presenting cells and type I IFN anti-viral activity 8-9, indicative of a Th1 immune response (Longhi Mp. et al., 2009, J Exp Med 206: 1589-602).

Moreover, the administration of type B CpG oligonucleotides (alone or combined with chemotherapeutics or peptide vaccines) to tumor-bearing rodents reportedly exerts potent anticancer effects. Initial Phase I/II clinical trials to test the safety and efficacy of CpG-7909 for oncological indications were launched in April 2000. Approximately in the same period, CpG-7909 begun to be extensively investigated as an adjuvant for cancer-unrelated indications (mainly antiviral vaccines), showing no severe side effects and encouraging efficacy.

During the last decade, the safety and anticancer potential of CpG-7909 (as a standalone agent or in combination with chemotherapy and/or vaccination approaches) have been investigated in a large number of Phase I/II clinical trials, including studies with leukemia, lymphoma, basal cell carcinoma, melanoma, esophageal squamous cell carcinoma, NSCLC, renal cell carcinoma, and prostate cancer patients. Several TLR9 agonist are known and currently developed in clinical testing Agatolimod (tricosasodium salt of a synthetic 24-mer oligonucleotide containing 3 CpG motifs; Pfizer) GNKG168 (CpG ODN; SBI Biotech), IMO-2055 (synthetic oligonucleotide containing unmethylated CpG dinucleotides; Idera Pharmaceuticals), MGN-1703 (Mologen). Typically these TLR9 agonist are used in the treatment of different cancers:

Bacterial and synthetic DNA containing unmethylated CpG motifs act as agonists of TLR9 and induce Th1-type immune response profiles. The immune-stimulatory effects of TLR9 agonists are multifactorial and depend on the nucleotide sequence, the nature of the backbone and the presence of specific structural motifs. Based on the cytokine profiles induced, three distinct types of TLR9 agonists, class A, B and C, have been described. Each class of TLR9 agonist is composed of a different nucleotide sequence that allows formation of structures (or no structures) that generate different immune profiles.

The structure-activity relationships of oligonucleotides that act as agonists of TLR9 was systematically studied (Kandimalla, E. R. and Agrawal, S. (2005) in Toll and Toll Receptors: An Immunologic Perspective (Rich, T., ed.), pp. 181-212, Kluwer Academic/Plenum Publishers, New York). The presence of a CpG motif in oligonucleotides is required for TLR9 stimulation. Oligonucleotides with phosphodiester and phosphorothioate backbone stimulate TLR9-mediated immune responses. Phosphorothioate backbone oligonucleotides are commonly used because they are less susceptible to degradation by ubiquitous nucleases than are phosphodiester oligonucleotides. Introduction of a sulfur atom on the internucleotide phosphodiester bond results in the formation of Rp and Sp diastereoisomers; the Rp diastereomer of phosphorothioate linkage stimulates a stronger TLR9-mediated immune response than does the Sp diastereomer. The negative charges on phosphates between and adjacent to cytosine (C) and guanine (G) are also required for TLR9-mediated activity. Neutralization of charges by incorporation of methylphosphonate linkages at these positions results in the loss of immune-stimulatory activity. Moreover, TLR9 activation is also dependent on the sequences flanking the CpG dinucleotide, the nature of the nucleotide backbone and the secondary structures.

Flanking Sequences Play a Significant Role in TLR9 Stimulation

Chemical modifications introduced at the 2'-position of the sugar ring of a C or G nucleotide in the CpG motif result in the loss of immune-stimulatory activity of TLR9 agonists. In addition, studies of TLR9 agonists containing chemical modifications such as methylphosphonate linkages, 2'-alkyl or 3'-deoxy or -alkyl ribonucleosides, non-nucleotide linkers or abasic nucleotides in the flanking sequences indicate that substitutions incorporated at the fourth to sixth nucleotide positions 5' to the CpG dinucleotide significantly enhance immune-stimulatory activity. In general, modifications incorporated in the 3'-flanking sequence distal to the CpG dinucleotide have effects dependent on the nature of the modification.

TLR9 Requires a Free 5'-End of Agonist for Stimulation

Two CpG oligonucleotides linked through their 5'-ends do not activate immune cells despite the availability of two CpG motifs. When the same oligonucleotides are linked through their 3'-ends, they produce higher and distinct cytokine profiles than the parent CpG oligonucleotide with a single 5'-end. These are the first studies demonstrating the requirement of an accessible or free 5'-end for TLR9 activation and that the receptor reads the sequence from the 5'-end. The transcription factor NF-κB is rapidly activated by TLR9 agonists that contain two 5'-ends, but these compounds have the same activity as conventional TLR9 agonists on the MAPK (mitogen-activated protein kinase) pathway in J774 cells.

These studies suggest that agonists containing two 5'-ends facilitate dimerization of the receptor, leading to rapid activation of immune responses. Moreover, TLR9 activation can be modulated through appropriate presentation of the free 5'-ends and synthetic immune-stimulatory motifs, leading to changes in the downstream cytokine induction profiles. Consistent with these results, recent studies have shown that TLR9 exists in dimer form and binds to single-stranded oligonucleotides. However, only oligonucleotides containing the CpG motif cause conformational changes in the receptor, leading to the activation of immune signalling pathways.

The attachment of oligonucleotides through their 3'-ends not only provides two 5'-ends for optimal activation of TLR9, but also increases the stability against 3'-exonucleases. Oligonucleotides with a phosphodiester backbone and as short as 5 and 6 nt linked through their 3'-ends act as potent TLR9 agonists and produce immune responses. Moreover, oral administration of the novel structure containing TLR9 agonists induces potent mucosal immune responses, acts as an adjuvant with antigens, and prevents and reverses peanut allergy in mouse models because of their greater stability in the gastrointestinal tract.

Functional Groups of Cytosine and Guanine Required for TLR9 Stimulation

As described above, certain chemical modifications introduced within the CpG dinucleotide that alter structure and conformation lead to the loss of immune-stimulatory activity of agonists. One such modification is a replacement of the methyl group at the 5-position of cytosine in the CpG motif of TLR9 agonists. Vertebrates use this feature to distinguish self-DNA from that of bacterial DNA, which contains more unmethylated CpG motifs.

The effects of various pyrimidine analogues (Y), such as 5-OH-dC, dU, dP, 1-(2'-deoxy-β-D-ribofuranosyl)-2-oxo-7-deaza-8-methyl-purine. N3-Me-dC and N4-Et-dC, in place of cytosine (Kandimalla, E. R., et al (2001) Bioorg. Med. Chem. 9, 807-813; Kandimalla, E. R., et al, S. (2003) PNAS, 100, 14303-14308; or Putta, M. R., et al. S. (2006) Nucleic Acids Res. 34, 3231-3238). To understand the role of different functional groups of guanine in the recognition of TLR9, several purine nucleobases (R) such as 7-deaza-dG, N1-Me-dG, 2-amino-D-purine, nebularine, 2-amino-dA, 7-deaza-D-xanthine, K-base and dI were examined in place of guanine in the CpG (Kandimalla, E. R., et al (2001) Bioorg. Med. Chem. 9, 807-813; Kandimalla, E. R., et al. (2003) PNAS, 100, 14303-14308; Putta, M. R., et al, (2006) Nucleic Acids Res. 34, 3231-3238; Kandimalla, E. R., et al (2003) Nucleic Acids Res. 31, 2393-2400; or Kandimalla. ER., et al. (2005) PNAS, 102, 6925-6930). These studies led to the development of alternative synthetic nucleotide motifs (YpG, CpR) for immune modulation and have demonstrated acceptance by TLR9 of certain heterocyclic base variants.

Novel synthetic agonists of TLR9 (S. Agrawal and E. R. Kandimalla, Biochemical Society Transactions (2007) 35, (1461-1467)): The combinations of novel structures and synthetic immune-stimulatory motifs described above provided us with tools to generate combinatorial libraries of novel synthetic agonists of TLR9. Systematic studies of several TLR9 agonists that have two 5'-ends and contain synthetic CpR dinucleotides in different nucleotide compositions in mouse, human and monkey systems suggest that nucleotide sequence and secondary structures play a role in modulating the immune response. Based on these studies, we have broadly identified two different groups of synthetic agonists of TLR9.

In one embodiment the TLR9 agonist is characterized by induction of IFN-alpha, IL-6, and/or IL-12 (elevating the levels of IFN-alpha, IL-6, and/or IL-12) in plasmacytoid dendritic cells (pDCs). In one embodiment the TLR9 agonist is characterized by elevating the level of IFN-alpha in human plasmacytoid dendritic cells (pDCs) (as measured by sandwich ELISA as described below or e.g in in WO2010/088395)

Assay for Measuring IFN-Alpha Induction (Elevating the Levels of IFN-Alpha, IL-6, and/or IL-12) by TLR9 Agonist Used in the Combination Treatment of the Present Invention in Human pDCs:

Human PBMC isolation: Peripheral blood mononuclear cells (PBMCs) from freshly drawn healthy volunteer blood (CBR Laboratories, Boston, Mass.) are isolated by Ficoll density gradient centrifugation method (Histopaque-1077, Sigma).

Human pDC isolation: Human plasmacytoid dendritic cells (pDCs) are isolated from freshly obtained healthy human volunteer's blood PBMCs by positive selection using the BDC A4 cell isolation kits (Miltenyi Biotec) according to the manufacturer's instructions.

Human pDCs are plated in 96-well dishes using $1 \times 10^6$ cells/ml. Individual immune modulatory compounds from Table 1 were dissolved in DPBS (pH 7.4; Mediatech) are added to the cell cultures at doses of 0, 0.1, 0.3, 1.0, 3.0, or 10.0.micro.g/ml. The cells were then incubated at 37 (0)C for 24 hours and the supematants were collected for luminex multiplex or ELISA assays.

In the levels of IFN-alpha, IL-6, and/or IL-12 are measured by sandwich ELISA. The required reagents, including cytokine antibodies and standards, can be purchased from PharMingen.

IFN-alpha has been known as an antiviral cytokine for many years. It stimulates Th1 cell development, therefore promoting the effects of CG-containing DNA molecules. IFN-alpha also exhibits antitumour activity in mouse and human malignancies and is capable of decreasing the tumourigenicity of transplanted tumour cells, partially by activating cytotoxic T cells and thereby increasing the likelihood of tumour-cell cytolysis. NK cell and macrophage activity, both also important for antitumour cytotoxicity, are also increased by IFN-alpha (Brassard et al., J. Leukoc. Biol. 2002 71; 565-81). Therefore, increasing the amount of IFN-alpha upon stimulation with the DNA constructs of the present disclosure is expected to be beneficial for the treatment of cancer.

In one embodiment of the invention the TLR9 agonist used in the combination treatment of the present invention is a oligodeoxynucleotides containing a) cytosine-phosphate-guanosine (CpG) motifs (CpG ODNs) b) pyrimidine-phosphate-guanosine (YpG) motifs (YpG ODNs) or c) cytosine-phosphate-purine (CpR) motifs (CpR ODNs).

In one embodiment of the invention the TLR9 agonist used in the combination treatment of the present invention is a oligodeoxynucleotides containing a) cytosine-phosphate-guanosine (CpG) motifs (CpG ODNs) b) pyrimidine-phosphate-guanosine (YpG) motifs (YpG ODNs) or c) Purine-phosphate-guanosine (RpG) motifs (RpG ODNs) wherein the TLR9 agonist stimulates TLR9 (in one embodiment the TLR9 agonist induces the maturation of plasmacytoid dendritic cells (pDCs); in one embodiment the TLR9 agonist is charcterized by human B cell maturation; in one embodiment)

In one embodiment of the invention the TLR9 agonist used in the combination treatment of the present invention is a oligodeoxynucleotides containing cytosine-phosphate-guanosine (CpG) motifs (CpG ODNs).

In one embodiment of the invention the TLR9 agonist used in the combination treatment of the present invention is a Class A CpG ODN.

In one embodiment the TLR9 agonist used in the combination treatment of the present invention is a oligodeoxynucleotides comprising
a) a poly G sequence at the 5' end, or the 3' end, or at both ends
b) an internal palindrome sequence;
c) GC dinucleotides contained within the internal palindrome, and
d) a partially PS-modified backbone Class A CpG ODN typically contain 7 to 10 PS-modified bases at one or both ends that resist degradation by nucleases and increase the longevity of the ODN. The above rules strictly define the class, but variability of the sequence within these rules is possible. The internal palindrome sequence can be 4 to 8 base pairs in length and vary in the order of bases, however the pattern, 5'-Pu Pu CG Pu Py CG Py Py-3', was found to be the most active when compared to several other sequences. The poly G tail found at either end of the DNA strand can vary in length and number.

In one embodiment the Class A CpG ODN (Xueqing Liang, et al, Blood. 2010 June 17; 115(24): 5041-5052) is selected from the group consisting of CpG ODN 2216 (5'-ggGGGACGATCGTCggggG-3') (SEQ ID NO: 17) CpG ODN PB4 (5'-tcgGACGATCGTCggggG-3') (SEQ ID NO: 18); or CpG ODN 1002 (5'-ggGGTCGTTCGTCGTTggggG-3') (SEQ ID NO: 19).

In one embodiment of the invention the TLR9 agonist used in the combination treatment of the present invention is a Class B CpG ODN.

In one embodiment the TLR9 agonist used in the combination treatment of the present invention is a oligodeoxynucleotides comprising
a) one or more 6mer unmethylated cytosine-phosphate-guanosine (CpG) motifs 5'-Pu Py C G Py Pu-3' (one or more 6mer 5'-RYCGYR-3' 6-mers (R=A or G; Y=T or C))
b) a fully phosphorothioated (PS-modified) backbone; and
c) 18 to 28 nucleotides in length In one embodiment the Class B CPG ODN is selected from the group consisting of CpG-28, CpG-685 (GNKG168; CpG ODN; SBI Biotech), CpG-684 and CpG-7909 (CPG-ODN 2006, PF-3512676, Agatolimod).

CpG-7909 (CpG 2006, PF-3512676. Agatolimod) is a Synthetic, 24-mer phosphothioate oligodeoxynucleotide (d(P-Thio)T-C-G-T-C-G-T-T-T-T-G-T-C-G-T-T-T-T-G-T-C-G-T-T)DNA) (5'-tcgtcgttttgtcgtttgtcgtt-3') (SEQ ID NO: 20) containing multiple cytosine-phosphate-guanosine (CpG) motifs or one of its derivatives like tricosasodium salt. The preparation is described e.g. in WO 9818810 or U.S. Pat. No. 7,223,741)

CpG-685 (GNKG168; CpG ODN; SBI Biotech) is synthetic, 21-mer, unmethylated CpG motif-based oligodeoxynucleotide (ODN) (685, 5'-tcgtcgacgtcgttcgttctc-3') (SEQ ID NO: 21), with immunostimulatory activity. CpG685 (GNKG168), a 21-mer fully phosphorothioated oligonucleotides designed to directly target Toll-like receptor 9 that mediates cellular responses in B cells, showed antitumor effects in SCID mouse and is under clinical development for the treatment of human chronic lymphocytic leukemia (B-CLL) by SBI Biotech Co. Herein, a sensitive and specific assay was developed in plasma and cell lysate to support its preclinical pharmacology studies. CpG oligodeoxynucleotide GNKG168 binds to and activates Toll-like receptor 9 (TLR9) and is taken up into cells by endocytosis; once internalized, it may activate numerous signaling transduction pathways resulting in the release of multiple cytokines, such as immunoglobulins (Igs), interferons (IFNs), interleukins (ILs) and tumor necrosis factor (TNF).

CpG-684 is synthetic, 23-mer, unmethylated CpG motif-based oligodeoxynucleotide (ODN) 684, 5'-tcgacgttcgtcgttcgtcgttc-3' (SEQ ID NO: 22);

CpG-28 synthetic unmethylated CpG motif-based oligodeoxynucleotide (ODN), containing multiple repeats of unmethylated CpG motifs (CpG ODN) with immunostimulatory activity (5'-TAAACGTIATAACGTTATGACGT-CAT-3') (SEQ ID NO: 23) with a wholly phosphorothioate backbone (Carpentier A F, et al Front Biosci. 2003:8:e115-e127: Meng Y. et al, Int J Cancer. 2005; 116:992-997; or Carpentier A, et al. Neuro-Oncology 2006; 8:60-66). Upon entering the cell via endocytosis, CpG-28 activates numerous signaling transduction pathways resulting in the release of multiple cytokines. CpG-28 has immunomodulatory properties with direct activation of B-lymphocytes, dendritic and NK cells resulting in the stimulation of innate immunity and antibody-dependant cell cytotoxicity (ADCC). Additionally, this agent indirectly modulates T-cell responses though the release of cytokines (IL-12 and IFN gamma) to induce a preferential shift to the Th1 (helper) phenotype resulting in enhanced CD8+ cellular cytotoxicity.

In one embodiment of the invention the TLR9 agonist used in the combination treatment of the present invention is a oligodeoxynucleotides containing pyrimidine-phosphate-guanosine (YpG) motifs (YpG ODNs).

In one embodiment of the invention the TLR9 agonist used in the combination treatment of the present invention is a oligodeoxynucleotides containing cytosine-phosphate-purine (CpR) motifs (CpR ODNs).

In one embodiment of the invention the TLR9 agonist used in the combination treatment of the present invention is IMO-2055 (Idera) (ODN consisting of 3'-3'-linked structure and synthetic CpR(R=2'-deoxy-7-deazaguanosine) motif)

In one embodiment of the invention the TLR9 agonist used in the combination treatment of the present invention is a oligodeoxynucleotides containing a) cytosine-phosphate-guanosine (CpG) motifs (CpG ODNs) b) pyrimidine-phosphate-guanosine (YpG) motifs (YpG ODNs) or c) cytosine-phosphate-purine (CpR) motifs (CpR ODNs).

In one embodiment of the invention the TLR9 agonist used in the combination treatment of the present invention is a oligodeoxynucleotides based CpG motif-containing circular ODN (e.g MGN-1703 from Mologen as described in WO2012/085291) based on the dSLIM® technology (this technology is described in WO2001/07055).

In one embodiment of the invention the TLR9 agonist is selected from the group consisting of CpG ODN 2216 CpG ODN 1002 CpG-28, CpG-685, CpG-684.CpG-7909, IMO-2055 or MGN-1703. In one embodiment of the invention the TLR9 agonist is selected from the group consisting of CpG-685, CpG-7909, IMO-2055 or MGN-1703. In one embodiment the TLR9 agonist is selected from the group consisting of CpG-7909, IMO-2055 or MGN-1703.

In one embodiment of the invention the antibody which binds to human CSF-1R used in the combination therapy described herein is characterized in comprising
a) a heavy chain variable domain VH of SEQ ID NO:1 and a light chain variable domain VL of SEQ ID NO:2, or
b) a heavy chain variable domain VH of SEQ ID NO:3 and a light chain variable domain VL of SEQ ID NO:4, or
c) a heavy chain variable domain VH of SEQ ID NO:5 and a light chain variable domain VL of SEQ ID NO:6, or
d) a heavy chain variable domain VH of SEQ ID NO:7 and a light chain variable domain VL of SEQ ID NO:8, or
e) a heavy chain variable domain VH of SEQ ID NO:9 and a light chain variable domain VL of SEQ ID NO: 10:
and
the TLR9 agonist used in the combination therapy is a oligodeoxynucleotides containing a) cytosine-phosphate-guanosine (CpG) motifs (CpG ODNs) b) pyrimidine-phosphate-guanosine (YpG) motifs (YpG ODNs) or c) cytosine-phosphate-purine (CpR) motifs (CpR ODNs) (preferably a a oligodeoxynucleotides containing cytosine-phosphate-guanosine (CpG) motifs (CpG ODNs))

In one preferred embodiment of the invention the antibody which binds to human CSF-1R used in the combination therapy described herein is characterized in comprising a heavy chain variable domain VH of SEQ ID NO:5 and a light chain variable domain VL of SEQ ID NO:6,
and
the TLR9 agonist used in the combination therapy is a oligodeoxynucleotides containing a) cytosine-phosphate-guanosine (CpG) motifs (CpG ODNs) b) pyrimidine-phosphate-guanosine (YpG) motifs (YpG ODNs) or c) cytosine-phosphate-purine (CpR) motifs (CpR ODNs) (preferably a a oligodeoxynucleotides containing cytosine-phosphate-guanosine (CpG) motifs (CpG ODNs))

The term "epitope" denotes a protein determinant capable of specifically binding to an antibody. Epitopes usually consist of chemically active surface groupings of molecules such as amino acids or sugar side chains and usually epitopes have specific three dimensional structural characteristics, as well as specific charge characteristics. Conformational and nonconformational epitopes are distinguished in that the binding to the former but not the latter is lost in the presence of denaturing solvents.

The "variable domain" (light chain variable domain VL, heavy chain variable domain VH) as used herein denotes each of the pair of light and heavy chain domains which are involved directly in binding the antibody to the antigen. The variable light and heavy chain domains have the same general structure and each domain comprises four framework (FR) regions whose sequences are widely conserved, connected by three "hypervariable regions" (or complementary determining regions, CDRs). The framework regions adopt a beta-sheet conformation and the CDRs may form loops connecting the beta-sheet structure. The CDRs in each chain are held in their three-dimensional structure by the framework regions and form together with the CDRs from the other chain the antigen binding site. The antibody's heavy and light chain CDR3 regions play a particularly important role in the binding specificity/affinity of the antibodies according to the invention and therefore provide a further object of the invention.

The term "antigen-binding portion of an antibody" when used herein refer to the amino acid residues of an antibody which are responsible for antigen-binding. The antigen-binding portion of an antibody comprises amino acid residues from the "complementary determining regions" or "CDRs". "Framework" or "FR" regions are those variable domain regions other than the hypervariable region residues as herein defined. Therefore, the light and heavy chain variable domains of an antibody comprise from N- to C-terminus the domains FR1, CDR1, FR2, CDR2, FR3, CDR3, and FR4. Especially, CDR3 of the heavy chain is the region which contributes most to antigen binding and defines the antibody's properties. CDR and FR regions are determined according to the standard definition of Kabat et al., Sequences of Proteins of Immunological Interest, 5th ed., Public Health Service, National Institutes of Health, Bethesda, Md. (1991) and/or those residues from a "hypervariable loop".

The terms "nucleic acid" or "nucleic acid molecule", as used herein, are intended to include DNA molecules and RNA molecules. A nucleic acid molecule may be single-stranded or double-stranded, but preferably is double-stranded DNA.

The term "amino acid" as used within this application denotes the group of naturally occurring carboxy alpha-amino acids comprising alanine (three letter code: ala, one letter code: A), arginine (arg, R), asparagine (asn, N), aspartic acid (asp, D), cysteine (cys, C), glutamine (gln, Q), glutamic acid (glu. E), glycine (gly. G), histidine (his, H), isoleucine (ile, I), leucine (leu, L), lysine (lys, K), methionine (met, M), phenylalanine (phe. F), proline (pro, P), serine (ser, S), threonine (thr, T), tryptophan (trp, W), tyrosine (tyr, Y), and valine (val, V).

The "Fc part" of an antibody is not involved directly in binding of an antibody to an antigen, but exhibit various effector functions. A "Fc part of an antibody" is a term well known to the skilled artisan and defined on the basis of papain cleavage of antibodies. Depending on the amino acid sequence of the constant region of their heavy chains, antibodies or immunoglobulins are divided in the classes: IgA, IgD, IgE, IgG and IgM, and several of these may be further divided into subclasses (isotypes), e.g. IgG1, IgG2, IgG3, and IgG4, IgA1, and IgA2. According to the heavy chain constant regions the different classes of immunoglobulins are called α, δ, ε, γ, and μ, respectively. The Fc part of an antibody is directly involved in ADCC (antibody-dependent cell-mediated cytotoxicity) and CDC (complement-dependent cytotoxicity) based on complement activation, C1q binding and Fc receptor binding. Complement activation (CDC) is initiated by binding of complement factor C1q to the Fc part of most IgG antibody subclasses. While the influence of an antibody on the complement system is dependent on certain conditions, binding to C1q is caused by defined binding sites in the Fc part. Such binding sites are known in the state of the art and described e.g. by Boackle, R. J., et al., Nature 282 (1979) 742-743: Lukas, T. J., et al., J. Immunol. 127 (1981) 2555-2560; Brunhouse, R., and Cebra, J. J., Mol. Immunol. 16 (1979) 907-917; Burton, D. R., et al., Nature 288 (1980) 338-344; Thommesen, J. E., et al., Mol. Immunol. 37 (2000) 995-1004: Idusogie, E. E., et al., J. Immunol. 164 (2000) 4178-4184; Hezareh, M., et al., J. Virology 75 (2001) 12161-12168; Morgan. A., et al., Immunology 86 (1995) 319-324; EP 0 307 434. Such binding sites are e.g. L234, L235, D270, N297, E318, K320, K322, P331 and P329 (numbering according to EU index of Kabat, E. A., see below). Antibodies of subclass IgG. IgG2 and IgG3 usually show complement activation and C1q and C3 binding, whereas IgG4 do not activate the complement system and do not bind C1q and C3.

In one embodiment the antibody according to the invention comprises an Fc part derived from human origin and preferably all other parts of the human constant regions. As used herein the term "Fc part derived from human origin" denotes a Fc part which is either a Fc part of a human antibody of the subclass IgG1, IgG2, IgG3 or IgG4, preferably a Fc part from human IgG1 subclass, a mutated Fc part from human IgG1 subclass (in one embodiment with a mutation on L234A+L235A), a Fc part from human IgG4 subclass or a mutated Fc part from human IgG4 subclass (in one embodiment with a mutation on S228P). In one preferred embodiment the human heavy chain constant region of human IgG1 subclass, in another preferred embodiment the human heavy chain constant region is of human IgG1 subclass with mutations L234A, L235A and P329, in another preferred embodiment the human heavy chain constant region is of human IgG4 subclass, and in another preferred embodiment the human heavy chain constant region is of human IgG4 subclass with mutation S228P. In one embodiment said antibodies have reduced or minimal effector function. In one embodiment the minimal effector function results from an effectorless Fc mutation. In one embodiment the effectorless Fc mutation is L234A/L235A or L234A/L235A/P329G or N297A or D265A/N297A. In one embodiment the effectorless Fc mutation is selected for each of the antibodies independently of each other from the group comprising (consisting of) L234A/L235A. L234A/L235A/P329G, N297A and D265A/N297A.

In one embodiment the antibodies described herein are of human IgG class (i.e. of IgG1, IgG2, IgG3 or IgG4 subclass).

In a preferred embodiment the antibodies described herein are of human IgG1 subclass or of human IgG4 subclass. In one embodiment the described herein are of human IgG1 subclass. In one embodiment the antibodies described herein are of human IgG4 subclass.

In one embodiment the antibody described herein is characterized in that the constant chains are of human origin. Such constant chains are well known in the state of the art and e.g. described by Kabat. E. A., (see e.g. Johnson, G. and Wu, T. T., Nucleic Acids Res. 28 (2000) 214-218). For example, a useful human heavy chain constant region comprises an amino acid sequence of SEQ ID NO: 34. For example, a useful human light chain constant region comprises an amino acid sequence of a kappa-light chain constant region of SEQ ID NO: 33.

The invention comprises a method for the treatment of a patient in need of therapy, characterized by administering to the patient a therapeutically effective amount of an antibody according to the invention.

The invention comprises the use of an antibody according to the invention for the described therapy.

One embodiment of the invention are the CSF-1R antibodies described herein in for use in the treatment of cancer in combination with a with a macrophage activating agent selected from the group of an agonistic CD40 antibody, a Toll-like receptor (TLR) ligand, a TLR agonist, an antagonistic PD-L1 antibody as described herein One embodiment of the invention are the CSF-1R antibodies described herein in for use in the treatment of cancer in combination with an agonistic CD40 antibody as described herein.

One embodiment of the invention are the CSF-1R antibodies described herein in for use in the treatment of cancer in combination with an antagonistic PD-L1 antibody as described herein In one preferred embodiment of the invention the cancer is a solid tumor.

In another preferred embodiment of the invention the cancer is a melanoma, colorectal cancer, or mesothelioma.

The term "cancer" as used herein may be, for example, lung cancer, non small cell lung (NSCL) cancer, bronchioloalveolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwannomas, ependymomas, medulloblastomas, meningiomas, squamous cell carcinomas, pituitary adenoma, lymphoma, lymphocytic leukemia, including refractory versions of any of the above cancers, or a combination of one or more of the above cancers. In one preferred embodiment such cancer is a breast cancer, colorectal cancer, melanoma, head and neck cancer, lung cancer or prostate cancer. In one preferred embodiment such cancer is a breast cancer, ovarian cancer, cervical cancer, lung cancer or prostate cancer. In another preferred embodiment such cancer is breast cancer, lung cancer, colon cancer, ovarian cancer, melanoma cancer, bladder cancer, renal cancer, kidney cancer, liver cancer, head and neck cancer, colorectal cancer, pancreatic cancer, gastric carcinoma cancer, esophageal cancer, mesothelioma, prostate cancer, leukemia, lymphoma, myelomas. In one preferred embodiment such cancers are further characterized by CSF-1 or CSF-1R expression or overexpression. One further embodiment the invention are the CSF-1R antibodies of the present invention for use in the simultaneous treatment of primary tumors and new metastases. Thus another embodiment of the invention are the CSF-1R antibodies of the present invention for use in the treatment of periodontitis, histiocytosis X, osteoporosis, Paget's disease of bone (PDB), bone loss due to cancer therapy, periprosthetic osteolysis, glucocorticoid-induced osteoporosis, rheumatoid arthritis, psoriatic arthritis, osteoarthritis, inflammatory arthridities, and inflammation.

The antibodies described herein are preferably produced by recombinant means. Such methods are widely known in the state of the art and comprise protein expression in prokaryotic and eukaryotic cells with subsequent isolation of the antibody polypeptide and usually purification to a pharmaceutically acceptable purity. For the protein expression nucleic acids encoding light and heavy chains or fragments thereof are inserted into expression vectors by standard methods. Expression is performed in appropriate prokaryotic or eukaryotic host cells, such as CHO cells, NS0 cells. SP2/0 cells, HEK293 cells, COS cells, yeast, or E. coli cells, and the antibody is recovered from the cells (from the supernatant or after cells lysis).

Recombinant production of antibodies is well-known in the state of the art and described, for example, in the review articles of Makrides, S. C., Protein Expr. Purif 17 (1999) 183-202: Geisse, S., et al., Protein Expr. Purif. 8 (1996) 271-282; Kaufman, R. J., Mol. Biotechnol. 16 (2000) 151-161; Werner, R. G., Drug Res. 48 (1998) 870-880.

The antibodies may be present in whole cells, in a cell lysate, or in a partially purified, or substantially pure form. Purification is performed in order to eliminate other cellular components or other contaminants, e.g. other cellular nucleic acids or proteins, by standard techniques, including alkaline/SDS treatment, CsCl banding, column chromatography, agarose gel electrophoresis, and others well known in the art. See Ausubel, F., et al., ed. Current Protocols in Molecular Biology, Greene Publishing and Wiley Interscience, New York (1987).

Expression in NS0 cells is described by, e.g., Barnes, L. M., et al., Cytotechnology 32 (2000) 109-123: Barnes, L. M., et al., Biotech. Bioeng. 73 (2001) 261-270. Transient expression is described by, e.g., Durocher, Y., et al., Nucl. Acids. Res. 30 (2002) E9. Cloning of variable domains is described by Orlandi, R., et al., Proc. Natl. Acad. Sci. USA 86 (1989) 3833-3837: Carter, P., et al., Proc. Natl. Acad. Sci. USA 89 (1992) 4285-4289: Norderhaug, L., et al., J. Immunol. Methods 204 (1997) 77-87. A preferred transient expression system (HEK 293) is described by Schlaeger, E.-J. and Christensen, K., in Cytotechnology 30 (1999) 71-83, and by Schlaeger, E.-J., in J. Immunol. Methods 194 (1996) 191-199.

The heavy and light chain variable domains according to the invention are combined with sequences of promoter, translation initiation, constant region, 3' untranslated region, polyadenylation, and transcription termination to form expression vector constructs. The heavy and light chain expression constructs can be combined into a single vector, co-transfected, serially transfected, or separately transfected into host cells which are then fused to form a single host cell expressing both chains.

The control sequences that are suitable for prokaryotes, for example, include a promoter, optionally an operator sequence, and a ribosome binding site. Eukaryotic cells are known to utilize promoters, enhancers and polyadenylation signals.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

The monoclonal antibodies are suitably separated from the culture medium by conventional immunoglobulin purification procedures such as, for example, protein A-Sepharose, hydroxylapatite chromatography, gel electrophoresis, dialysis, or affinity chromatography. DNA and RNA encoding the monoclonal antibodies are readily isolated and sequenced using conventional procedures. The hybridoma cells can serve as a source of such DNA and RNA. Once isolated, the DNA may be inserted into expression vectors, which are then transfected into host cells such as HEK 293 cells, CHO cells, or myeloma cells that do not otherwise produce immunoglobulin protein, to obtain the synthesis of recombinant monoclonal antibodies in the host cells.

As used herein, the expressions "cell", "cell line", and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included.

In another aspect, the present invention provides a composition, e.g. a pharmaceutical composition, containing one or a combination of monoclonal antibodies, or the antigen-binding portion thereof, of the present invention, formulated together with a pharmaceutically acceptable carrier.

As used herein, "pharmaceutically acceptable carrier" includes any and all solvents, dispersion media, coatings, antibacterial and antifungal agents, isotonic and absorption/resorption delaying agents, and the like that are physiologically compatible. Preferably, the carrier is suitable for injection or infusion.

A composition of the present invention can be administered by a variety of methods known in the art. As will be appreciated by the skilled artisan, the route and/or mode of administration will vary depending upon the desired results.

Pharmaceutically acceptable carriers include sterile aqueous solutions or dispersions and sterile powders for the preparation of sterile injectable solutions or dispersion. The use of such media and agents for pharmaceutically active substances is known in the art. In addition to water, the carrier can be, for example, an isotonic buffered saline solution.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient (effective amount). The selected dosage level will depend upon a variety of pharmacokinetic factors including the activity of the particular compositions of the present invention employed, or the ester, salt or amide thereof, the route of administration, the time of administration, the rate of excretion of the particular compound being employed, other drugs, compounds and/or materials used in combination with the particular compositions employed, the age, sex, weight, condition, general health and prior medical history of the patient being treated, and like factors well known in the medical arts.

The term "a method of treating" or its equivalent, when applied to, for example, cancer refers to a procedure or course of action that is designed to reduce or eliminate the number of cancer cells in a patient, or to alleviate the symptoms of a cancer. "A method of treating" cancer or another proliferative disorder does not necessarily mean that the cancer cells or other disorder will, in fact, be eliminated, that the number of cells or disorder will, in fact, be reduced, or that the symptoms of a cancer or other disorder will, in fact, be alleviated. Often, a method of treating cancer will be performed even with a low likelihood of success, but which, given the medical history and estimated survival expectancy of a patient, is nevertheless deemed to induce an overall beneficial course of action.

The terms "administered in combination with" or "co-administration", "co-administering", "combination therapy" or "combination treatment" refer to the administration of the anti-CSF-1R as described herein, and the macrophage activating agent selected from the group of an agonistic CD40 antibody, a Toll-like receptor (TLR) ligand, a TLR agonist, an antagonistic PD-L1 antibody as described herein e.g. as separate formulations/applications (or as one single formulation/application). The co-administration can be simultaneous or sequential in either order, wherein there is a time period while both (or all) active agents simultaneously exert their biological activities within the respective treatment cycle in which both the anti-CSF-1R as described herein, and the with a macrophage activating agent selected from the group of an agonistic CD40 antibody, a Toll-like receptor (TLR) ligand, a TLR agonist, an antagonistic PD-L1 antibody as described herein, are coadmistered and in wherein there is a time period in the respective further treatment cycle without anti-CSF1R treatment where no biological activity of the-CSF1R antibody is exerted and the level of the tumor associated macrophages (TAMs) and/or their precursor human CD14+CD16+ monocytes in blood serum have recovered (e.g. to about 80% of the original level before anti-CSF-1R treatment). The co-administration is either simultaneously or sequentially (e.g. intravenous (i.v.) through a continuous infusion. In one embodiment the co-administration is simultaneously. In one embodiment the co-administration is sequentially. The co-administration is either simultaneously or sequentially (e.g. intravenous (i.v.) through a continuous infusion.

It is self-evident that the antibodies are administered to the patient in a "therapeutically effective amount" (or simply "effective amount") which is the amount of the respective compound or combination that will elicit the biological or medical response of a tissue, system, animal or human that is being sought by the researcher, veterinarian, medical doctor or other clinician.

The amount of co-administration and the timing of co-administration will depend on the type (species, gender, age, weight, etc.) and condition of the patient being treated and the severity of the disease or condition being treated. Said anti-CSF-1R antibody and further agent are suitably co-administered to the patient at one time or over a series of treatments e.g. on the same day or on the day after.

In addition to the anti-CSF-1R antibody in combination with the macrophage activating agent selected from the group of an agonistic CD40 antibody, a Toll-like receptor (TLR) ligand, a TLR agonist, an antagonistic PD-L1 antibody also a chemotherapeutic agent can be administered.

In one embodiment such additional chemotherapeutic agents, which may be administered with anti-CSF-1R antibody as described herein and the macrophage activating agent selected from the group of an agonistic CD40 antibody, a Toll-like receptor (TLR) ligand, a TLR agonist, an antagonistic PD-L antibody as described herein, include, but are not limited to, anti-neoplastic agents including alkylating agents including: nitrogen mustards, such as mechlorethamine, cyclophosphamide, ifosfamide, melphalan and chlorambucil; nitrosoureas, such as carmustine (BCNU), lomustine (CCNU), and semustine (methyl-CCNU); Temodal™ (temozolomide), ethylenimines/methylmelamine such as triethylenemelamine (TEM), triethylene, thiophosphoramide (thiotepa), hexamethylmelamine (HMM, altretamine); alkyl sulfonates such as busulfan; triazines such as dacarbazine (DTIC); antimetabolites including folic acid analogs such as methotrexate and trimetrexate, pyrimidine analogs such as 5-fluorouracil (5FU), fluorodeoxyuridine, gemcitabine, cytosine arabinoside (AraC, cytarabine), 5-azacytidine, 2,2'-difluorodeoxycytidine, purine analogs such as 6-merca.rho.topurine, 6-thioguamne, azathioprine, T-deoxycoformycin (pentostatin), erythrohydroxynonyladenine (EHNA), fludarabine phosphate, and 2-chlorodeoxyadenosine (cladribine, 2-CdA); natural products including antimitotic drugs such as paclitaxel, vinca alkaloids including vinblastine (VLB), vincristine, and vinorelbine, taxotere, estramustine, and estramustine phosphate; pipodophylotoxins such as etoposide and teniposide; antibiotics such as actinomycin D, daunomycin (rubidomycin), doxorubicin, mitoxantrone, idarubicin, bleomycins, plicamycin (mithramycin), mitonmcin C. and actinomycin; enzymes such as L-asparaginase; biological response modifiers such as interferon-alpha. IL-2, G-CSF and GM-CSF; miscellaneous agents including platinum coordination complexes such as oxaliplatin, cisplatin and carboplatin, anthracenediones such as mitoxantrone, substituted urea such as hydroxyurea, methylhydrazine derivatives including N-methylhydrazine (MIH) and procarbazine, adrenocortical suppressants such as mitotane (o, p-DDD) and aminoglutethimide; hormones and antagonists including adrenocorticosteroid antagonists such as prednisone and equivalents, dexamethasone and aminoglutethimide; Gemzar™ (gemcitabine), progestin such as hydroxyprogesterone caproate, medroxyprogesterone acetate and megestrol acetate; estrogen such as diethylstilbestrol and ethinyl estradiol equivalents; antiestrogen such as tamoxifen; androgens including testosterone propionate and fluoxymesterone/equivalents; antiandrogens such as flutamide, gonadotropin-releasing hormone analogs and leuprolide; and non-steroidal antiandrogens such as flutamide. Therapies targeting epigenetic mechanism including, but not limited to, histone deacetylase inhibitors, demethylating agents (e.g., Vidaza) and release of transcriptional repression (ATRA) therapies can also be combined with the antigen binding proteins. In one embodiment the chemotherapeutic agent is selected from the group consisting of taxanes (like e.g. paclitaxel (Taxol), docetaxel (Taxotere), modified paclitaxel (e.g., Abraxane and Opaxio), doxorubicin, sunitinib (Sutent), sorafenib (Nexavar), and other multikinase inhibitors, oxaliplatin, cisplatin and carboplatin, etoposide, gemcitabine, and vinblastine. In one embodiment the chemotherapeutic agent is selected from the group consisting of taxanes (like e.g. taxol (paclitaxel), docetaxel (Taxotere), modified paclitaxel (e.g. Abraxane and Opaxio). In one embodiment, the additional chemotherapeutic agent is selected from 5-fluorouracil (5-FU), leucovorin, irinotecan, or oxaliplatin. In one embodiment the chemotherapeutic agent is 5-fluorouracil, leucovorin and irinotecan (FOLFIRI). In one embodiment the chemotherapeutic agent is 5-fluorouracil, and oxaliplatin (FOLFOX). In one preferred embodiment, no additional chemotherapeutic agent is administered together with the anti-CSF-1R antibody in combination with the anti-CD40 antibody.

Specific examples of combination therapies with additional chemotherapeutic agents include, for instance, therapies taxanes (e.g., docetaxel or paclitaxel) or a modified paclitaxel (e.g., Abraxane or Opaxio), doxorubicin), capecitabine and/or bevacizumab (Avastin) for the treatment of breast cancer; therapies with carboplatin, oxaliplatin, cisplatin, paclitaxel, doxorubicin (or modified doxorubicin (Caelyx or Doxil)), or topotecan (Hycamtin) for ovarian cancer; therapies with a multi-kinase inhibitor, MKI, (Sutent. Nexavar, or 706) and/or doxorubicin for treatment of kidney cancer; therapies with oxaliplatin, cisplatin and/or radiation for the treatment of squamous cell carcinoma; therapies with taxol and/or carboplatin for the treatment of lung cancer.

Therefore, in one embodiment the additional chemotherapeutic agent is selected from the group of taxanes (docetaxel or paclitaxel or a modified paclitaxel (Abraxane or Opaxio), doxorubicin, capecitabine and/or bevacizumab for the treatment of breast cancer.

In one preferred embodiment, no additional chemotherapeutic agent is administered together with the anti-CSF-1R antibody in combination with the anti-CD40 antibody.

DESCRIPTION OF THE AMINO ACID SEQUENCES

| | |
|---|---|
| SEQ ID NO: 1 | heavy chain variable domain, hMab 2F11-c11 |
| SEQ ID NO: 2 | light chain variable domain, hMab 2F11-c11 |
| SEQ ID NO: 3 | heavy chain variable domain, hMab 2F11-d8 |
| SEQ ID NO: 4 | light chain variable domain, hMab 2F11-d8 |
| SEQ ID NO: 5 | heavy chain variable domain, hMab 2F11-e7 |
| SEQ ID NO: 6 | light chain variable domain, hMab 2F11-e7 |
| SEQ ID NO: 7 | heavy chain variable domain, hMab 2F11-f12 |
| SEQ ID NO: 8 | light chain variable domain, hMab 2F11-f12 |
| SEQ ID NO: 9 | heavy Chain variable domain, hMab 21F11-g1 |
| SEQ ID NO: 10 | light chain variable domain, hMab 2F11-g1 |
| SEQ ID NO: 11 | heavy chain variable domain of CD40 agonist antibody CP-870,893 (antibody 21.4.1 of U.S. Pat. No. 7,338,660) |
| SEQ ID NO: 12 | light chain variable domain of CD40 agonist antibody CP-870,893 (antibody 21.4.1 of U.S. Pat No. 7,338,660) |
| SEQ ID NO: 13 | heavy chain variable domain of CD40 agonist antibody humanized S2C6 variant |
| SEQ ID NO: 14 | light chain variable domain of CD40 agonist antibody humanized S2C6 variant |
| SEQ ID NO: 15 | heavy chain variable domain of anti-PD-L1 antibody atezolizumab |
| SEQ ID NO: 16 | light chain variable domain of anti-PD-L1 antibody atezolizumab |
| SEQ ID NO: 17 | TLR9 agonist CpG ODN 2216 |
| SEQ ID NO: 18 | TLR9 agonist CpG ODN P94 |
| SEQ ID NO: 19 | TLR9 agonist CpG ODN 1002 |
| SEQ ID NO: 20 | TLR9 agonist CpG-7909 (CpG 2006, PF-3512676, Agatolimod) |
| SEQ ID NO: 21 | TLR9 agonist CpG-685 (GNKG168, CpG ODN; SBI Biotech) |
| SEQ ID NO: 22 | TLR9 agonist CpG-684 |
| SEQ ID NO: 23 | TLR9 agonist CpG-28 |
| SEQ ID NO: 24 | exemplary human CSF-1R (wt CSF-1R) |
| SEQ ID NO: 25 | human CSF-1R Extracellular Domain (domains D1-D5) |
| SEQ ID NO: 26 | human CSF-1R fragment domains D1-D3 |
| SEQ ID NO: 27 | human CSF-1R fragment domains D4-D5 |
| SEQ ID NO: 28 | human CSF-1 |
| SEQ ID NO: 29 | human IL-34 |
| SEQ ID NO: 30 | exemplary human CD40 |
| SEQ ID NO: 31 | exemplary human PD-L1 |
| SEQ ID NO: 32 | exemplary human toll-like receptor 9 (TLR9) |
| SEQ ID NO: 33 | human kappa light chain constant region |
| SEQ ID NO: 34 | human heavy chain constant region derived from IgG1 |
| SEQ ID NO: 35 | human heavy chain constant region derived from IgG1 mutated on L234A and L235A |
| SEQ ID NO: 36 | human heavy chain constant region derived from IgG4 |
| SEQ ID NO: 37 | human heavy chain constant region derived from IgG4 mutated on S228P |

In the following, specific embodiments of the invention are described:
1A. An antibody which binds to human CSF-1R, for use in
  a) the treatment of cancer, or
  b) the treatment of a patient having a tumor with CSF-1R expressing macrophage infiltrate.
    wherein the anti-CSF-1R antibody is administered in a first treatment cycle in combination with a macrophage activating agent selected from the group of an agonistic CD40 antibody, a Toll-like receptor (TLR) ligand, a TLR agonist, an antagonistic PD-L antibody, and wherein in the following treatment cycles the anti-CSF-1R antibody is administered only at every second cycle (in one embodiment at every third cycle) in combination with the macrophage activating agent, while the macrophage activating agent is administered at each treatment cycle.

1B. An antibody which binds to human CSF-1R, for use in
   a) the treatment of cancer, or
   b) the treatment of a patient having a tumor with CSF-1R expressing macrophage infiltrate,
   wherein the anti-CSF-1R antibody is administered in a first treatment cycle in combination with a macrophage activating agent selected from the group of an agonistic CD40 antibody, a Toll-like receptor (TLR) ligand, a TLR agonist, an antagonistic PD-L1 antibody,
   and wherein in the following the anti-CSF-1R antibody is administered only in combination with the macrophage activating agent after a significant recovery of CD14+ CD16+ positive monocytes in blood serum (in one embodiment the recovery is more than 60%, in one embodiment more than 80%).

1C. An antibody which binds to human CSF-1R, for use in
   a) the treatment of cancer, or
   b) the treatment of a patient having a tumor with CSF-1R expressing macrophage infiltrate,
   wherein the anti-CSF-1R antibody is administered in a first treatment cycle in combination with a macrophage activating agent selected from the group of an agonistic CD40 antibody, a Toll-like receptor (TLR) ligand, a TLR agonist, an antagonistic PD-L1 antibody,
   and wherein in the following the anti-CSF-1R antibody is administered only in combination with the macrophage activating agent after a significant recovery of CD163+/ CD68+ positive tumor associated macrophages (in one embodiment the recovery is more than 60%, in one embodiment more than 80%).

2. The anti-CSF-1R antibody for use in the treatment of any one of embodiments 1A or 1B or 1C, wherein in the following treatment cycles the anti-CSF-1R antibody is administered only at every second cycle (in one embodiment at every third cycle) in combination with the macrophage activating agent, while the macrophage activating agent is administered at each treatment cycle.

3. The anti-CSF-1R antibody for use in the treatment of any one of embodiments 1 to 2, wherein the length of the treatment cycle is between 2 and 4 weeks (in one preferred embodiment the length of the treatment cycle is between 18 and 24 days and in another preferred embodiment the length of the treatment cycle is (about) 3 weeks).

4. The anti-CSF-1R antibody for use in the treatment of any one of embodiments 1 to 3, wherein the anti-CSF-1R antibody is administered at a dose of 600-1200 mg (in one embodiment at a dose of 750-1100 mg, in one embodiment at a dose of 750-1000, 900-1000 mg, in embodiment 750, in one embodiment 900, in one embodiment 1000).

5. The anti-CSF-1R antibody for use in the treatment of any one of embodiments 1 to 4, wherein the macrophage activating agent is an agonistic CD40 antibody and is administered at a dose of 4-16 mg (in one embodiment at a dose of 8-16 mg) at each cycle.

6. The anti-CSF-1R antibody for use in the treatment of any one of embodiments 1 to 4, wherein the macrophage activating agent is an antagonistic PD-L1 antibody and is administered at a dose of 1100-1300 mg (in one embodiment at a dose of 1200) at each cycle.

7. The anti-CSF-1R antibody for use in the treatment of any one of embodiments 1 to 6, wherein the combined therapy is for use in treating or delaying progression of an immune related disease such as tumor immunity.

8. The anti-CSF-1R antibody for use in the treatment of any one of embodiments 1 to 6, wherein the combined therapy is for use in stimulating an immune response or function, such as T cell activity.

9. The anti-CSF-1R antibody for use in the treatment of any one of embodiments 1 to 8, wherein the anti-CSF-1R antibody comprises
   a) a heavy chain variable domain VH of SEQ ID NO:1 and a light chain variable domain VL of SEQ ID NO:2, or
   b) a heavy chain variable domain VH of SEQ ID NO:3 and a light chain variable domain VL of SEQ ID NO:4, or
   c) a heavy chain variable domain VH of SEQ ID NO:5 and a light chain variable domain VL of SEQ ID NO:6, or
   d) a heavy chain variable domain VH of SEQ ID NO:7 and a light chain variable domain VL of SEQ ID NO:8, or
   e) a heavy chain variable domain VH of SEQ ID NO:9 and a light chain variable domain VL of SEQ ID NO: 10; and 10. The anti-CSF-1R antibody for use in the treatment of any one of embodiments 1 to 5, 7 to 9, therein the macrophage activating agent is an agonistic CD40 antibody 11. The anti-CSF-1R antibody for use in the treatment of embodiment 11.
   wherein anti-CSF-1R antibody comprises
   a heavy chain variable domain VH of SEQ ID NO:5 and a light chain variable domain VL of SEQ ID NO:6, and
   the agonistic CD40 antibody comprises
   a heavy chain variable domain VH of SEQ ID NO:11 and a light chain variable domain VL of SEQ ID NO: 12.

12. The anti-CSF-1R antibody for use in the treatment of any one of embodiments 1 to 4, 6 to 9, wherein the macrophage activating agent is an antagonistic PD-L1 antibody 13. The anti-CSF-1R antibody for use in the treatment of embodiment 12,
   wherein anti-CSF-1R antibody comprises
   a heavy chain variable domain VH of SEQ ID NO:5 and a light chain variable domain VL of SEQ ID NO:6, and
   the antagonistic PD-L antibody comprises
   a heavy chain variable domain VH of SEQ ID NO:15 and a light chain variable domain VL of SEQ ID NO: 16.

14. The anti-CSF-1R antibody for use in the treatment of any one of embodiments 1 to 4, 7 to 9, wherein the macrophage activating agent is a TLR9 agonist.

15. The anti-CSF-1R antibody for use in the treatment of embodiment 14,
   wherein anti-CSF-1R antibody comprises
   a heavy chain variable domain VH of SEQ ID NO:5 and a light chain variable domain VL of SEQ ID NO:6, and
   wherein the TLR9 agonist is a oligodeoxynucleotides containing a) cytosine-phosphate-guanosine (CpG) motifs (CpG ODNs) b) pyrimidine-phosphate-guanosine (YpG) motifs (YpG ODNs) or c) cytosine-phosphate-purine (CpR) motifs (CpR ODNs) (preferably a oligodeoxynucleotides containing cytosine-phosphate-guanosine (CpG) motifs (CpG ODNs)).

In the following, specific embodiments of the invention are described:

1A. A pharmaceutical composition or medicament comprising an antibody which binds to human CSF-1R, for use in
   a) the treatment of cancer, or
   b) the treatment of a patient having a tumor with CSF-1R expressing macrophage infiltrate,
   wherein the anti-CSF-1R antibody is administered in a first treatment cycle in combination with a macrophage activating agent selected from the group of an agonistic CD40 antibody, a Toll-like receptor (TLR) ligand, a TLR agonist, an antagonistic PD-L1 antibody,
   and wherein in the following treatment cycles the anti-CSF-1R antibody is administered only at every second cycle (in one embodiment at every third cycle) in combination with the macrophage activating agent, while the macrophage activating agent is administered at each treatment cycle.
1B. A pharmaceutical composition or medicament comprising an antibody which binds to human CSF-1R, for use in
   a) the treatment of cancer, or
   b) the treatment of a patient having a tumor with CSF-1R expressing macrophage infiltrate,
   wherein the anti-CSF-1R antibody is administered in a first treatment cycle in combination with a macrophage activating agent selected from the group of an agonistic CD40 antibody, a Toll-like receptor (TLR) ligand, a TLR agonist, an antagonistic PD-L antibody,
   and wherein in the following the anti-CSF-1R antibody is administered only in combination with the macrophage activating agent after a significant recovery of CD14+ CD16+ positive monocytes in blood serum (in one embodiment the recovery is more than 60%, in one embodiment more than 80%).
1C. A pharmaceutical composition or medicament comprising an antibody which binds to human CSF-1R, for use in
   a) the treatment of cancer, or
   b) the treatment of a patient having a tumor with CSF-1R expressing macrophage infiltrate,
   wherein the anti-CSF-1R antibody is administered in a first treatment cycle in combination with a macrophage activating agent selected from the group of an agonistic CD40 antibody, a Toll-like receptor (TLR) ligand, a TLR agonist, an antagonistic PD-L1 antibody,
   and wherein in the following the anti-CSF-1R antibody is administered only in combination with the macrophage activating agent after a significant recovery of CD163+/CD68+ positive tumor associated macrophages (in one embodiment the recovery is more than 60%, in one embodiment more than 80%).
2. The pharmaceutical composition or medicament of any one of embodiments 1A or 1B or 1C, wherein in the following treatment cycles the anti-CSF-1R antibody is administered only at every second cycle (in one embodiment at every third cycle) in combination with the macrophage activating agent, while the macrophage activating agent is administered at each treatment cycle.
3. The pharmaceutical composition or medicament of any one of embodiments 1 to 2, wherein the length of the treatment cycle is between 2 and 4 weeks (in one preferred embodiment the length of the treatment cycle is between 18 and 24 days and in another preferred embodiment the length of the treatment cycle is (about) 3 weeks).
4. The pharmaceutical composition or medicament of any one of embodiments 1 to 3, wherein the anti-CSF-1R antibody is administered at a dose of 600-1200 mg (in one embodiment at a dose of 750-1100 mg, in one embodiment at a dose of 750-1000, 900-1000 mg, in embodiment 750, in one embodiment 900, in one embodiment 1000).
5. The pharmaceutical composition or medicament of any one of embodiments 1 to 4, wherein the macrophage activating agent is an agonistic CD40 antibody and is administered at a dose of 4-16 mg (in one embodiment at a dose of 8-16 mg) at each cycle.
6. The pharmaceutical composition or medicament of any one of embodiments 1 to 4, wherein the macrophage activating agent is an antagonistic PD-L1 antibody and is administered at a dose of 1100-1300 mg (in one embodiment at a dose of 1200) at each cycle.
7. The pharmaceutical composition or medicament of any one of embodiments 1 to 6, wherein the combined therapy is for use in treating or delaying progression of an immune related disease such as tumor immunity.
8. The pharmaceutical composition or medicament of any one of embodiments 1 to 6, wherein the combined therapy is for use in stimulating an immune response or function, such as T cell activity.
9. The pharmaceutical composition or medicament of any one of embodiments 1 to 8, wherein the anti-CSF-1R antibody comprises
   a) a heavy chain variable domain VH of SEQ ID NO:1 and a light chain variable domain VL of SEQ ID NO:2, or
   b) a heavy chain variable domain VH of SEQ ID NO:3 and a light chain variable domain VL of SEQ ID NO:4, or
   c) a heavy chain variable domain VH of SEQ ID NO:5 and a light chain variable domain VL of SEQ ID NO:6, or
   d) a heavy chain variable domain VH of SEQ ID NO:7 and a light chain variable domain VL of SEQ ID NO:8, or
   e) a heavy chain variable domain VH of SEQ ID NO:9 and a light chain variable domain VL of SEQ ID NO: 10 and
10. The pharmaceutical composition or medicament of any one of embodiments 1 to 5, 7 to 9, wherein the macrophage activating agent is an agonistic CD40 antibody
11. The pharmaceutical composition or medicament of embodiment 10,
   wherein anti-CSF-1R antibody comprises
   a heavy chain variable domain VH of SEQ ID NO:5 and a light chain variable domain VL of SEQ ID NO:6, and
   the agonistic CD40 antibody comprises
   a heavy chain variable domain VH of SEQ ID NO: 11 and a light chain variable domain VL of SEQ ID NO: 12.
12. The pharmaceutical composition or medicament of any one of embodiments 1 to 4, 6 to 9, wherein the macrophage activating agent is an antagonistic PD-L1 antibody
13. The pharmaceutical composition or medicament of embodiment 13,
   wherein anti-CSF-1R antibody comprises
   a heavy chain variable domain VH of SEQ ID NO:5 and a light chain variable domain VL of SEQ ID NO:6, and
   the antagonistic PD-L1 antibody comprises
   a heavy chain variable domain VH of SEQ ID NO:15 and a light chain variable domain VL of SEQ ID NO: 16.
14. The pharmaceutical composition or medicament of any one of embodiments 1 to 4, 7 to 9, wherein the macrophage activating agent is a TLR9 agonist.
15. The pharmaceutical composition or medicament of embodiment 14.
   wherein anti-CSF-1R antibody comprises
   a heavy chain variable domain VH of SEQ ID NO:5 and a light chain variable domain VL of SEQ ID NO:6, and wherein the TLR9 agonist is a oligodeoxynucleotides containing a) cytosine-phosphate-guanosine (CpG) motifs (CpG ODNs) b) pyrimidine-phosphate-guanosine (YpG) motifs (YpG ODNs) or c) cytosine-phosphate-purine (CpR) motifs (CpR ODNs) (preferably a oligodeoxynucleotides containing cytosine-phosphate-guanosine (CpG) motifs (CpG ODNs)).

In the following, specific embodiments of the invention are described:

1A. Use of an antibody which binds to human CSF-1R, in the manufacture of a medicament for
  a) the treatment of cancer, or
  b) the treatment of a patient having a tumor with CSF-1R expressing macrophage infiltrate,
  wherein the anti-CSF-1R antibody is administered in a first treatment cycle in combination with a macrophage activating agent selected from the group of an agonistic CD40 antibody, a Toll-like receptor (TLR) ligand, a TLR agonist, an antagonistic PD-L1 antibody,
  and wherein in the following treatment cycles the anti-CSF-1R antibody is administered only at every second cycle (in one embodiment at every third cycle) in combination with the macrophage activating agent, while the macrophage activating agent is administered at each treatment cycle.

1B. Use of an antibody which binds to human CSF-1R, in the manufacture of a medicament for
  a) the treatment of cancer, or
  b) the treatment of a patient having a tumor with CSF-1R expressing macrophage infiltrate,
  wherein the anti-CSF-1R antibody is administered in a first treatment cycle in combination with a macrophage activating agent selected from the group of an agonistic CD40 antibody, a Toll-like receptor (TLR) ligand, a TLR agonist, an antagonistic PD-L1 antibody,
  and wherein in the following the anti-CSF-1R antibody is administered only in combination with the macrophage activating agent after a significant recovery of CD14+ CD16+ positive monocytes in blood serum (in one embodiment the recovery is more than 60%, in one embodiment more than 80%).

1C. Use of an antibody which binds to human CSF-1R, in the manufacture of a medicament for
  a) the treatment of cancer, or
  b) the treatment of a patient having a tumor with CSF-1R expressing macrophage infiltrate,
  wherein the anti-CSF-1R antibody is administered in a first treatment cycle in combination with a macrophage activating agent selected from the group of an agonistic CD40 antibody, a Toll-like receptor (TLR) ligand, a TLR agonist, an antagonistic PD-L1 antibody,
  and wherein in the following the anti-CSF-1R antibody is administered only in combination with the macrophage activating agent after a significant recovery of CD163+/CD68+ positive tumor associated macrophages (in one embodiment the recovery is more than 60%, in one embodiment more than 80%).

2. The use of any one of embodiments 1A or 1B or 1C, wherein in the following treatment cycles the anti-CSF-1R antibody is administered only at every second cycle (in one embodiment at every third cycle) in combination with the macrophage activating agent, while the macrophage activating agent is administered at each treatment cycle.

3. The use of any one of embodiments 1 to 2, wherein the length of the treatment cycle is between 2 and 4 weeks (in one preferred embodiment the length of the treatment cycle is between 18 and 24 days and in another preferred embodiment the length of the treatment cycle is (about) 3 weeks).

4. The use of any one of embodiments 1 to 3, wherein the anti-CSF-1R antibody is administered at a dose of 600-1200 mg (in one embodiment at a dose of 750-1100 mg, in one embodiment at a dose of 750-1000, 900-1000 mg, in embodiment 750, in one embodiment 900, in one embodiment 1000).

5. The use of any one of embodiments 1 to 4, wherein the macrophage activating agent is an agonistic CD40 antibody and is administered at a dose of 4-16 mg (in one embodiment at a dose of 8-16 mg) at each cycle.

6. The use of any one of embodiments 1 to 4, wherein the macrophage activating agent is an antagonistic PD-L1 antibody and is administered at a dose of 1100-1300 mg (in one embodiment at a dose of 1200) at each cycle.

7. The use of any one of embodiments 1 to 6, wherein the combined therapy is for use in treating or delaying progression of an immune related disease such as tumor immunity.

8. The use of any one of embodiments 1 to 6, wherein the combined therapy is for use in stimulating an immune response or function, such as T cell activity.

9. The use of any one of embodiments 1 to 8, wherein the anti-CSF-1R antibody comprises
  a) a heavy chain variable domain VH of SEQ ID NO:1 and a light chain variable domain VL of SEQ ID NO:2, or
  b) a heavy chain variable domain VH of SEQ ID NO:3 and a light chain variable domain VL of SEQ ID NO:4, or
  c) a heavy chain variable domain VH of SEQ ID NO:5 and a light chain variable domain VL of SEQ ID NO:6, or
  d) a heavy chain variable domain VH of SEQ ID NO:7 and a light chain variable domain VL of SEQ ID NO:8, or
  e) a heavy chain variable domain VH of SEQ ID NO:9 and a light chain variable domain VL of SEQ ID NO: 10 and 10. The use of any one of embodiments 1 to 5, 7 to 9, wherein the macrophage activating agent is an agonistic CD40 antibody 11. The use of embodiment 10,
  wherein anti-CSF-1R antibody comprises
  a heavy chain variable domain VH of SEQ ID NO:5 and a light chain variable domain VL of SEQ ID NO:6, and
  the agonistic CD40 antibody comprises
  a heavy chain variable domain VH of SEQ ID NO:11 and a light chain variable domain VL of SEQ ID NO: 12.

12. The use of any one of embodiments 1 to 4, 6 to 9, wherein the macrophage activating agent is an antagonistic PD-L1 antibody 13. The use of embodiment 12,
  wherein anti-CSF-1R antibody comprises
  a heavy chain variable domain VH of SEQ ID NO:5 and a light chain variable domain VL of SEQ ID NO:6, and
  the antagonistic PD-L1 antibody comprises
  a heavy chain variable domain VH of SEQ ID NO:15 and a light chain variable domain VL of SEQ ID NO: 16.

14. The use of any one of embodiments 1 to 4, 7 to 9, wherein the macrophage activating agent is a TLR9 agonist.

15. The use of embodiment 14,
wherein anti-CSF-1R antibody comprises
a heavy chain variable domain VH of SEQ ID NO:5 and a light chain variable domain VL of SEQ ID NO:6, and
wherein the TLR9 agonist is a oligodeoxynucleotides containing a) cytosine-phosphate-guanosine (CpG) motifs (CpG ODNs) b) pyrimidine-phosphate-guanosine (YpG) motifs (YpG ODNs) or c) cytosine-phosphate-purine (CpR) motifs (CpR ODNs) (preferably a oligodeoxynucleotides containing cytosine-phosphate-guanosine (CpG) motifs (CpG ODNs)).

In the following, specific embodiments of the invention are described:

1A. A method of treatment, the method comprising administering (an effective amount of) an antibody which binds to human CSF-1R, for use in
a) the treatment of cancer, or
b) the treatment of a patient having a tumor with CSF-1R expressing macrophage infiltrate,
wherein the anti-CSF-1R antibody is administered in a first treatment cycle in combination with (an effective amount of) a macrophage activating agent selected from the group of an agonistic CD40 antibody, a Toll-like receptor (TLR) ligand, a TLR agonist, an antagonistic PD-L1 antibody,
and wherein in the following treatment cycles the anti-CSF-1R antibody is administered only at every second cycle (in one embodiment at every third cycle) in combination with the macrophage activating agent, while the macrophage activating agent is administered at each treatment cycle.

1B. A method of treatment, the method comprising administering (an effective amount of) an antibody which binds to human CSF-1R, for use in
a) the treatment of cancer, or
b) the treatment of a patient having a tumor with CSF-1R expressing macrophage infiltrate,
wherein the anti-CSF-1R antibody is administered in a first treatment cycle in combination with (an effective amount of) a macrophage activating agent selected from the group of an agonistic CD40 antibody, a Toll-like receptor (TLR) ligand, a TLR agonist, an antagonistic PD-L1 antibody.
and wherein in the following the anti-CSF-1R antibody is administered only in combination with the macrophage activating agent after a significant recovery of CD14+ CD16+ positive monocytes in blood serum (in one embodiment the recovery is more than 60%, in one embodiment more than 80%).

1C. A method of treatment, the method comprising administering (an effective amount of) an antibody which binds to human CSF-1R, for use in
a) the treatment of cancer, or
b) the treatment of a patient having a tumor with CSF-1R expressing macrophage infiltrate,
wherein the anti-CSF-1R antibody is administered in a first treatment cycle in combination with (an effective amount of) a macrophage activating agent selected from the group of an agonistic CD40 antibody, a Toll-like receptor (TLR) ligand, a TLR agonist, an antagonistic PD-L1 antibody,
and wherein in the following the anti-CSF-1R antibody is administered only in combination with the macrophage activating agent after a significant recovery of CD163+/CD68+ positive tumor associated macrophages (in one embodiment the recovery is more than 60%, in one embodiment more than 80%).

2. The method of any one of embodiments 1A or 1B or 1C. wherein in the following treatment cycles the anti-CSF-1R antibody is administered only at every second cycle (in one embodiment at every third cycle) in combination with the macrophage activating agent, while the macrophage activating agent is administered at each treatment cycle.

3. The method of any one of embodiments 1 to 2, wherein the length of the treatment cycle is between 2 and 4 weeks (in one preferred embodiment the length of the treatment cycle is between 18 and 24 days and in another preferred embodiment the length of the treatment cycle is (about) 3 weeks).

4. The method of any one of embodiments 1 to 3, wherein the anti-CSF-1R antibody is administered at a dose of 600-1200 mg (in one embodiment at a dose of 750-1100 mg, in one embodiment at a dose of 750-1000, 900-1000 mg, in embodiment 750, in one embodiment 900, in one embodiment 1000).

5. The method of any one of embodiments 1 to 4, wherein the macrophage activating agent is an agonistic CD40 antibody and is administered at a dose of 4-16 mg (in one embodiment at a dose of 8-16 mg) at each cycle.

6. The method of any one of embodiments 1 to 4, wherein the macrophage activating agent is an antagonistic PD-L1 antibody and is administered at a dose of 1100-1300 mg (in one embodiment at a dose of 1200) at each cycle.

7. The method of any one of embodiments 1 to 6, wherein the combined therapy is for use in treating or delaying progression of an immune related disease such as tumor immunity.

8. The method of any one of embodiments 1 to 6, wherein the combined therapy is for use in stimulating an immune response or function, such as T cell activity.

9. The method of any one of embodiments 1 to 8, wherein the anti-CSF-1R antibody comprises
a) a heavy chain variable domain VH of SEQ ID NO:1 and a light chain variable domain VL of SEQ ID NO:2, or
b) a heavy chain variable domain VH of SEQ ID NO:3 and a light chain variable domain VL of SEQ ID NO:4, or
c) a heavy chain variable domain VH of SEQ ID NO:5 and a light chain variable domain VL of SEQ ID NO:6, or
d) a heavy chain variable domain VH of SEQ ID NO:7 and a light chain variable domain VL of SEQ ID NO:8, or
e) a heavy chain variable domain VH of SEQ ID NO:9 and a light chain variable domain VL of SEQ ID NO: 10; and 10. The method of any one of embodiments 1 to 5, 7 to 9, wherein the macrophage activating agent is an agonistic CD40 antibody 11. The method of embodiment 10,
wherein anti-CSF-1R antibody comprises
a heavy chain variable domain VH of SEQ ID NO:5 and a light chain variable domain VL of SEQ ID NO:6, and
the agonistic CD40 antibody comprises
a heavy chain variable domain VH of SEQ ID NO:11 and a light chain variable domain VL of SEQ ID NO: 12.

12. The method of any one of embodiments 1 to 4, 6 to 9, wherein the macrophage activating agent is an antagonistic PD-L1 antibody 13. The method of embodiment 12,
wherein anti-CSF-1R antibody comprises
a heavy chain variable domain VH of SEQ ID NO:5 and
a light chain variable domain VL of SEQ ID NO:6, and
the antagonistic PD-L1 antibody comprises
a heavy chain variable domain VH of SEQ ID NO:15 and
a light chain variable domain VL of SEQ ID NO: 16.
14. The method of any one of embodiments 1 to 4, 7 to 9,
wherein the macrophage activating agent is a TLR9
agonist.
15. The method of embodiment 14,
wherein anti-CSF-1R antibody comprises
a heavy chain variable domain VH of SEQ ID NO:5 and
a light chain variable domain VL of SEQ ID NO:6, and
wherein the TLR9 agonist is a oligodeoxynucleotides
containing a) cytosine-phosphate-guanosine (CpG)
motifs (CpG ODNs) b) pyrimidine-phosphate-guanosine (YpG) motifs (YpG ODNs) or c) cytosine-phosphate-purine (CpR) motifs (CpR ODNs) (preferably a
oligodeoxynucleotides containing cytosine-phosphate-guanosine (CpG) motifs (CpG ODNs)).

EXAMPLES

Combination of Anti-CSF-1R Antibody and Macrophage
Activating Agonistic CD40 Antibody Example 1A: Synergistic Efficacy of Anti-CSF-R
Antibody+ Macrophage Activating Agonistic CD40
Antibody (FIGS. 1A, 1B, and 1C)

Female C57BL/6N mice (6-8 weeks in age, obtained from
Charles River) were inoculated with $10^6$ MC38 colorectal
adenocarcinoma tumor cells subcutaneously. Tumor growth
curves were monitored by caliper measurement and once
tumor size reached 250 mm³ in average, groups were allocated for treatment with the following:
a) IgG isotype control antibody: 30 mg/kg murine IgG1,
clone MOPC-21 (BioXCell); or
b) anti-CD40 antibody: 4 mg/kg rat IgG2a antibody, clone
FGK45 (BioXCell); or
c) anti-CSF-1R antibody: 30 mg/kg hamster-mouse chimeric antibody clone 2G2 (Ries et al., Cancer Cell 25:846-859,
2014), or
d) combination of anti-CD40 antibody and anti-CSF-1R
antibody: combined, simultaneous treatment, dosing as in b)
and c).

The anti-CSF-1R antibody or respective IgG1 control
antibody were administered weekly until tumors regressed
completely or animals reached termination criteria, while
the anti-CD40 antibody was only administered once at day
10 concomitantly with the anti-CSF-1R antibody. The overall study design is depicted in FIG. 1A.

Figure 1B:
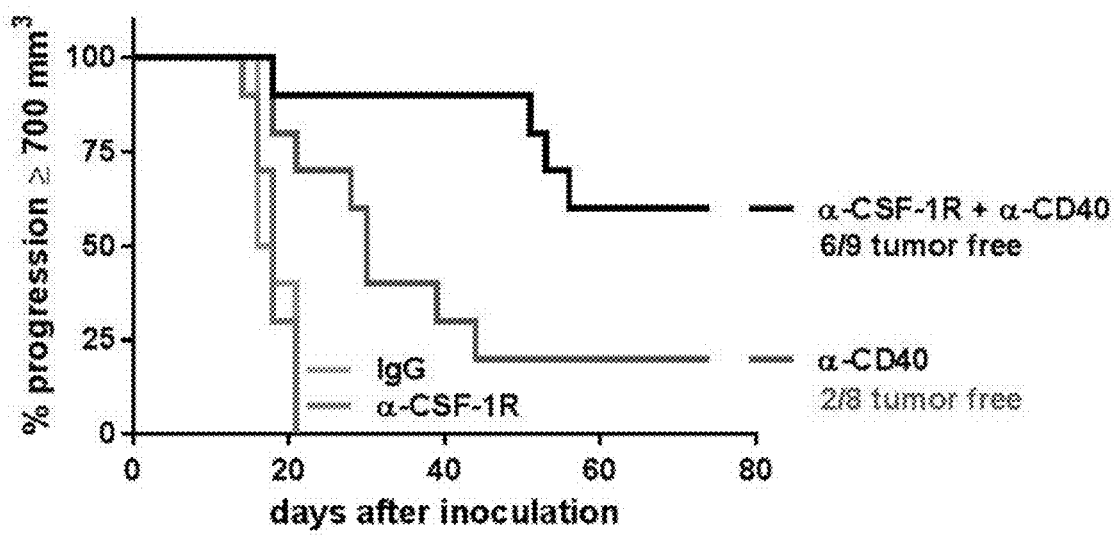
Figure 1C:
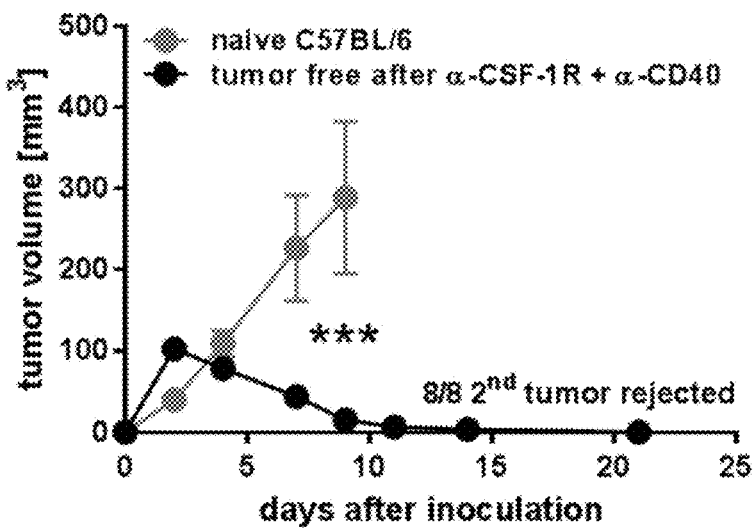

FIG. 1B depicts progression free survival until tumor
volume reached ≥700 mm³ demonstrating synergistic anti-tumoral efficacy of the CSF-1R and CD40 antibody combination treatment. Mice that were treated with the combination of the anti-CSF-1R antibody and the anti-CD40
antibody and that remained tumor-free for at least 30 days
upon rejection of the primary tumor, were re-challenged by
subcutaneous inoculation 5×10⁶ MC38 into the contralateral
flank. FIG. 1C shows that the re-challenge of mice previously treated with the anti-CSF-1R antibody combined with
anti-CD40 antibody resulted in rapid tumor rejection, as
compared to naïve mice. Indeed, all 8 previously combination-treated mice were tumor free by day 21 after second
tumor injection. These results indicate that the anti-CSF-1R
and anti-CD40 antibody combination treatment can induce a
tumor-cell specific immune response.

Figure 2A:
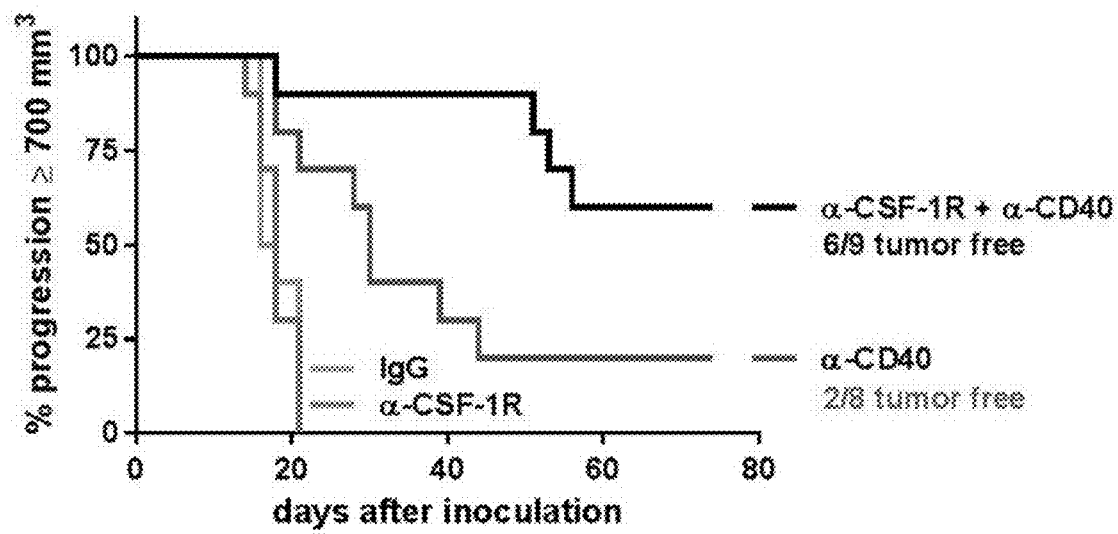
FIG. 2A and FIG. 2B.
Figure 2B:
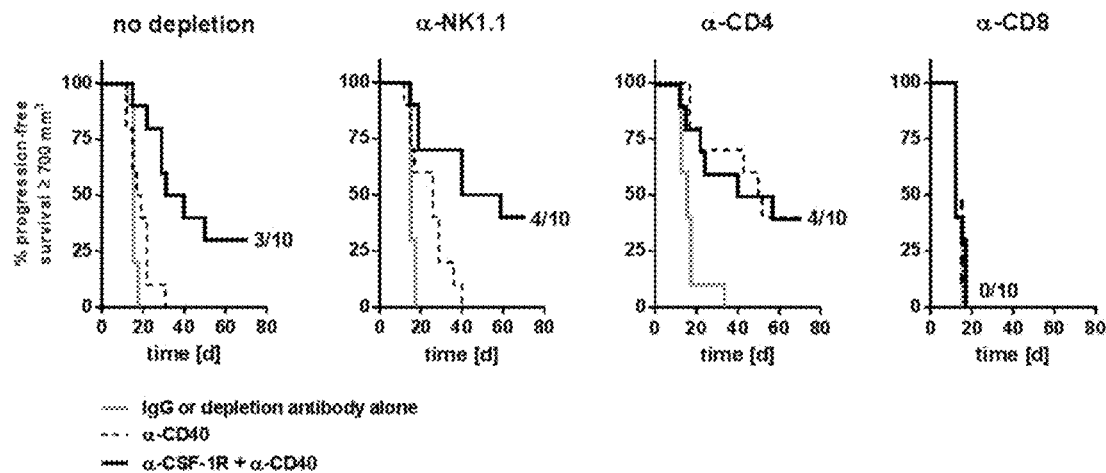

Example 1B: Depletion of CD8α Positive T Cells
Prior to Combined Treatment of Anti-CD40 and
Anti-CSF1R Antibodies Abolishes of the
Synergistic Effect of Anti-CSF-R Antibody and a
Macrophage Activating Agent Like Agonistic CD40
Antibody (FIGS. 2A and 2B)

Female C57BL/6N mice (6-8 weeks in age, obtained from
Charles River) were inoculated with $10^6$ MC38 colorectal
adenocarcinoma tumor cells subcutaneously. Tumor growth
curves were monitored by caliper measurement and once
tumor size reached 190 mm³ in average, mice were allocated
for treatment with the following depleting antibodies:
a) anti-CD8a antibody; 4 mg/kg mouse IgG2a, clone 53-6.7
(BioXCell); or
b) anti-CD4 antibody; 4 mg/kg mouse IgG2b, clone GK1.5
(Biolegend); or
c) anti-NK1.1 antibody: 4 mg/kg mouse IgG2a, clone
PK136 (BioXCell);

Depletion of lymphocytes using anti-CD8α, anti-CD4
and anti-NK1.1 antibodies was started when tumor size
reached 190 mm³ in average. Antibodies were given every
second day for four times. In between doses two and three
of the depleting antibodies, animals were further treated with
the following:
d) Vehicle control: 0.9% sodium saline (depletion antibody
alone control), or
e) IgG isotype control antibody: 30 mg/kg murine IgG1,
clone MOPC-21 (BioXCell); or
f) anti-CD40 antibody: 4 mg/kg rat IgG2a antibody, clone
FGK45 (BioXCell); or
g) combination of anti-CD40 antibody and anti-CSF-1R
antibody: 30 mg/kg hamster-mouse chimeric antibody clone
2G2 (Ries et al., Cancer Cell 25:846-859, 2014);

The anti-CSF-1R antibody or respective IgG1 control
antibody were administered weekly until tumors regressed
completely or animals reached termination criteria, while
the anti-CD40 antibody was only administered once at day
11 simultaneously with the anti-CSF-1R antibody. The overall study design is depicted in FIG. 2A.

FIG. 2B shows, that the depletion of CD8 positive T cells
results in the abolishment of the beneficial effect on survival
in anti-CD40 and CSF-1R tumor bearing mice. Depletion of
neither CD4 positive T cells nor NK1.1 expressing NK cells
effected the survival in these mice. This underlines that a
cytotoxic T cell response is initiated in mice treated with the
combination. Of note, the survival of mice depleted of CD4
positive cells and treated with anti-CD40 alone was significantly enhanced (4 out of 10 mice tumor free) compared to
the mice being depleted of other lymphocyte subtypes. This
might indicate that suppressive CD4 positive T cells (e.g.
regulatory T cells) also have a negative impact on overall
survival in MC38 tumor bearing mice upon anti-CD40
treatment.

Figure 3A:
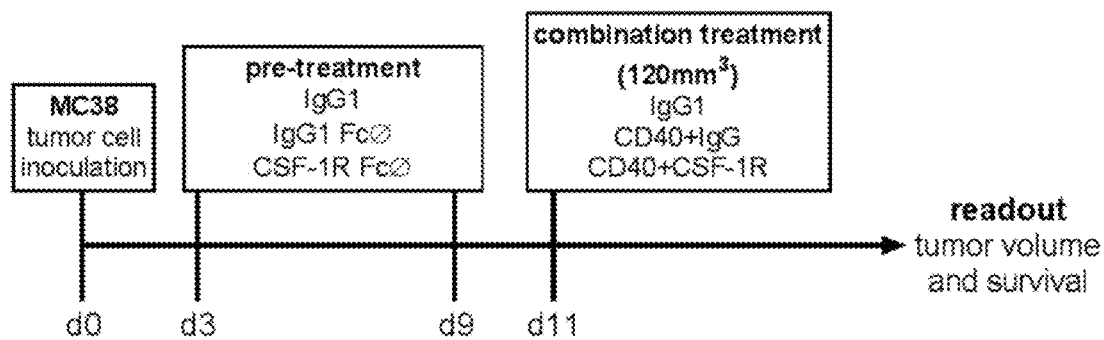
FIGS. 3A-FIG. 3C.
Figure 3B:
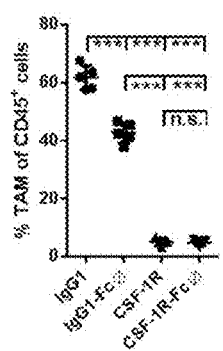
Figure 3C:
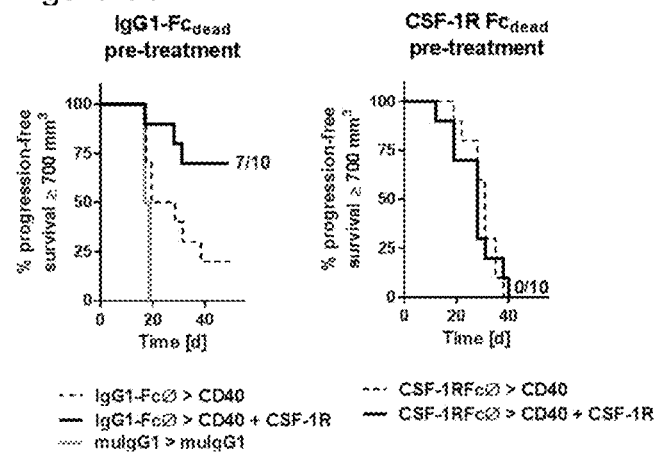

Example 1C: Synergistic Efficacy of Anti-CSF-R
Antibody and a Macrophage Activating Agent Like
Agonistic CD40 Antibody Depends on the Presence
of Tumor Associated Macrophages (TAMs) (FIGS.
3A, 3B, and 3C)

Female C57BL/6N mice (6-8 weeks in age, obtained from
Charles River) were inoculated using $10^6$ MC38 colorectal
adenocarcinoma tumor cells subcutaneously. Tumor growth curves were monitored by caliper measurement and pre-treatment was started on day 3. Animals were allocated for pre-treatment with the following antibodies:

a) IgG isotype control antibody: 30 mg/kg murine IgG1, clone MOPC-21 (BioXCell, fully Fc-competent antibody); or b) Fc dead (FcØ) variant of IgG isotype control antibody: 30 mg/kg human IgG1, anti-Digoxigenin (US 2012/0251531 A1); or c) anti-CSF-1R antibody Fc-dead (FcØ) variant: 30 mg/kg hamster-human chimeric antibody. CDR of clone 2G2 (Ries et al., Cancer Cell 25:846-859, 2014) on a human IgG1 PG LALA FcØ(Roche patent US 2012/0251531 A1)

For efficacy readout, mice were injected intra-peritoneal on day 3 and day 9 after tumor inoculation with either of the antibodies (a to c) and then further allocated by tumor size (120 mm$^3$ in average) to be treated with the following antibodies on day 11:

d) IgG isotype control antibody: 30 mg/kg murine IgG1, clone MOPC-21 (BioXCell); or e) anti-CD40 antibody: 4 mg/kg rat IgG2a antibody, clone FGK45 (BioXCell); or f) combination of anti-CD40 antibody and anti-CSF-1R antibody (30 mg/kg hamster-mouse chimeric antibody clone 2G2; Ries et al., Cancer Cell 25:846-859, 2014).

For the combination treatment, animals were only treated once with anti-CD40 antibody and anti-CSF-1R antibodies simultaneously. The overall design of the study is depicted in FIG. 3A.

Flow cytometry: On tumors of 4 mice per pre-treatment group, flow cytometry was used to determine the efficacy for TAM depletion on day 11 before administration of the combinational treatment. Treatment with the full Fc-competent CSF-1R antibody (clone 2G2, treatment on day 3 and 9, 30 mg/kg; Ries et al. Cancer Cell 2014, 25:846-859) served as a positive control. For flow cytometric analysis, tumors were collected and digested upon mechanical disruption using Dispase II (final 1 mg/ml, Roche #04942078001), Collagenase IV (final 1 mg/ml, Sigma Aldrich # L5138) and DNAse I (final 0.01%; Roche #11284932001) for 30 min at 37° C. in DPBS (PAN-Biotech, # P04-36500). After running single cell suspension over a 40 µm cell strainer (EASYstrainer, Greiner #542 040) and washing cells, erythrocytes were removed using Pharm Lyse Buffer according to the manufacturer's instructions (BD Pharmingen, #558995). Cells (2×10$^6$) were finally re-suspended in 125 µl FACS buffer (DPBS+5% FSC (Gibco, #10500-038), 5 mM EDTA (Invitrogen, #15575-038)) and incubated for 5 minutes using Fc-blocking antibody (clone 2.4G2, BD Pharmingen, #553142) before the following antibodies were added, incubated for 30 minutes on ice and washed off again:

| Antigen | Fluorochrome | Company | Order number |
|---|---|---|---|
| CD45 | FITC | BioLegend | 103108 |
| Ly6G | PerCp-Cy5.5 | BioLegend | 127616 |
| F4/80 | PE-Cy7 | BioLegend | 123114 |
| CD11b | BV570 | BioLegend | 101233 |
| Ly6C | APC-Cy7 | BioLegend | 128026 |
| DAPI | viability | Roche | 10236276001 |

To exclude dead cells, DAPI (Roche, #10236276001) was added before data acquisition on a Canto II flow cytometer (BD Bioscience). Data were analyzed using FlowJo Software version 10 and statistically evaluated using GraphPad Prism Software version 6.07.

To show that the combinational effect of anti-CSF-1R and anti-CD40 antibodies (see Example 1A) is indeed dependent on macrophages, TAMs were depleted before applying the combinational therapy. The function of anti-CD40 antibody is dependent on cross-linking via FcRIIb (Li & Ravetch, Science 2011, 333:1030-1034; White et al. Journal of Immunology 2001, 187:1754-63; Richmann & Vonderheide, Cancer Immunology Research 2013, 2: 19-26), which might be blocked when using 30 mg/kg of murine IgG1 (isotype or anti-CSF-1R antibodies) during pretreatment. Therefore isotype controls and the anti-CSF-1R antibodies were used for pretreatment that lack Fc-receptor function (FcØ variants). To confirm the depletion of TAM using this FcØ antibody variant, flow cytometric analysis of was performed on day 11 on tumors of additional animals. TAMs were identified by the following marker combination: DAPI$^-$ CD45$^+$CD11b$^+$ F4/80$^{high}$Ly6G$^{negative}$Ly6C$^{low}$. As shown in FIG. 3B, the anti-CSF-1R FcØ variant is as effective in depleting TAM after 2 treatments with the respective Fc-competent and Fc-silent antibody variants.

The outcome of the survival study with pre-depletion of TAMs before treatment with either anti-CD40 or a combination of anti-CD40 together with anti-CSF-1R antibodies is shown in FIG. 3C. Depletion of TAMs using the CSF-1R FcØ antibody prior to combined anti-CD40 and anti-CSF-1R treatment completely abolished the survival benefit of the combination therapy compared to control pre-treatments (none out of 10 mice were tumor free at the end of the study). Pre-treatment of tumor-bearing mice with isotype controls did result in 7 out of 10 mice completely rejecting the tumor when treated with the CD40/CSF-1R combination. These results underline the important role of macrophages in facilitating the efficacy of combined anti-CD40 and anti-CSF-1R antibody treatment.

Figure 4A:
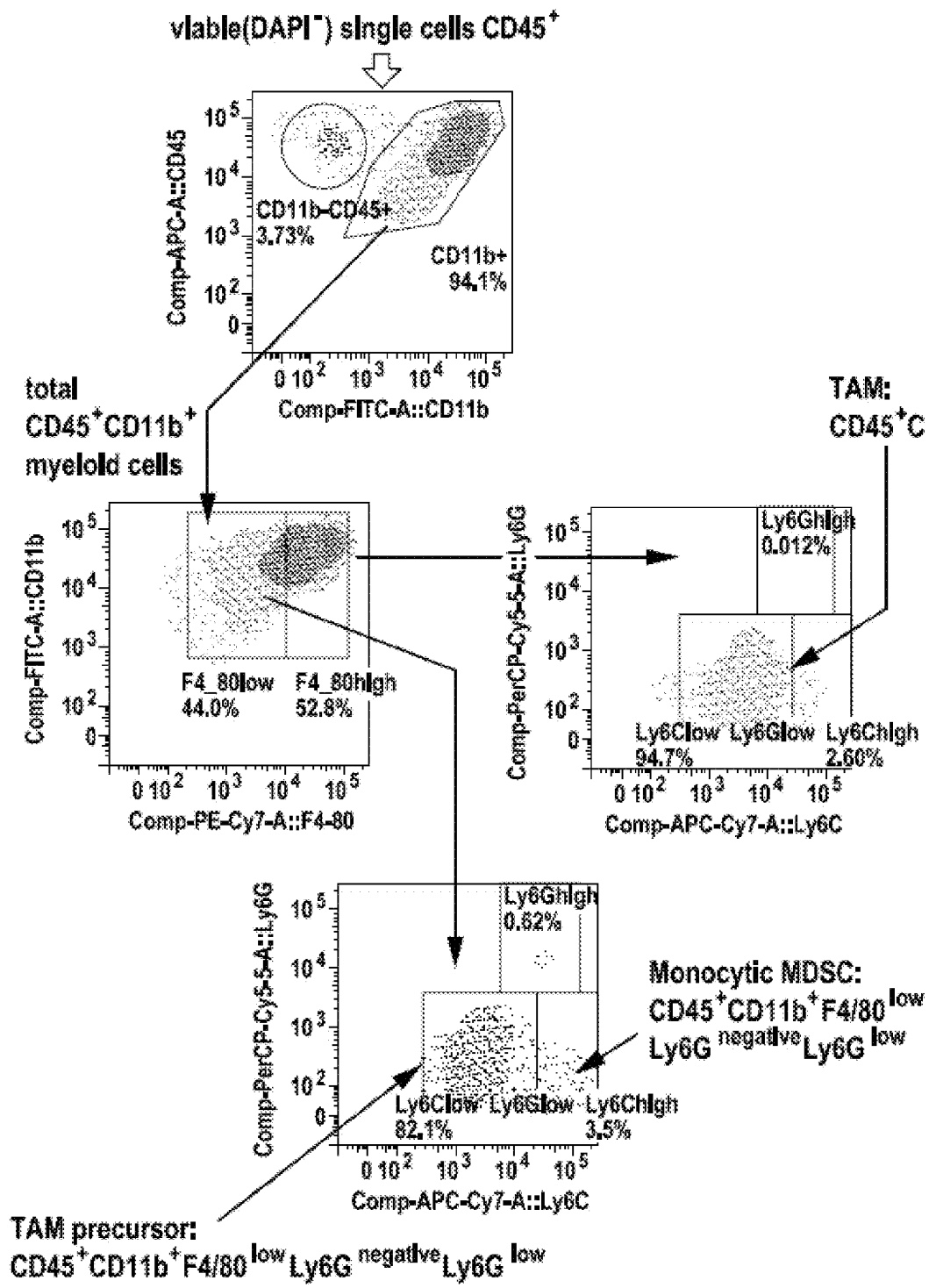
FIG. 4A and FIG. 4B.
Figure 4B:
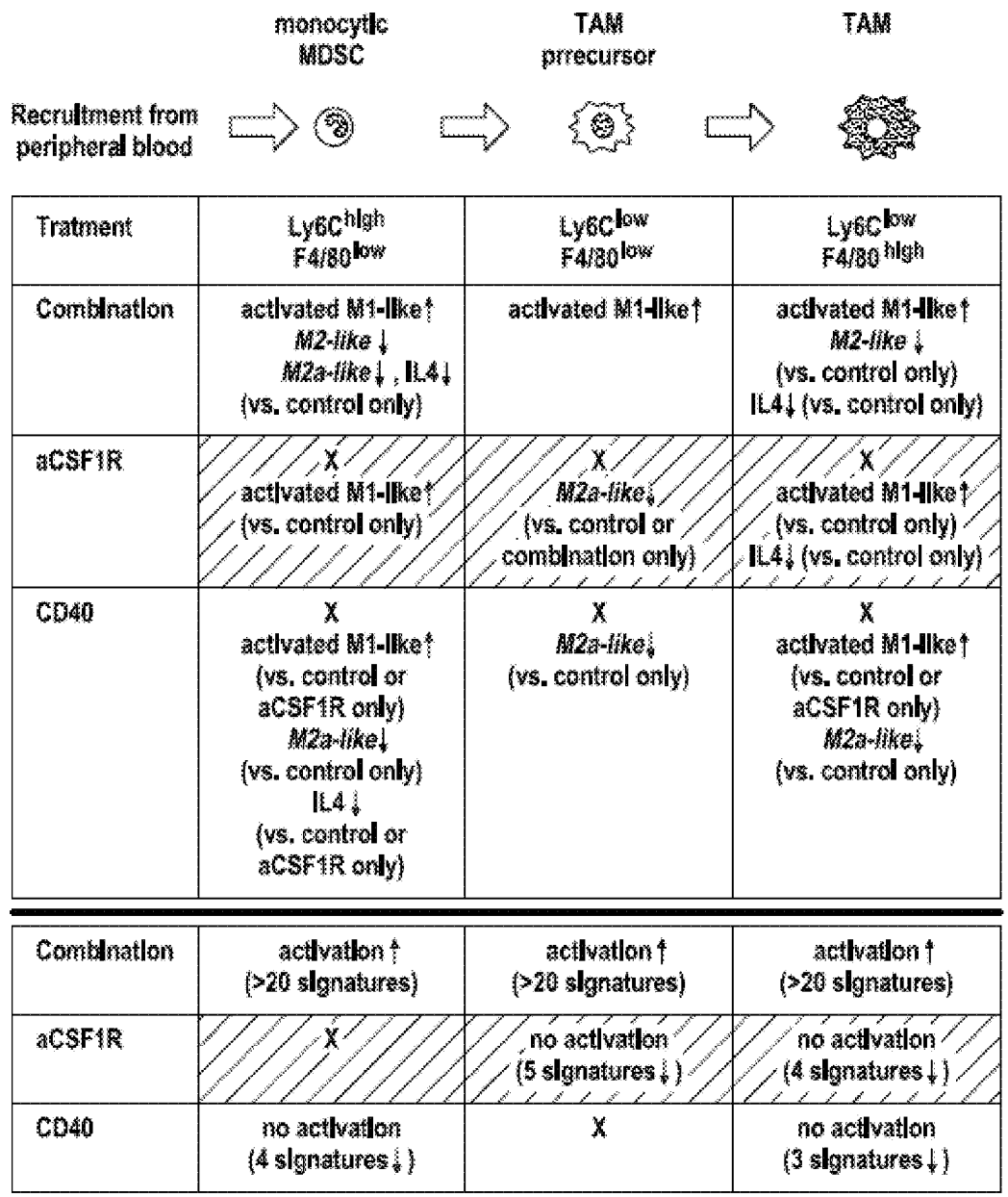

Example 1D: CSF-1R Signaling Blockade Augments CD40 mAb-Regulated Polarization of Tumor-Associated Macrophages (TAM) Towards a Strong Pro-Inflammatory Phenotype (FIGS. 4A and 4B)

Female C57BL/6N mice (6-8 weeks in age, obtained from Charles River) were inoculated with 10$^6$ MC38 colorectal adenocarcinoma tumor cells subcutaneously. Tumor growth curves were monitored by caliper measurement and once tumor size reached 220 mm$^3$ in average, groups were allocated for treatment with the following:

a) IgG isotype control antibody: 30 mg/kg murine IgG1, clone MOPC-21 (BioXCell); or b) anti-CD40 antibody: 4 mg/kg rat IgG2a antibody, clone FGK45 (BioXCell); or c) anti-CSF-1R antibody: 30 mg/kg hamster-mouse chimeric antibody clone 2G2 (Ries et al., Cancer Cell 25:846-859, 2014); or d) combination of anti-CD40 antibody and anti-CSF-1R antibody: combined, simultaneous treatment, dosing as in b) and c).

All antibodies were administered once and tumors were obtained after 16 hours. For cell sorting purpose, tumors were treated and stained as described in Example 1C for flow cytometry. Cells were sorted using a FACS Aria II instrument (BD Bioscience) from 4 animals per group and gated for sorting as shown in FIG. 4A. Three different myeloid cell populations were obtained (10,000 cells minimum per sample were sorted):

a) monocytic MDSC (myeloid-derived suppressor cells): CD45$^+$ CD11b$^+$ F4/80$^{low}$ Ly6G$^{negative}$ Ly6C$^{high}$ b) TAM precursor:
CD45$^+$ CD11b$^+$ F4/80$^{low}$ Ly6G$^{negative}$ Ly6C$^{low}$
c) TAM (tumor-associated macrophages):
CD45$^+$CD11b$^+$F4/80$^{high}$Ly6G$^{negative}$Ly6C$^{low}$ RNA sequencing analysis was performed on sorted cell populations and the raw data processed using in-house tools based on the methods described in the following studies: Langmead, B. & Salzberg, S. L., Nat Methods 9 (2012) 357-359; Mortazavi, A. et al., Nat Methods 5 (2008) 621-628, producing normalized a gene expression value for each gene in each cell population from each treatment group.

Signature analysis was performed on the resulting gene expression values using a publicly available tool (Sandmann, T. et al., Bioinformatics 30 (2014) 127-128). The results are WilcoxoniMann-Whitney rank sum statistics, representing the activation level or likelihood level of the pathway or phenotype represented by a signature in a treatment group compared to another. Three comparisons were performed for each treatment group, e.g. the combination of anti-CD40 antibody and anti-CSF-1R antibody treatment group was compared separately against the anti-CD40, anti-CSF-1R and the IgG isotype control groups.

A signature is a set of functionally-related genes, typically defined from bioinformatics analysis of chemical or genetic perturbation experiments meant to characterize a biological phenotypes of interest, e.g. different macrophage subtypes (M1 vs. M2) or LPS-stimulated macrophages vs. non-stimulated macrophages. 88 signatures of perturbations of various cell types (e.g. immune cells, cancer cells, mammary epithelial cells), involving LPS, interferon or TNF stimulation were used to check for general immune-activation effect. All 88 signatures were obtained from Molecular Signatures Database (MSigDB, Subramanian A. et al., PNAS 102 (2005) 15545-50). Seven signatures were used to check for M1/M2 phenotypes; of these seven, three were obtained from published studies (Schmieder A. et al., Semin Cancer Biol. 22(4) (2012) 289-97; Martinez F. O. et al., Blood 121(9): (2013) e57-69) and four were generated at Roche using gene expression data of in vitro differentiated macrophages profiled on Affymetrix microarray chip.

FIG. 4B summarizes the analysis results for each of the non-control treatment group (rows) and myeloid cell population (columns). "X" indicates no significant or consistent activation/inhibition across all three comparisons for the treatment group. Overall, of the three non-control treatments, the combination of anti-CD40 antibody and anti-CSF-1R antibody is the only treatment to clearly induce activated M1-like effect in all three myeloid subtypes (top panel) and general immune activation-like effect in all three myeloid subtypes (bottom panel) at the time point analyzed.

Figure 5:
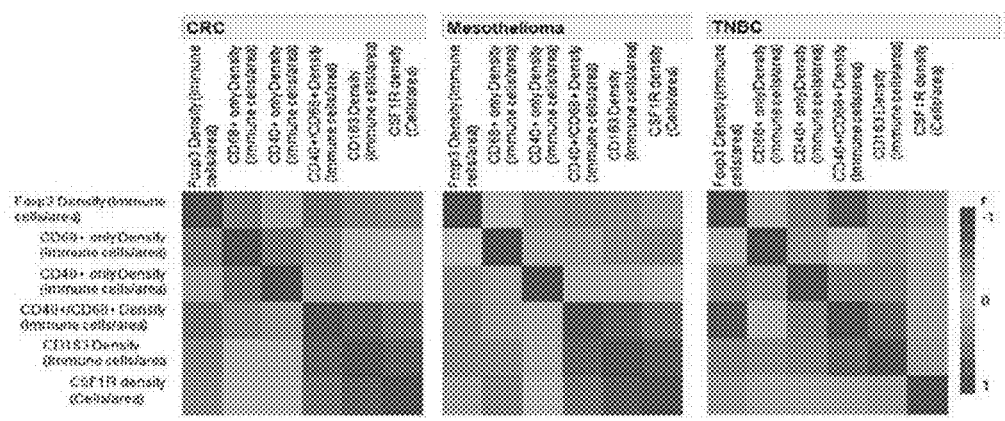
FIG. 5.

Example 1E: CD40 and CSF-1R are Expressed by Human TAMs (IRIS IHC) (FIG. 5)

Patient samples were cut into 2.5 µm formalin-fixed, paraffin-embedded tissue sections from colorectal carcinoma (CRC), Mesothelioma and triple negative breast carcinoma (TNBC). Sections were stained with IHC protocols for FOXP3 (1 µg/mL, 236A/E7, Abcam ab20034). CD40 (1:100, Spring Bioscience, E3704) in a duplex with CD68 (RTU, KP-1. Ventana Medical Systems, 790-2931). CD163 (RTU, MRQ-26, Ventana Medical Systems, 760-4437) and CSF1R (1 µg/mL, 29, Roche Diagnostics GmbH) on the Ventana Benchmark XT using the NEXES Version 10.6 software.

Sections were subjected to CC1 (tris-based cell conditioning 1) treatment for 32 minutes followed by antibody incubation (FOXP3: 1 hour at 37° C., CD40: 32 minutes at 37° C., CD68: 32 minutes at 37° C., CD163: 16 minutes at 37° C., CSF1R: 32 minutes at 37° C.) and positive staining was detected using the OptiView DAB (FOXP3, CD40, CSF1R) detection system or the ultraView-DAB (CD163) or -Red (CD68) detection systems. The slides were scanned at 20× using the Ventana iScan HT bright field scanner and analyzed by a board certified pathologist using algorithms based on the group sparsity model (Chen and Chukka, doi:10.1016/j.compmedimag.2015.04.001).

The resulting density values of the different biomarkers were correlated pairwise amongst each. The resulting correlation coefficients were visualized in heatmaps in FIG. 5 to allow an easy overview of the relationship between the different markers: Red fields show positive correlation, blue fields negative correlation. Amongst others, the density of CSF1R positive cells was positively correlated with CD40$^+$/CD68$^+$ cells, indicating a potential co-expression of these markers, observed significantly in the Mesothelioma and CRC subset. In comparison, no significant correlation was found in the TNBC subsets. (FIG. 5)

Figure 6:
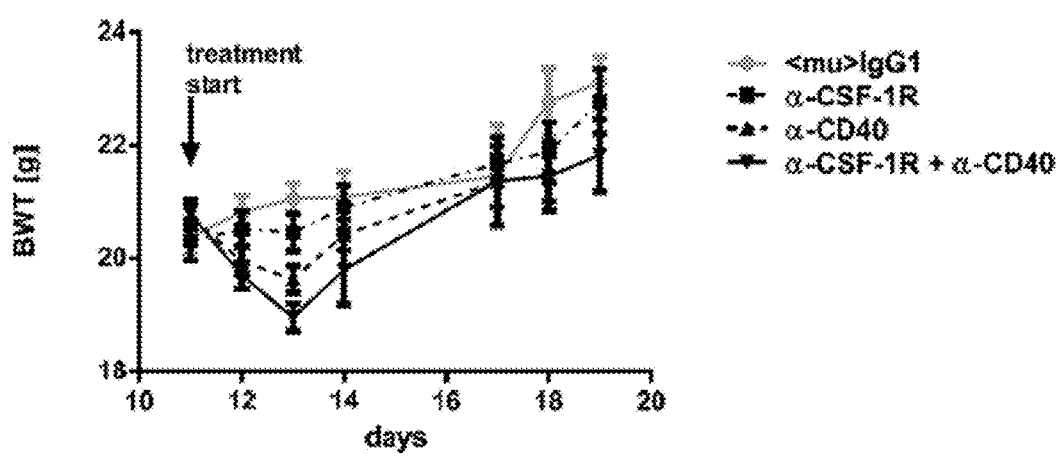
FIG. 6.

Example 1F: CD40 and CSF-1R Combination is Well Tolerated in Pre-Clinical Mouse Models (FIG. 6)

Female C57BL/6N mice (6-8 weeks in age, obtained from Charles River) were inoculated with 10$^6$ MC38 colorectal adenocarcinoma tumor cells subcutaneously. Tumor growth curves were monitored by caliper measurement and once tumor size reached 260 mm$^3$ in average, groups were allocated for treatment with the following:

a) IgG isotype control antibody: 30 mg/kg murine IgG1, clone MOPC-21 (BioXCell); or
b) anti-CD40 antibody: 4 mg/kg rat IgG2A antibody, clone FGK45 (BioXCell); or
c) anti-CSF-1R antibody: 30 mg/kg hamster-mouse chimeric antibody clone 2G2 (Ries et al., Cancer Cell 25:846-859, 2014); or
d) combination of anti-CD40 antibody and anti-CSF-1R antibody: combined, simultaneous treatment, dosing as in b) and c).

All antibodies were administered once on day 11 and body weight of the animals was monitored at the indicated time points. Mean±SEM was calculated from n=5 to 10 mice per group.

Anti-CD40 therapy alone induced a transient body weight loss, which was comparable to the anti-CD40 plus anti-CSF1R combination. On day 17 (6 days after treatment start) no differences in bodyweight were detected compared to the anti-CD40, anti-CSF-1R or IgG control-treated animals (FIG. 6).

Figure 7:
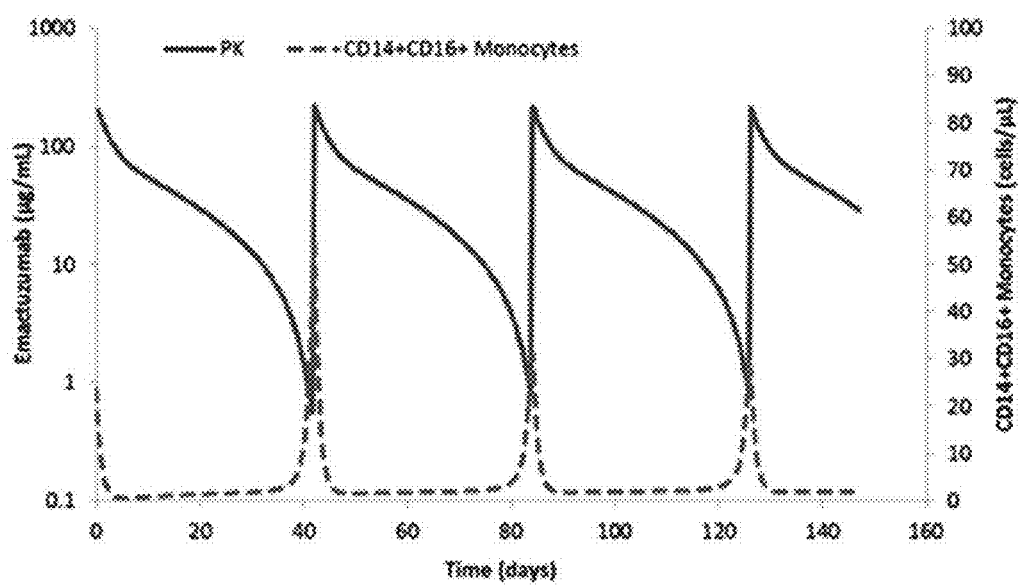
FIG. 7.
Figure 8:
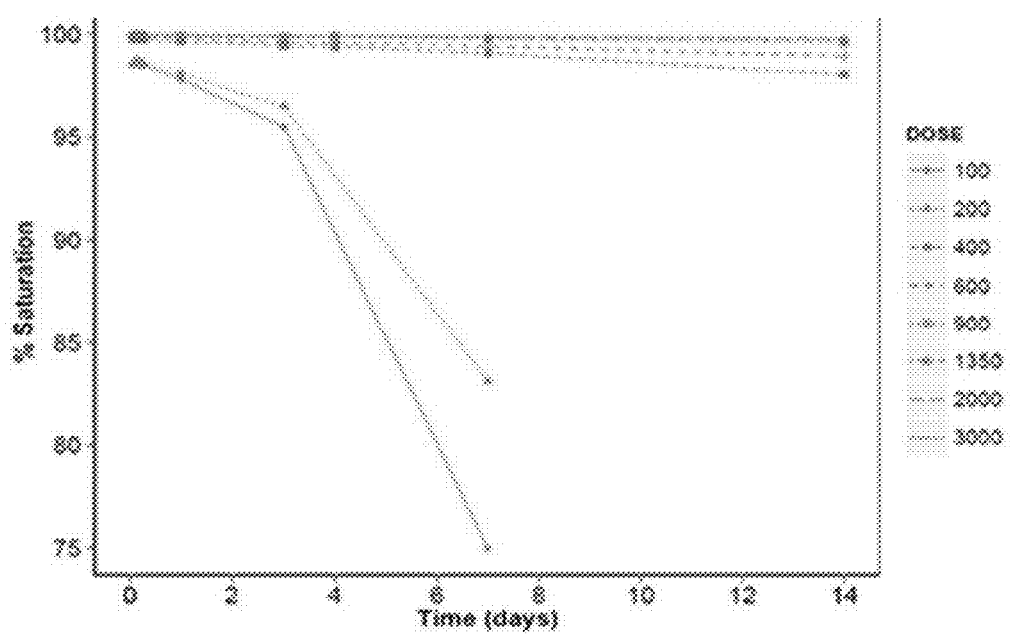
FIG. 8.

Example 1G: Shift of CSF1R Therapy from Continuous to Transient Tumor Associated Macrophage (TAM) Deletion in Combination with Macrophage Activating Agents Like CD40 Agonists (FIGS. 7 and 8)

Dose and Schedule Rationale for Emactuzumab (Anti-CSFR Antibody Comprising VH and VL of SEQU ID NO. 5 and SEQ ID NO: 7, as Ig1 Kappa Constant Domains) in Exploratory Cohort Q6W The alternative treatment schedule aims to investigate whether a re-population of macrophages is beneficial after their initial reduction by emactuzumab dosing. Preclinical models have identified a macrophage dependency to drive maximal efficacy in vivo. In order to allow a repopulation of macrophages a Q6W dosing schedule of emactuzumab will be tested. Fixed (flat) dosing has been selected for this protocol as no strong influence body surface area (BSA) or body weight on overall exposure is expected.

As surrogate for the tumor associated macrophages (TAMs) the precursor human CD14+CD16+ monocytes in blood serum are measured, as the recovery of this blood monocytes correlates with the subsequent recovery of the tumor associated macrophages (TAMs).

A pharmacodynamic model has been fitted to the currently available human CD14+CD16+ monocyte data. Based on preliminary population analysis, a dose of 750 mg administered Q6W shows recovery of CD14+CD16+ monocytes towards the end of the dosing interval of Q6W (~7 days) (FIG. 5). This estimated monocyte recovery is also consistent with the loss of linear PK of emactuzumab and with a decrease of target saturation towards the end of the dosing interval of Q6W (FIG. 7).

Based on a PK analysis from Study BP27772 (100-3000 mg Q2W; N=36 patients), the PK of emactuzumab were shown to be non-linear from 100 up to 900 mg Q2W. Both $C_{max}$ and AUC showed a greater than dose-proportional increase, accompanied by a decrease in total clearance over the same dose-range, which indicates that the elimination of emactuzumab is predominantly target-mediated at exposures achieved with these doses. Above 900 mg, exposure increased in an approximately dose-proportional manner up to 3000 mg, which indicates that the target-mediated elimination was saturated.

A two-compartment PK model that comprises both linear and non-linear clearance pathways has been fitted to the currently available human data. The non-linear clearance pathway may be related to the target levels of receptor at the start of the treatment and could be considered as representing TMDD. The non-linear elimination in the two-compartmental model can also be used to predict the saturation of the target-mediated elimination (surrogate for target saturation). $AUC_{last}$ and CL indicated that the contribution of TMDD to the total CL begins to reduce at doses of 600 mg and reaches a minimum at doses of 900 mg and higher, which indicates that doses ≥900 mg reached ≥90% target saturation (Q2W) (FIG. 8)

A dose/systemic exposure-dependent decrease in macrophages was observed in skin and tumor biopsies from 200 mg onward, which reached a plateau from $C_{ave}$ of 100 µg/mL, which approximately corresponded to a ≥900 mg doses for monotherapy and in combination with paclitaxel. Additional peripheral blood biomarkers were also investigated, such as monocytes and CSF-1 levels. The dose/exposure trends for these peripheral blood biomarkers were similar to the tissue biomarkers (macrophages) and reached a plateau at ≥900 mg. Based on available data to date, to achieve maximum depletion of macrophages, ≥90% target saturation would be required.

Colorectal cancer (CRC) or melanoma (MEL) patients are tested (n=up to 50). The study is to be conducted in a two-step approach to investigate precursor monocyte as well as correlating macrophage recovery by testing an alternative dosing schedule for emactuzumab with a longer dosing interval to allow repopulation of macrophages precursor monocyte as well as correlating macrophage after initial reduction by anti-CSF-1R antibody emactuzumab:

In Step 1a (Run-In), the first 10 patients treated with agonistic CD40 antibody Q3W (at MTD defined in Part I of the study) and emactuzumab Q6W (750 mg) will be analyzed for a potential recovery of TAMs, dermal macrophages as well as circulating monocytes six weeks from the initial emactuzumab infusion. The starting dose of emactuzumab 750 mg Q6W, which was defined based on clinical modelling.

In case TAMs, in n=10 evaluable paired-tumor biopsies, did not recover, a second dose or dosing schedule may be tested in an additional n=10 patients (Step 1 b). The second dose and dosing schedule will be selected from emerging data of the dose-escalation and ongoing expansion cohorts.

In case of observed recovery of TAM at 6 weeks after emactuzumab infusion, up to 30 patients will be further recruited to this expansion cohort (Step 2). In the event that after the first adaption of dose and schedule no TAM recovery was observed, this study arm will be terminated.

Example 1H: Clinical Efficacy in the Sense of Anti-Tumor Activity Will be Assessed as Follows Best overall response.
Overall response rate (ORR), defined as partial response rate plus complete response rate, confirmed by repeated assessments ≥4 weeks after initial documentation.
Progressive-free survival (PFS), defined as the time from first study treatment to the first occurrence of disease progression or death, whichever occurs first.
Duration of response (DOR), defined as the time from the first occurrence of a documented objective response to the time of progression or death from any cause, whichever occurs first.
Clinical benefit rate (CBR), defined as partial response rate plus complete response rate plus stable disease rate.
Best overall response, objective response and disease progression will be determined by Investigator assessment and by central review using both conventional RECIST v1.1 and modified RECIST criteria. Optional submission of the latest (not older than 6 months prior to Cycle 1 Day 1) pre-study computed tomography (CT) scans (historical CT scans) is highly encouraged if available. This scan will be compared to those collected during the study to determine longitudinal tumor-growth kinetics.

The invention claimed is:

1. A method of treating cancer in a patient having a tumor with a colony stimulating factor-1 receptor (CSF-1R)-expressing macrophage infiltrate with an antibody that binds to human CSF-1R, wherein the anti-CSF-1R antibody is administered in a treatment cycle in combination with a macrophage-activating agent, wherein the macrophage-activating agent is an agonistic CD40 antibody, and wherein the anti-CSF-1R antibody comprises a heavy chain variable domain VH of SEQ ID NO:5 and a light chain variable domain VL of SEQ ID NO:6, and the agonistic CD40 antibody comprises a heavy chain variable domain VH of SEQ ID NO: 11 and a light chain variable domain VL of SEQ ID NO: 12.

2. A method of treating cancer in a patient having a tumor with a colony stimulating factor-1 receptor (CSF-1R)-expressing macrophage infiltrate with an antibody that binds to human CSF-1R, wherein the anti-CSF-1R antibody is administered in a first treatment cycle in combination with a macrophage-activating agent, wherein the macrophage-activating agent is an agonistic CD40 antibody, wherein the anti-CSF-1R antibody comprises a heavy chain variable domain VH of SEQ ID NO:5 and a light chain variable domain VL of SEQ ID NO:6, and the agonistic CD40 antibody comprises a heavy chain variable domain VH of SEQ ID NO: 11 and a light chain variable domain VL of SEQ ID NO: 12, and wherein in subsequent treatment cycles the anti-CSF-1R antibody is administered only in combination with the macrophage-activating agent after a significant recovery of a) CD14+CD16+ positive monocytes in blood serum or b) CD163+/CD68+ positive tumor-associated macrophages.

3. The method of claim 2, wherein in the subsequent treatment cycles the anti-CSF-1R antibody is administered only at every second cycle in combination with the macrophage-activating agent, while the macrophage-activating agent is administered at each treatment cycle.

4. The method of claim 1 or 2, wherein the length of the treatment cycle is between 2 and 4 weeks.

5. The method of claim 1 or 2, wherein the anti-CSF-1R antibody is administered at a dose of 600-1200 mg.

6. The method of claim 1 or 2, wherein the agonistic CD40 antibody is administered at a dose of 4-16 mg at each cycle.

7. The method of claim 1 or 2, wherein the combined therapy is for use in treating or delaying progression of an immune-related disease.

8. The method of claim 1 or 2, wherein the combined therapy is for use in stimulating an immune response.

9. The method of claim 2, wherein the significant recovery of CD14+CD16+ positive monocytes in blood serum is a recovery of more than 60%.

10. The method of claim 2, wherein the significant recovery of CD14+CD16+ positive monocytes in blood serum is a recovery of more than 80%.

11. The method of claim 2, wherein the significant recovery of CD163+/CD68+ positive tumor-associated macrophages is a recovery of more than 60%.

12. The method of claim 2, wherein the significant recovery of CD163+/CD68+ positive tumor-associated macrophages is a recovery of more than 80%.

* * * * *

SEQUENCE LISTING

```
<160> NUMBER OF SEQ ID NOS: 37

<210> SEQ ID NO 1
<211> LENGTH: 116
<212> TYPE: PRT
<213> ORGANISM: Artificial
<220> FEATURE:
<223> OTHER INFORMATION: heavy chain variable domain, hMab 2F11-c11
```

```
<400> SEQUENCE: 1

Gln Val Gln Leu Val Gln Ser Gly Ala Glu Val Lys Lys Pro Gly Ser
1               5                   10                  15

Ser Val Lys Val Ser Cys Lys Ala Ser Gly Phe Ser Leu Thr Thr Tyr
            20                  25                  30

Asp Ile Ser Trp Ile Arg Gln Ala Pro Gly Gln Gly Leu Glu Trp Met
        35                  40                  45

Gly Val Ile Trp Thr Asp Gly Gly Thr Asn Tyr Asn Ser Pro Phe Met
50                  55                  60

Ser Arg Val Thr Ile Thr Lys Asp Glu Ser Thr Ser Thr Ala Tyr Met
65                  70                  75                  80

Glu Leu Ser Ser Leu Arg Ser Glu Asp Thr Ala Val Tyr Tyr Cys Val
                85                  90                  95

Arg Asp Gln Arg Leu Tyr Phe Asp Val Trp Gly Gln Gly Thr Thr Val
            100                 105                 110

Thr Val Ser Ser
            115

<210> SEQ ID NO 2
<211> LENGTH: 106
<212> TYPE: PRT
<213> ORGANISM: Artificial
<220> FEATURE:
<223> OTHER INFORMATION: light chain variable domain, hMab 2F11-c11

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asp Val Asn Thr Tyr
            20                  25                  30

Val Ser Trp Tyr Gln Gln Lys Pro Gly Lys Ala Pro Lys Leu Leu Ile
        35                  40                  45

Tyr Gly Ala Ser Asn Arg Tyr Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gly Gln Ser Phe Ser Tyr Pro Thr
                85                  90                  95

Phe Gly Gln Gly Thr Lys Leu Glu Ile Lys
            100                 105

<210> SEQ ID NO 3
<211> LENGTH: 116
<212> TYPE: PRT
<213> ORGANISM: Artificial
<220> FEATURE:
<223> OTHER INFORMATION: heavy chain variable domain, hMab 2F11-d8

<400> SEQUENCE: 3

Gln Val Gln Leu Val Gln Ser Gly Ala Glu Val Lys Lys Pro Gly Ser
1               5                   10                  15

Ser Val Lys Val Ser Cys Lys Ala Ser Gly Phe Ser Leu Thr Thr Tyr
            20                  25                  30

Asp Ile Ser Trp Val Arg Gln Ala Pro Gly Gln Gly Leu Glu Trp Met
        35                  40                  45

Gly Val Ile Trp Thr Asp Gly Gly Ala Asn Tyr Ala Gln Lys Phe Gln
50                  55                  60
```

Gly Arg Val Thr Ile Thr Ala Asp Glu Ser Thr Ser Thr Ala Tyr Met
65                  70                  75                  80

Glu Leu Ser Ser Leu Arg Ser Glu Asp Thr Ala Val Tyr Tyr Cys Ala
                85                  90                  95

Arg Asp Gln Arg Leu Tyr Phe Asp Val Trp Gly Gln Gly Thr Thr Val
            100                 105                 110

Thr Val Ser Ser
            115

<210> SEQ ID NO 4
<211> LENGTH: 106
<212> TYPE: PRT
<213> ORGANISM: Artificial
<220> FEATURE:
<223> OTHER INFORMATION: light chain variable domain, hMab 2F11-d8

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Lys Ala Ser Glu Asp Val Asn Thr Tyr
            20                  25                  30

Val Ser Trp Tyr Gln Gln Lys Pro Gly Lys Ala Pro Lys Leu Leu Ile
        35                  40                  45

Tyr Gly Ala Ser Asn Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gly Gln Ser Phe Ser Tyr Pro Thr
                85                  90                  95

Phe Gly Gln Gly Thr Lys Leu Glu Ile Lys
            100                 105

<210> SEQ ID NO 5
<211> LENGTH: 116
<212> TYPE: PRT
<213> ORGANISM: Artificial
<220> FEATURE:
<223> OTHER INFORMATION: heavy chain variable domain, hMab 2F11-e7

<400> SEQUENCE: 5

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Ser Trp Val Arg Gln Ala Pro Gly Gln Gly Leu Glu Trp Met
        35                  40                  45

Gly Val Ile Trp Thr Asp Gly Gly Thr Asn Tyr Ala Gln Lys Leu Gln
    50                  55                  60

Gly Arg Val Thr Met Thr Thr Asp Thr Ser Thr Ser Thr Ala Tyr Met
65                  70                  75                  80

Glu Leu Arg Ser Leu Arg Ser Asp Asp Thr Ala Val Tyr Tyr Cys Ala
                85                  90                  95

Arg Asp Gln Arg Leu Tyr Phe Asp Val Trp Gly Gln Gly Thr Thr Val
            100                 105                 110

Thr Val Ser Ser
            115

```
<210> SEQ ID NO 6
<211> LENGTH: 106
<212> TYPE: PRT
<213> ORGANISM: Artificial
<220> FEATURE:
<223> OTHER INFORMATION: light chain variable domain, hMab 2F11-e7

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asp Val Asn Thr Tyr
            20                  25                  30

Val Ser Trp Tyr Gln Gln Lys Pro Gly Lys Ala Pro Lys Leu Leu Ile
        35                  40                  45

Tyr Ala Ala Ser Asn Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Phe Ser Tyr Pro Thr
                85                  90                  95

Phe Gly Gln Gly Thr Lys Leu Glu Ile Lys
            100                 105

<210> SEQ ID NO 7
<211> LENGTH: 116
<212> TYPE: PRT
<213> ORGANISM: Artificial
<220> FEATURE:
<223> OTHER INFORMATION: heavy chain variable domain, hMab 2F11-f12

<400> SEQUENCE: 7

Gln Val Gln Leu Val Gln Ser Gly Ala Glu Val Lys Lys Pro Gly Ser
1               5                   10                  15

Ser Val Lys Val Ser Cys Lys Ala Ser Gly Phe Ser Leu Thr Thr Tyr
            20                  25                  30

Asp Ile Ser Trp Val Arg Gln Ala Pro Gly Gln Gly Leu Glu Trp Met
        35                  40                  45

Gly Val Ile Trp Thr Asp Gly Gly Thr Asn Tyr Asn Ser Pro Phe Met
    50                  55                  60

Ser Arg Val Thr Ile Thr Lys Asp Glu Ser Thr Ser Thr Ala Tyr Met
65                  70                  75                  80

Glu Leu Ser Ser Leu Arg Ser Glu Asp Thr Ala Val Tyr Tyr Cys Val
                85                  90                  95

Arg Asp Gln Arg Leu Tyr Phe Asp Val Trp Gly Gln Gly Thr Thr Val
            100                 105                 110

Thr Val Ser Ser
        115

<210> SEQ ID NO 8
<211> LENGTH: 106
<212> TYPE: PRT
<213> ORGANISM: Artificial
<220> FEATURE:
<223> OTHER INFORMATION: light chain variable domain, hMab 2F11-f12

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asp Val Asn Thr Tyr
            20                  25                  30
```

```
Val Ser Trp Tyr Gln Gln Lys Pro Gly Lys Ala Pro Lys Leu Leu Ile
         35                  40                  45

Tyr Gly Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gly Gln Ser Phe Ser Tyr Pro Thr
                 85                  90                  95

Phe Gly Gln Gly Thr Lys Leu Glu Ile Lys
                100                 105

<210> SEQ ID NO 9
<211> LENGTH: 116
<212> TYPE: PRT
<213> ORGANISM: Artificial
<220> FEATURE:
<223> OTHER INFORMATION: heavy chain variable domain, hMab 2F11-g1

<400> SEQUENCE: 9

Gln Val Gln Leu Gln Glu Ser Gly Pro Gly Leu Val Lys Pro Ser Glu
 1               5                  10                  15

Thr Leu Ser Leu Thr Cys Thr Val Ser Gly Phe Ser Leu Thr Thr Tyr
                 20                  25                  30

Asp Ile Ser Trp Ile Arg Gln Pro Pro Gly Lys Gly Leu Glu Trp Ile
                 35                  40                  45

Gly Val Ile Trp Thr Asp Gly Thr Asn Tyr Asn Ser Pro Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Asp Gln Arg Leu Tyr Phe Asp Val Trp Gly Gln Gly Thr Thr Val
                100                 105                 110

Thr Val Ser Ser
        115

<210> SEQ ID NO 10
<211> LENGTH: 106
<212> TYPE: PRT
<213> ORGANISM: Artificial
<220> FEATURE:
<223> OTHER INFORMATION: light chain variable domain, hMab 2F11-g1

<400> SEQUENCE: 10

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Glu Asp Val Asn Thr Tyr
                 20                  25                  30

Leu Ala Trp Tyr Gln Gln Lys Pro Gly Gln Ala Pro Arg Leu Leu Ile
                 35                  40                  45

Tyr Gly Ala Ser Ser Arg Ala Thr Gly Ile Pro Asp Arg Phe Ser Gly
 50                  55                  60

Ser Gly Ser Gly Thr Asp Phe Thr Leu Thr Ile Ser Arg Leu Glu Pro
 65                  70                  75                  80

Glu Asp Phe Ala Val Tyr Tyr Cys Gly Gln Ser Phe Ser Tyr Pro Thr
                 85                  90                  95

Phe Gly Gln Gly Thr Lys Leu Glu Ile Lys
                100                 105
```

```
<210> SEQ ID NO 11
<211> LENGTH: 126
<212> TYPE: PRT
<213> ORGANISM: Homo sapiens

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asp Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Asn Arg Leu Arg Ser Asp Asp Thr Ala Val Tyr Tyr Cys
                85                  90                  95

Ala Arg Asp Gln Pro Leu Gly Tyr Cys Thr Asn Gly Val Cys Ser Tyr
            100                 105                 110

Phe Asp Tyr Trp Gly Gln Gly Thr Leu Val Thr Val Ser Ser
        115                 120                 125

<210> SEQ ID NO 12
<211> LENGTH: 107
<212> TYPE: PRT
<213> ORGANISM: Homo sapiens

<400> SEQUENCE: 12

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Tyr Ser Trp
            20                  25                  30

Leu Ala Trp Tyr Gln Gln Lys Pro Gly Lys Ala Pro Asn Leu Leu Ile
        35                  40                  45

Tyr Thr Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ile Phe Pro Leu
                85                  90                  95

Thr Phe Gly Gly Gly Thr Lys Val Glu Ile Lys
            100                 105

<210> SEQ ID NO 13
<211> LENGTH: 113
<212> TYPE: PRT
<213> ORGANISM: Artificial
<220> FEATURE:
<223> OTHER INFORMATION: humanized S2C6 heavy chain variabel domain
      variant

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Tyr Ile His Trp Val Arg Gln Ala Pro Gly Lys Gly Leu Glu Trp Val
        35                  40                  45
```

```
Ala Arg Val Ile Pro Asn Ala Gly Gly Thr Ser Tyr Asn Gln Lys Phe
     50                  55                  60

Lys Gly Arg Phe Thr Leu Ser Val Asp Asn Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Glu Gly Ile Tyr Trp Trp Gly Gln Gly Thr Leu Val Thr Val
             100                 105                 110

Ser

<210> SEQ ID NO 14
<211> LENGTH: 113
<212> TYPE: PRT
<213> ORGANISM: Artificial
<220> FEATURE:
<223> OTHER INFORMATION: humanized S2C6 light chain variabel domain
      variant

<400> SEQUENCE: 14

Asp Ile Gln Met Thr Gln Ser Pro Ser Ser Leu Ser Ala Ser Val Gly
 1               5                  10                  15

Asp Arg Val Thr Ile Thr Cys Arg Ser Ser Gln Ser Leu Val His Ser
                 20                  25                  30

Asn Gly Asn Thr Phe Leu His Trp Tyr Gln Gln Lys Pro Gly Lys Ala
             35                  40                  45

Pro Lys Leu Leu Ile Tyr Thr Val Ser Asn Arg Phe Ser Gly Val Pro
 50                  55                  60

Ser Arg Phe Ser Gly Ser Gly Ser Gly Thr Asp Phe Thr Leu Thr Ile
 65                  70                  75                  80

Ser Ser Leu Gln Pro Glu Asp Phe Ala Thr Tyr Phe Cys Ser Gln Thr
                 85                  90                  95

Thr His Val Pro Trp Thr Phe Gly Gln Gly Thr Lys Val Glu Ile Lys
             100                 105                 110

Arg

<210> SEQ ID NO 15
<211> LENGTH: 118
<212> TYPE: PRT
<213> ORGANISM: Artificial
<220> FEATURE:
<223> OTHER INFORMATION: heavy chain variable domain of anti-PD-L1
      antibody atezolizumab

<400> SEQUENCE: 15

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Ser
                 20                  25                  30

Trp Ile His Trp Val Arg Gln Ala Pro Gly Lys Gly Leu Glu Trp Val
             35                  40                  45

Ala Trp Ile Ser Pro Tyr Gly Gly Ser Thr Tyr Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95
```

```
Ala Arg Arg His Trp Pro Gly Gly Phe Asp Tyr Trp Gly Gln Gly Thr
            100                 105                 110

Leu Val Thr Val Ser Ser
        115

<210> SEQ ID NO 16
<211> LENGTH: 108
<212> TYPE: PRT
<213> ORGANISM: Artificial
<220> FEATURE:
<223> OTHER INFORMATION: light chain variable domain of anti-PD-L1
      antibody atezolizumab

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg
            100                 105

<210> SEQ ID NO 17
<211> LENGTH: 20
<212> TYPE: DNA
<213> ORGANISM: Artificial
<220> FEATURE:
<223> OTHER INFORMATION: unmethylated cytosine-phosphate-guanosine (CpG)
      motif containing oligodeoxynucleotide CpG ODN 2216

<400> SEQUENCE: 17 ggggggacgat cgtcgggggg                                            20

<210> SEQ ID NO 18
<211> LENGTH: 19
<212> TYPE: DNA
<213> ORGANISM: Artificial
<220> FEATURE:
<223> OTHER INFORMATION: unmethylated cytosine-phosphate-guanosine (CpG)
      motif containing oligodeoxynucleotide CpG ODN PB4

<400> SEQUENCE: 18
tcggacgatc gtcggggggg                                             19

<210> SEQ ID NO 19
<211> LENGTH: 22
<212> TYPE: DNA
<213> ORGANISM: Artificial
<220> FEATURE:
<223> OTHER INFORMATION: unmethylated cytosine-phosphate-guanosine (CpG)
      motif containing oligodeoxynucleotide CpG ODN 1002

<400> SEQUENCE: 19
ggggtcgttc gtcgttgggg gg                                          22
```

```
<210> SEQ ID NO 20
<211> LENGTH: 24
<212> TYPE: DNA
<213> ORGANISM: Artificial
<220> FEATURE:
<223> OTHER INFORMATION: unmethylated cytosine-phosphate-guanosine (CpG)
      motif containing oligodeoxynucleotide CpG-7909 (Agatolimod)

<400> SEQUENCE: 20
tcgtcgtttt gtcgttttgt cgtt                                          24

<210> SEQ ID NO 21
<211> LENGTH: 21
<212> TYPE: DNA
<213> ORGANISM: Artificial
<220> FEATURE:
<223> OTHER INFORMATION: unmethylated cytosine-phosphate-guanosine (CpG)
      motif containing oligodeoxynucleotide CpG-685 (GNKG168)

<400> SEQUENCE: 21
tcgtcgacgt cgttcgttct c                                             21

<210> SEQ ID NO 22
<211> LENGTH: 23
<212> TYPE: DNA
<213> ORGANISM: Artificial
<220> FEATURE:
<223> OTHER INFORMATION: unmethylated cytosine-phosphate-guanosine (CpG)
      motif containing oligodeoxynucleotide CpG-684

<400> SEQUENCE: 22
tcgacgttcg tcgttcgtcg ttc                                           23

<210> SEQ ID NO 23
<211> LENGTH: 26
<212> TYPE: DNA
<213> ORGANISM: Artificial
<220> FEATURE:
<223> OTHER INFORMATION: unmethylated cytosine-phosphate-guanosine (CpG)
      motif containing oligodeoxynucleotide CpG-28

<400> SEQUENCE: 23
taaacgttat aacgttatga cgtcat                                        26

<210> SEQ ID NO 24
<211> LENGTH: 972
<212> TYPE: PRT
<213> ORGANISM: Homo sapiens

<400> SEQUENCE: 24

Met Gly Pro Gly Val Leu Leu Leu Leu Val Ala Thr Ala Trp His
1               5                   10                  15

Gly Gln Gly Ile Pro Val Ile Glu Pro Ser Val Pro Glu Leu Val Val
            20                  25                  30

Lys Pro Gly Ala Thr Val Thr Leu Arg Cys Val Gly Asn Gly Ser Val
        35                  40                  45

Glu Trp Asp Gly Pro Pro Ser Pro His Trp Thr Leu Tyr Ser Asp Gly
    50                  55                  60

Ser Ser Ser Ile Leu Ser Thr Asn Asn Ala Thr Phe Gln Asn Thr Gly
65                  70                  75                  80

Thr Tyr Arg Cys Thr Glu Pro Gly Asp Pro Leu Gly Gly Ser Ala Ala
                85                  90                  95

Ile His Leu Tyr Val Lys Asp Pro Ala Arg Pro Trp Asn Val Leu Ala
            100                 105                 110
```

```
Gln Glu Val Val Phe Glu Asp Gln Asp Ala Leu Leu Pro Cys Leu
            115                 120                 125

Leu Thr Asp Pro Val Leu Glu Ala Gly Val Ser Leu Val Arg Val Arg
130                 135                 140

Gly Arg Pro Leu Met Arg His Thr Asn Tyr Ser Phe Ser Pro Trp His
145                 150                 155                 160

Gly Phe Thr Ile His Arg Ala Lys Phe Ile Gln Ser Gln Asp Tyr Gln
                165                 170                 175

Cys Ser Ala Leu Met Gly Gly Arg Lys Val Met Ser Ile Ser Ile Arg
            180                 185                 190

Leu Lys Val Gln Lys Val Ile Pro Gly Pro Ala Leu Thr Leu Val
        195                 200                 205

Pro Ala Glu Leu Val Arg Ile Arg Gly Glu Ala Ala Gln Ile Val Cys
210                 215                 220

Ser Ala Ser Ser Val Asp Val Asn Phe Asp Val Phe Leu Gln His Asn
225                 230                 235                 240

Asn Thr Lys Leu Ala Ile Pro Gln Gln Ser Asp Phe His Asn Asn Arg
                245                 250                 255

Tyr Gln Lys Val Leu Thr Leu Asn Leu Asp Gln Val Asp Phe Gln His
            260                 265                 270

Ala Gly Asn Tyr Ser Cys Val Ala Ser Asn Val Gln Gly Lys His Ser
        275                 280                 285

Thr Ser Met Phe Phe Arg Val Val Glu Ser Ala Tyr Leu Asn Leu Ser
290                 295                 300

Ser Glu Gln Asn Leu Ile Gln Glu Val Thr Val Gly Glu Gly Leu Asn
305                 310                 315                 320

Leu Lys Val Met Val Glu Ala Tyr Pro Gly Leu Gln Gly Phe Asn Trp
                325                 330                 335

Thr Tyr Leu Gly Pro Phe Ser Asp His Gln Pro Glu Pro Lys Leu Ala
            340                 345                 350

Asn Ala Thr Thr Lys Asp Thr Tyr Arg His Thr Phe Thr Leu Ser Leu
        355                 360                 365

Pro Arg Leu Lys Pro Ser Glu Ala Gly Arg Tyr Ser Phe Leu Ala Arg
370                 375                 380

Asn Pro Gly Gly Trp Arg Ala Leu Thr Phe Glu Leu Thr Leu Arg Tyr
385                 390                 395                 400

Pro Pro Glu Val Ser Val Ile Trp Thr Phe Ile Asn Gly Ser Gly Thr
                405                 410                 415

Leu Leu Cys Ala Ala Ser Gly Tyr Pro Gln Pro Asn Val Thr Trp Leu
            420                 425                 430

Gln Cys Ser Gly His Thr Asp Arg Cys Asp Glu Ala Gln Val Leu Gln
        435                 440                 445

Val Trp Asp Asp Pro Tyr Pro Glu Val Leu Ser Gln Glu Pro Phe His
450                 455                 460

Lys Val Thr Val Gln Ser Leu Leu Thr Val Glu Thr Leu Glu His Asn
465                 470                 475                 480

Gln Thr Tyr Glu Cys Arg Ala His Asn Ser Val Gly Ser Gly Ser Trp
                485                 490                 495

Ala Phe Ile Pro Ile Ser Ala Gly Ala His Thr His Pro Pro Asp Glu
            500                 505                 510

Phe Leu Phe Thr Pro Val Val Val Ala Cys Met Ser Ile Met Ala Leu
        515                 520                 525
```

```
Leu Leu Leu Leu Leu Leu Leu Leu Tyr Lys Tyr Lys Gln Lys Pro
    530                 535                 540
Lys Tyr Gln Val Arg Trp Lys Ile Ile Glu Ser Tyr Glu Gly Asn Ser
545                 550                 555                 560
Tyr Thr Phe Ile Asp Pro Thr Gln Leu Pro Tyr Asn Glu Lys Trp Glu
                565                 570                 575
Phe Pro Arg Asn Asn Leu Gln Phe Gly Lys Thr Leu Gly Ala Gly Ala
            580                 585                 590
Phe Gly Lys Val Val Glu Ala Thr Ala Phe Gly Leu Gly Lys Glu Asp
        595                 600                 605
Ala Val Leu Lys Val Ala Val Lys Met Leu Lys Ser Thr Ala His Ala
    610                 615                 620
Asp Glu Lys Glu Ala Leu Met Ser Glu Leu Lys Ile Met Ser His Leu
625                 630                 635                 640
Gly Gln His Glu Asn Ile Val Asn Leu Leu Gly Ala Cys Thr His Gly
                645                 650                 655
Gly Pro Val Leu Val Ile Thr Glu Tyr Cys Cys Tyr Gly Asp Leu Leu
            660                 665                 670
Asn Phe Leu Arg Arg Lys Ala Glu Ala Met Leu Gly Pro Ser Leu Ser
        675                 680                 685
Pro Gly Gln Asp Pro Glu Gly Gly Val Asp Tyr Lys Asn Ile His Leu
    690                 695                 700
Glu Lys Lys Tyr Val Arg Arg Asp Ser Gly Phe Ser Ser Gln Gly Val
705                 710                 715                 720
Asp Thr Tyr Val Glu Met Arg Pro Val Ser Thr Ser Ser Asn Asp Ser
                725                 730                 735
Phe Ser Glu Gln Asp Leu Asp Lys Glu Asp Gly Arg Pro Leu Glu Leu
            740                 745                 750
Arg Asp Leu Leu His Phe Ser Ser Gln Val Ala Gln Gly Met Ala Phe
        755                 760                 765
Leu Ala Ser Lys Asn Cys Ile His Arg Asp Val Ala Ala Arg Asn Val
    770                 775                 780
Leu Leu Thr Asn Gly His Val Ala Lys Ile Gly Asp Phe Gly Leu Ala
785                 790                 795                 800
Arg Asp Ile Met Asn Asp Ser Asn Tyr Ile Val Lys Gly Asn Ala Arg
                805                 810                 815
Leu Pro Val Lys Trp Met Ala Pro Glu Ser Ile Phe Asp Cys Val Tyr
            820                 825                 830
Thr Val Gln Ser Asp Val Trp Ser Tyr Gly Ile Leu Leu Trp Glu Ile
        835                 840                 845
Phe Ser Leu Gly Leu Asn Pro Tyr Pro Gly Ile Leu Val Asn Ser Lys
    850                 855                 860
Phe Tyr Lys Leu Val Lys Asp Gly Tyr Gln Met Ala Gln Pro Ala Phe
865                 870                 875                 880
Ala Pro Lys Asn Ile Tyr Ser Ile Met Gln Ala Cys Trp Ala Leu Glu
                885                 890                 895
Pro Thr His Arg Pro Thr Phe Gln Gln Ile Cys Ser Phe Leu Gln Glu
            900                 905                 910
Gln Ala Gln Glu Asp Arg Arg Glu Arg Asp Tyr Thr Asn Leu Pro Ser
        915                 920                 925
Ser Ser Arg Ser Gly Gly Ser Gly Ser Ser Ser Ser Glu Leu Glu Glu
    930                 935                 940
```

```
Glu Ser Ser Ser Glu His Leu Thr Cys Cys Glu Gln Gly Asp Ile Ala
945                 950                 955                 960

Gln Pro Leu Leu Gln Pro Asn Asn Tyr Gln Phe Cys
                965                 970

<210> SEQ ID NO 25
<211> LENGTH: 493
<212> TYPE: PRT
<213> ORGANISM: Artificial
<220> FEATURE:
<223> OTHER INFORMATION: human CSF-1R Extracellular Domain

<400> SEQUENCE: 25

Ile Pro Val Ile Glu Pro Ser Val Pro Glu Leu Val Val Lys Pro Gly
1               5                   10                  15

Ala Thr Val Thr Leu Arg Cys Val Gly Asn Gly Ser Val Glu Trp Asp
                20                  25                  30

Gly Pro Pro Ser Pro His Trp Thr Leu Tyr Ser Asp Gly Ser Ser Ser
            35                  40                  45

Ile Leu Ser Thr Asn Asn Ala Thr Phe Gln Asn Thr Gly Thr Tyr Arg
    50                  55                  60

Cys Thr Glu Pro Gly Asp Pro Leu Gly Gly Ser Ala Ala Ile His Leu
65                  70                  75                  80

Tyr Val Lys Asp Pro Ala Arg Pro Trp Asn Val Leu Ala Gln Glu Val
                85                  90                  95

Val Val Phe Glu Asp Gln Asp Ala Leu Leu Pro Cys Leu Leu Thr Asp
            100                 105                 110

Pro Val Leu Glu Ala Gly Val Ser Leu Val Arg Val Arg Gly Arg Pro
        115                 120                 125

Leu Met Arg His Thr Asn Tyr Ser Phe Ser Pro Trp His Gly Phe Thr
130                 135                 140

Ile His Arg Ala Lys Phe Ile Gln Ser Gln Asp Tyr Gln Cys Ser Ala
145                 150                 155                 160

Leu Met Gly Gly Arg Lys Val Met Ser Ile Ser Ile Arg Leu Lys Val
                165                 170                 175

Gln Lys Val Ile Pro Gly Pro Pro Ala Leu Thr Leu Val Pro Ala Glu
            180                 185                 190

Leu Val Arg Ile Arg Gly Glu Ala Ala Gln Ile Val Cys Ser Ala Ser
        195                 200                 205

Ser Val Asp Val Asn Phe Asp Val Phe Leu Gln His Asn Asn Thr Lys
210                 215                 220

Leu Ala Ile Pro Gln Gln Ser Asp Phe His Asn Asn Arg Tyr Gln Lys
225                 230                 235                 240

Val Leu Thr Leu Asn Leu Asp Gln Val Asp Phe Gln His Ala Gly Asn
                245                 250                 255

Tyr Ser Cys Val Ala Ser Asn Val Gln Gly Lys His Ser Thr Ser Met
            260                 265                 270

Phe Phe Arg Val Val Glu Ser Ala Tyr Leu Asn Leu Ser Ser Glu Gln
        275                 280                 285

Asn Leu Ile Gln Glu Val Thr Val Gly Glu Gly Leu Asn Leu Lys Val
290                 295                 300

Met Val Glu Ala Tyr Pro Gly Leu Gln Gly Phe Asn Trp Thr Tyr Leu
305                 310                 315                 320

Gly Pro Phe Ser Asp His Gln Pro Glu Pro Lys Leu Ala Asn Ala Thr
                325                 330                 335
```

```
Thr Lys Asp Thr Tyr Arg His Thr Phe Thr Leu Ser Leu Pro Arg Leu
            340                 345                 350

Lys Pro Ser Glu Ala Gly Arg Tyr Ser Phe Leu Ala Arg Asn Pro Gly
            355                 360                 365

Gly Trp Arg Ala Leu Thr Phe Glu Leu Thr Leu Arg Tyr Pro Pro Glu
        370                 375                 380

Val Ser Val Ile Trp Thr Phe Ile Asn Gly Ser Gly Thr Leu Leu Cys
385                 390                 395                 400

Ala Ala Ser Gly Tyr Pro Gln Pro Asn Val Thr Trp Leu Gln Cys Ser
                405                 410                 415

Gly His Thr Asp Arg Cys Asp Glu Ala Gln Val Leu Gln Val Trp Asp
            420                 425                 430

Asp Pro Tyr Pro Glu Val Leu Ser Gln Glu Pro Phe His Lys Val Thr
            435                 440                 445

Val Gln Ser Leu Leu Thr Val Glu Thr Leu Glu His Asn Gln Thr Tyr
            450                 455                 460

Glu Cys Arg Ala His Asn Ser Val Gly Ser Gly Ser Trp Ala Phe Ile
465                 470                 475                 480

Pro Ile Ser Ala Gly Ala His Thr His Pro Pro Asp Glu
                485                 490

<210> SEQ ID NO 26
<211> LENGTH: 292
<212> TYPE: PRT
<213> ORGANISM: Artificial
<220> FEATURE:
<223> OTHER INFORMATION: human CSF-1R fragment D1-D3

<400> SEQUENCE: 26

Ile Pro Val Ile Glu Pro Ser Val Pro Glu Leu Val Val Lys Pro Gly
1               5                   10                  15

Ala Thr Val Thr Leu Arg Cys Val Gly Asn Gly Ser Val Glu Trp Asp
            20                  25                  30

Gly Pro Pro Ser Pro His Trp Thr Leu Tyr Ser Asp Gly Ser Ser Ser
        35                  40                  45

Ile Leu Ser Thr Asn Asn Ala Thr Phe Gln Asn Thr Gly Thr Tyr Arg
    50                  55                  60

Cys Thr Glu Pro Gly Asp Pro Leu Gly Gly Ser Ala Ala Ile His Leu
65                  70                  75                  80

Tyr Val Lys Asp Pro Ala Arg Pro Trp Asn Val Leu Ala Gln Glu Val
                85                  90                  95

Val Val Phe Glu Asp Gln Asp Ala Leu Leu Pro Cys Leu Leu Thr Asp
            100                 105                 110

Pro Val Leu Glu Ala Gly Val Ser Leu Val Arg Val Arg Gly Arg Pro
        115                 120                 125

Leu Met Arg His Thr Asn Tyr Ser Phe Ser Pro Trp His Gly Phe Thr
    130                 135                 140

Ile His Arg Ala Lys Phe Ile Gln Ser Gln Asp Tyr Gln Cys Ser Ala
145                 150                 155                 160

Leu Met Gly Gly Arg Lys Val Met Ser Ile Ser Ile Arg Leu Lys Val
                165                 170                 175

Gln Lys Val Ile Pro Gly Pro Pro Ala Leu Thr Leu Val Pro Ala Glu
            180                 185                 190

Leu Val Arg Ile Arg Gly Glu Ala Ala Gln Ile Val Cys Ser Ala Ser
        195                 200                 205
```

```
Ser Val Asp Val Asn Phe Asp Val Phe Leu Gln His Asn Asn Thr Lys
    210                 215                 220

Leu Ala Ile Pro Gln Gln Ser Asp Phe His Asn Asn Arg Tyr Gln Lys
225                 230                 235                 240

Val Leu Thr Leu Asn Leu Asp Gln Val Asp Phe Gln His Ala Gly Asn
                245                 250                 255

Tyr Ser Cys Val Ala Ser Asn Val Gln Gly Lys His Ser Thr Ser Met
            260                 265                 270

Phe Phe Arg Val Val Glu Ser Ala Tyr Leu Asn Leu Ser Ser Glu Gln
        275                 280                 285

Asn Leu Ile Gln
    290

<210> SEQ ID NO 27
<211> LENGTH: 218
<212> TYPE: PRT
<213> ORGANISM: Artificial
<220> FEATURE:
<223> OTHER INFORMATION: human CSF-1R fragment domains D4-D5

<400> SEQUENCE: 27

Val Val Glu Ser Ala Tyr Leu Asn Leu Ser Ser Glu Gln Asn Leu Ile
1               5                   10                  15

Gln Glu Val Thr Val Gly Glu Gly Leu Asn Leu Lys Val Met Val Glu
                20                  25                  30

Ala Tyr Pro Gly Leu Gln Gly Phe Asn Trp Thr Tyr Leu Gly Pro Phe
            35                  40                  45

Ser Asp His Gln Pro Glu Pro Lys Leu Ala Asn Ala Thr Thr Lys Asp
        50                  55                  60

Thr Tyr Arg His Thr Phe Thr Leu Ser Leu Pro Arg Leu Lys Pro Ser
65                  70                  75                  80

Glu Ala Gly Arg Tyr Ser Phe Leu Ala Arg Asn Pro Gly Gly Trp Arg
                85                  90                  95

Ala Leu Thr Phe Glu Leu Thr Leu Arg Tyr Pro Pro Glu Val Ser Val
            100                 105                 110

Ile Trp Thr Phe Ile Asn Gly Ser Gly Thr Leu Leu Cys Ala Ala Ser
        115                 120                 125

Gly Tyr Pro Gln Pro Asn Val Thr Trp Leu Gln Cys Ser Gly His Thr
130                 135                 140

Asp Arg Cys Asp Glu Ala Gln Val Leu Gln Val Trp Asp Asp Pro Tyr
145                 150                 155                 160

Pro Glu Val Leu Ser Gln Glu Pro Phe His Lys Val Thr Val Gln Ser
                165                 170                 175

Leu Leu Thr Val Glu Thr Leu Glu His Asn Gln Thr Tyr Glu Cys Arg
            180                 185                 190

Ala His Asn Ser Val Gly Ser Gly Ser Trp Ala Phe Ile Pro Ile Ser
        195                 200                 205

Ala Gly Ala His Thr His Pro Pro Asp Glu
    210                 215

<210> SEQ ID NO 28
<211> LENGTH: 554
<212> TYPE: PRT
<213> ORGANISM: homo sapiens
```

<400> SEQUENCE: 28

```
Met Thr Ala Pro Gly Ala Ala Gly Arg Cys Pro Pro Thr Thr Trp Leu
1               5                   10                  15

Gly Ser Leu Leu Leu Leu Val Cys Leu Leu Ala Ser Arg Ser Ile Thr
            20                  25                  30

Glu Glu Val Ser Glu Tyr Cys Ser His Met Ile Gly Ser Gly His Leu
        35                  40                  45

Gln Ser Leu Gln Arg Leu Ile Asp Ser Gln Met Glu Thr Ser Cys Gln
    50                  55                  60

Ile Thr Phe Glu Phe Val Asp Gln Glu Gln Leu Lys Asp Pro Val Cys
65                  70                  75                  80

Tyr Leu Lys Lys Ala Phe Leu Leu Val Gln Asp Ile Met Glu Asp Thr
                85                  90                  95

Met Arg Phe Arg Asp Asn Thr Pro Asn Ala Ile Ala Ile Val Gln Leu
            100                 105                 110

Gln Glu Leu Ser Leu Arg Leu Lys Ser Cys Phe Thr Lys Asp Tyr Glu
        115                 120                 125

Glu His Asp Lys Ala Cys Val Arg Thr Phe Tyr Glu Thr Pro Leu Gln
    130                 135                 140

Leu Leu Glu Lys Val Lys Asn Val Phe Asn Glu Thr Lys Asn Leu Leu
145                 150                 155                 160

Asp Lys Asp Trp Asn Ile Phe Ser Lys Asn Cys Asn Asn Ser Phe Ala
                165                 170                 175

Glu Cys Ser Ser Gln Asp Val Val Thr Lys Pro Asp Cys Asn Cys Leu
            180                 185                 190

Tyr Pro Lys Ala Ile Pro Ser Ser Asp Pro Ala Ser Val Ser Pro His
        195                 200                 205

Gln Pro Leu Ala Pro Ser Met Ala Pro Val Ala Gly Leu Thr Trp Glu
    210                 215                 220

Asp Ser Glu Gly Thr Glu Gly Ser Ser Leu Leu Pro Gly Glu Gln Pro
225                 230                 235                 240

Leu His Thr Val Asp Pro Gly Ser Ala Lys Gln Arg Pro Pro Arg Ser
                245                 250                 255

Thr Cys Gln Ser Phe Glu Pro Pro Glu Thr Pro Val Val Lys Asp Ser
            260                 265                 270

Thr Ile Gly Gly Ser Pro Gln Pro Arg Pro Ser Val Gly Ala Phe Asn
        275                 280                 285

Pro Gly Met Glu Asp Ile Leu Asp Ser Ala Met Gly Thr Asn Trp Val
    290                 295                 300

Pro Glu Glu Ala Ser Gly Glu Ala Ser Glu Ile Pro Val Pro Gln Gly
305                 310                 315                 320

Thr Glu Leu Ser Pro Ser Arg Pro Gly Gly Gly Ser Met Gln Thr Glu
                325                 330                 335

Pro Ala Arg Pro Ser Asn Phe Leu Ser Ala Ser Ser Pro Leu Pro Ala
            340                 345                 350

Ser Ala Lys Gly Gln Gln Pro Ala Asp Val Thr Gly Thr Ala Leu Pro
        355                 360                 365

Arg Val Gly Pro Val Arg Pro Thr Gly Gln Asp Trp Asn His Thr Pro
    370                 375                 380

Gln Lys Thr Asp His Pro Ser Ala Leu Leu Arg Asp Pro Pro Glu Pro
385                 390                 395                 400

Gly Ser Pro Arg Ile Ser Ser Leu Arg Pro Gln Gly Leu Ser Asn Pro
                405                 410                 415
```

```
Ser Thr Leu Ser Ala Gln Pro Gln Leu Ser Arg Ser His Ser Ser Gly
            420                 425                 430

Ser Val Leu Pro Leu Gly Glu Leu Gly Arg Ser Thr Arg Asp
            435                 440                 445

Arg Arg Ser Pro Ala Glu Pro Glu Gly Gly Pro Ala Ser Glu Gly Ala
450                 455                 460

Ala Arg Pro Leu Pro Arg Phe Asn Ser Val Pro Leu Thr Asp Thr Gly
465                 470                 475                 480

His Glu Arg Gln Ser Glu Gly Ser Phe Ser Pro Gln Leu Gln Glu Ser
            485                 490                 495

Val Phe His Leu Leu Val Pro Ser Val Ile Leu Val Leu Leu Ala Val
            500                 505                 510

Gly Gly Leu Leu Phe Tyr Arg Trp Arg Arg Ser His Gln Glu Pro
            515                 520                 525

Gln Arg Ala Asp Ser Pro Leu Glu Gln Pro Glu Gly Ser Pro Leu Thr
            530                 535                 540

Gln Asp Asp Arg Gln Val Glu Leu Pro Val
545                 550

<210> SEQ ID NO 29
<211> LENGTH: 242
<212> TYPE: PRT
<213> ORGANISM: homo sapiens

<400> SEQUENCE: 29

Met Pro Arg Gly Phe Thr Trp Leu Arg Tyr Leu Gly Ile Phe Leu Gly
1               5                   10                  15

Val Ala Leu Gly Asn Glu Pro Leu Glu Met Trp Pro Leu Thr Gln Asn
            20                  25                  30

Glu Glu Cys Thr Val Thr Gly Phe Leu Arg Asp Lys Leu Gln Tyr Arg
        35                  40                  45

Ser Arg Leu Gln Tyr Met Lys His Tyr Phe Pro Ile Asn Tyr Lys Ile
    50                  55                  60

Ser Val Pro Tyr Glu Gly Val Phe Arg Ile Ala Asn Val Thr Arg Leu
65                  70                  75                  80

Gln Arg Ala Gln Val Ser Glu Arg Glu Leu Arg Tyr Leu Trp Val Leu
                85                  90                  95

Val Ser Leu Ser Ala Thr Glu Ser Val Gln Asp Val Leu Leu Glu Gly
            100                 105                 110

His Pro Ser Trp Lys Tyr Leu Gln Glu Val Glu Thr Leu Leu Leu Asn
        115                 120                 125

Val Gln Gln Gly Leu Thr Asp Val Glu Val Ser Pro Lys Val Glu Ser
    130                 135                 140

Val Leu Ser Leu Leu Asn Ala Pro Gly Pro Asn Leu Lys Leu Val Arg
145                 150                 155                 160

Pro Lys Ala Leu Leu Asp Asn Cys Phe Arg Val Met Glu Leu Leu Tyr
                165                 170                 175

Cys Ser Cys Cys Lys Gln Ser Ser Val Leu Asn Trp Gln Asp Cys Glu
            180                 185                 190

Val Pro Ser Pro Gln Ser Cys Ser Pro Glu Pro Ser Leu Gln Tyr Ala
        195                 200                 205

Ala Thr Gln Leu Tyr Pro Pro Pro Pro Trp Ser Pro Ser Ser Pro Pro
    210                 215                 220
```

His Ser Thr Gly Ser Val Arg Pro Val Arg Ala Gln Gly Glu Gly Leu
225                 230                 235                 240

Leu Pro

<210> SEQ ID NO 30
<211> LENGTH: 277
<212> TYPE: PRT
<213> ORGANISM: homo sapiens

<400> SEQUENCE: 30

Met Val Arg Leu Pro Leu Gln Cys Val Leu Trp Gly Cys Leu Leu Thr
1               5                   10                  15

Ala Val His Pro Glu Pro Thr Ala Cys Arg Glu Lys Gln Tyr Leu
            20                  25                  30

Ile Asn Ser Gln Cys Cys Ser Leu Cys Gln Pro Gly Gln Lys Leu Val
            35                  40                  45

Ser Asp Cys Thr Glu Phe Thr Glu Thr Glu Cys Leu Pro Cys Gly Glu
    50                  55                  60

Ser Glu Phe Leu Asp Thr Trp Asn Arg Glu Thr His Cys His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
            115                 120                 125

Phe Gly Val Lys Gln Ile Ala Thr Gly Val Ser Asp Thr Ile Cys Glu
130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Gln Asp Arg Leu
            180                 185                 190

Arg Ala Leu Val Val Ile Pro Ile Ile Phe Gly Ile Leu Phe Ala Ile
            195                 200                 205

Leu Leu Val Leu Val Phe Ile Lys Lys Val Ala Lys Lys Pro Thr Asn
210                 215                 220

Lys Ala Pro His Pro Lys Gln Glu Pro Gln Glu Ile Asn Phe Pro Asp
225                 230                 235                 240

Asp Leu Pro Gly Ser Asn Thr Ala Ala Pro Val Gln Glu Thr Leu His
                245                 250                 255

Gly Cys Gln Pro Val Thr Gln Glu Asp Gly Lys Glu Ser Arg Ile Ser
            260                 265                 270

Val Gln Glu Arg Gln
        275

<210> SEQ ID NO 31
<211> LENGTH: 290
<212> TYPE: PRT
<213> ORGANISM: homo sapiens

<400> SEQUENCE: 31

```
Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
                20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
        50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Asn Glu Ile Phe Tyr
        195                 200                 205

Cys Thr Phe Arg Arg Leu Asp Pro Glu Glu Asn His Thr Ala Glu Leu
        210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290
```

<210> SEQ ID NO 32
<211> LENGTH: 1032
<212> TYPE: PRT
<213> ORGANISM: homo sapiens

<400> SEQUENCE: 32

```
Met Gly Phe Cys Arg Ser Ala Leu His Pro Leu Ser Leu Leu Val Gln
1               5                   10                  15

Ala Ile Met Leu Ala Met Thr Leu Ala Leu Gly Thr Leu Pro Ala Phe
                20                  25                  30

Leu Pro Cys Glu Leu Gln Pro His Gly Leu Val Asn Cys Asn Trp Leu
            35                  40                  45

Phe Leu Lys Ser Val Pro His Phe Ser Met Ala Ala Pro Arg Gly Asn
        50                  55                  60
```

```
Val Thr Ser Leu Ser Leu Ser Ser Asn Arg Ile His His Leu His Asp
 65                  70                  75                  80

Ser Asp Phe Ala His Leu Pro Ser Leu Arg His Leu Asn Leu Lys Trp
                 85                  90                  95

Asn Cys Pro Pro Val Gly Leu Ser Pro Met His Phe Pro Cys His Met
            100                 105                 110

Thr Ile Glu Pro Ser Thr Phe Leu Ala Val Pro Thr Leu Glu Glu Leu
        115                 120                 125

Asn Leu Ser Tyr Asn Asn Ile Met Thr Val Pro Ala Leu Pro Lys Ser
    130                 135                 140

Leu Ile Ser Leu Ser Leu Ser His Thr Asn Ile Leu Met Leu Asp Ser
145                 150                 155                 160

Ala Ser Leu Ala Gly Leu His Ala Leu Arg Phe Leu Phe Met Asp Gly
                165                 170                 175

Asn Cys Tyr Tyr Lys Asn Pro Cys Arg Gln Ala Leu Glu Val Ala Pro
            180                 185                 190

Gly Ala Leu Leu Gly Leu Gly Asn Leu Thr His Leu Ser Leu Lys Tyr
        195                 200                 205

Asn Asn Leu Thr Val Val Pro Arg Asn Leu Pro Ser Ser Leu Glu Tyr
    210                 215                 220

Leu Leu Leu Ser Tyr Asn Arg Ile Val Lys Leu Ala Pro Glu Asp Leu
225                 230                 235                 240

Ala Asn Leu Thr Ala Leu Arg Val Leu Asp Val Gly Gly Asn Cys Arg
                245                 250                 255

Arg Cys Asp His Ala Pro Asn Pro Cys Met Glu Cys Pro Arg His Phe
            260                 265                 270

Pro Gln Leu His Pro Asp Thr Phe Ser His Leu Ser Arg Leu Glu Gly
        275                 280                 285

Leu Val Leu Lys Asp Ser Ser Leu Ser Trp Leu Asn Ala Ser Trp Phe
    290                 295                 300

Arg Gly Leu Gly Asn Leu Arg Val Leu Asp Leu Ser Glu Asn Phe Leu
305                 310                 315                 320

Tyr Lys Cys Ile Thr Lys Thr Lys Ala Phe Gln Gly Leu Thr Gln Leu
                325                 330                 335

Arg Lys Leu Asn Leu Ser Phe Asn Tyr Gln Lys Arg Val Ser Phe Ala
            340                 345                 350

His Leu Ser Leu Ala Pro Ser Phe Gly Ser Leu Val Ala Leu Lys Glu
        355                 360                 365

Leu Asp Met His Gly Ile Phe Phe Arg Ser Leu Asp Glu Thr Thr Leu
    370                 375                 380

Arg Pro Leu Ala Arg Leu Pro Met Leu Gln Thr Leu Arg Leu Gln Met
385                 390                 395                 400

Asn Phe Ile Asn Gln Ala Gln Leu Gly Ile Phe Arg Ala Phe Pro Gly
                405                 410                 415

Leu Arg Tyr Val Asp Leu Ser Asp Asn Arg Ile Ser Gly Ala Ser Glu
            420                 425                 430

Leu Thr Ala Thr Met Gly Glu Ala Asp Gly Gly Glu Lys Val Trp Leu
        435                 440                 445

Gln Pro Gly Asp Leu Ala Pro Ala Pro Val Asp Thr Pro Ser Ser Glu
    450                 455                 460

Asp Phe Arg Pro Asn Cys Ser Thr Leu Asn Phe Thr Leu Asp Leu Ser
465                 470                 475                 480
```

```
Arg Asn Asn Leu Val Thr Val Gln Pro Glu Met Phe Ala Gln Leu Ser
                    485                 490                 495

His Leu Gln Cys Leu Arg Leu Ser His Asn Cys Ile Ser Gln Ala Val
            500                 505                 510

Asn Gly Ser Gln Phe Leu Pro Leu Thr Gly Leu Gln Val Leu Asp Leu
        515                 520                 525

Ser His Asn Lys Leu Asp Leu Tyr His Glu His Ser Phe Thr Glu Leu
    530                 535                 540

Pro Arg Leu Glu Ala Leu Asp Leu Ser Tyr Asn Ser Gln Pro Phe Gly
545                 550                 555                 560

Met Gln Gly Val Gly His Asn Phe Ser Phe Val Ala His Leu Arg Thr
                565                 570                 575

Leu Arg His Leu Ser Leu Ala His Asn Asn Ile His Ser Gln Val Ser
            580                 585                 590

Gln Gln Leu Cys Ser Thr Ser Leu Arg Ala Leu Asp Phe Ser Gly Asn
        595                 600                 605

Ala Leu Gly His Met Trp Ala Glu Gly Asp Leu Tyr Leu His Phe Phe
    610                 615                 620

Gln Gly Leu Ser Gly Leu Ile Trp Leu Asp Leu Ser Gln Asn Arg Leu
625                 630                 635                 640

His Thr Leu Leu Pro Gln Thr Leu Arg Asn Leu Pro Lys Ser Leu Gln
                645                 650                 655

Val Leu Arg Leu Arg Asp Asn Tyr Leu Ala Phe Phe Lys Trp Trp Ser
            660                 665                 670

Leu His Phe Leu Pro Lys Leu Glu Val Leu Asp Leu Ala Gly Asn Gln
        675                 680                 685

Leu Lys Ala Leu Thr Asn Gly Ser Leu Pro Ala Gly Thr Arg Leu Arg
    690                 695                 700

Arg Leu Asp Val Ser Cys Asn Ser Ile Ser Phe Val Ala Pro Gly Phe
705                 710                 715                 720

Phe Ser Lys Ala Lys Glu Leu Arg Glu Leu Asn Leu Ser Ala Asn Ala
                725                 730                 735

Leu Lys Thr Val Asp His Ser Trp Phe Gly Pro Leu Ala Ser Ala Leu
            740                 745                 750

Gln Ile Leu Asp Val Ser Ala Asn Pro Leu His Cys Ala Cys Gly Ala
        755                 760                 765

Ala Phe Met Asp Phe Leu Leu Glu Val Gln Ala Ala Val Pro Gly Leu
    770                 775                 780

Pro Ser Arg Val Lys Cys Gly Ser Pro Gly Gln Leu Gln Gly Leu Ser
785                 790                 795                 800

Ile Phe Ala Gln Asp Leu Arg Leu Cys Leu Asp Glu Ala Leu Ser Trp
                805                 810                 815

Asp Cys Phe Ala Leu Ser Leu Leu Ala Val Ala Leu Gly Leu Gly Val
            820                 825                 830

Pro Met Leu His His Leu Cys Gly Trp Asp Leu Trp Tyr Cys Phe His
    835                 840                 845

Leu Cys Leu Ala Trp Leu Pro Trp Arg Gly Arg Gln Ser Gly Arg Asp
850                 855                 860

Glu Asp Ala Leu Pro Tyr Asp Ala Phe Val Val Phe Asp Lys Thr Gln
865                 870                 875                 880

Ser Ala Val Ala Asp Trp Val Tyr Asn Glu Leu Arg Gly Gln Leu Glu
                885                 890                 895
```

-continued

Glu Cys Arg Gly Arg Trp Ala Leu Arg Leu Cys Leu Glu Glu Arg Asp
                900                 905                 910

Trp Leu Pro Gly Lys Thr Leu Phe Glu Asn Leu Trp Ala Ser Val Tyr
        915                 920                 925

Gly Ser Arg Lys Thr Leu Phe Val Leu Ala His Thr Asp Arg Val Ser
        930                 935                 940

Gly Leu Leu Arg Ala Ser Phe Leu Leu Ala Gln Gln Arg Leu Leu Glu
945                 950                 955                 960

Asp Arg Lys Asp Val Val Leu Val Ile Leu Ser Pro Asp Gly Arg
                965                 970                 975

Arg Ser Arg Tyr Val Arg Leu Arg Gln Arg Leu Cys Arg Gln Ser Val
            980                 985                 990

Leu Leu Trp Pro His Gln Pro Ser Gly Gln Arg Ser Phe Trp Ala Gln
            995                 1000                1005

Leu Gly Met Ala Leu Thr Arg Asp Asn His His Phe Tyr Asn Arg
        1010                1015                1020

Asn Phe Cys Gln Gly Pro Thr Ala Glu
        1025                1030

<210> SEQ ID NO 33
<211> LENGTH: 107
<212> TYPE: PRT
<213> ORGANISM: Homo sapiens

<400> SEQUENCE: 33

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 34
<211> LENGTH: 330
<212> TYPE: PRT
<213> ORGANISM: Homo sapiens

<400> SEQUENCE: 34

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 35
<211> LENGTH: 330
<212> TYPE: PRT
<213> ORGANISM: Artificial
<220> FEATURE:
<223> OTHER INFORMATION: human heavy chain constant region derived from
      IgG1 mutated on L234A and L235A

<400> SEQUENCE: 35

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

-continued

```
Pro Ala Pro Glu Ala Ala Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 36
<211> LENGTH: 327
<212> TYPE: PRT
<213> ORGANISM: Homo sapiens

<400> SEQUENCE: 36

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160
```

```
Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 37
<211> LENGTH: 327
<212> TYPE: PRT
<213> ORGANISM: Artificial
<220> FEATURE:
<223> OTHER INFORMATION: human heavy chain constant region derived from
      IgG4 mutated onS228P

<400> SEQUENCE: 37

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190
```

-continued

```
Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Glu Glu Met Thr Lys
225                     230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                     310                 315                 320

Leu Ser Leu Ser Leu Gly Lys
                325
```